(12) United States Patent
Bassler et al.

(10) Patent No.: US 6,720,415 B2
(45) Date of Patent: Apr. 13, 2004

(54) COMPOSITIONS AND METHODS FOR REGULATING BACTERIAL PATHOGENESIS

(75) Inventors: Bonnie L. Bassler, Princeton, NJ (US); Michael G. Surette, Calgary (CA)

(73) Assignees: Princeton University, Princeton, NJ (US); University Technologies International (CA)

(*) Notice: Subject to any disclaimer, the term of this patent is extended or adjusted under 35 U.S.C. 154(b) by 0 days.

(21) Appl. No.: 09/453,976

(22) Filed: Dec. 2, 1999

(65) Prior Publication Data

US 2003/0148414 A1 Aug. 7, 2003

Related U.S. Application Data

(60) Provisional application No. 60/110,570, filed on Dec. 2, 1998, now abandoned.

(51) Int. Cl.⁷ .............................................. C07H 21/04
(52) U.S. Cl. .................. 536/23.7; 536/23.2; 536/23.1; 536/23.4; 514/44; 514/2; 435/6; 435/69.1; 435/69.7; 435/29; 435/4; 435/476
(58) Field of Search ................................ 435/476, 486, 435/29, 4, 6, 69.1, 69.7; 514/2, 44; 536/23.2, 23.4, 23.7

(56) References Cited

U.S. PATENT DOCUMENTS

| | | | |
|---|---|---|---|
| 4,107,121 A | 8/1978 | Stoy | |
| 4,692,417 A | 9/1987 | Webster | 436/518 |
| 4,861,709 A | 8/1989 | Ulitzur et al. | 435/6 |
| 4,895,566 A | 1/1990 | Lee | |
| 4,917,686 A | 4/1990 | Bayston et al. | |
| 4,952,419 A | 8/1990 | De Leon et al. | |
| 5,013,306 A | 5/1991 | Solomon et al. | |
| 5,166,057 A | * 11/1992 | Palese et al. | 435/69.1 |
| 5,196,318 A | 3/1993 | Baldwin et al. | 435/69.1 |
| 5,593,827 A | 1/1997 | Bycroft et al. | |
| 5,612,184 A | 3/1997 | Rosson | |
| 5,637,113 A | 6/1997 | Tartaglia et al. | |
| 5,658,748 A | 8/1997 | Mäyra-Mäkinen et al. | |
| 5,759,798 A | * 6/1998 | Dunlap | 435/29 |
| 5,788,979 A | 8/1998 | Alt et al. | |
| 5,902,283 A | 5/1999 | Darouiche et al. | |

(List continued on next page.)

FOREIGN PATENT DOCUMENTS

| | | |
|---|---|---|
| WO | WO 98/13328 | 4/1998 |
| WO | WO 98/40346 | 9/1998 |
| WO | WO 98/58075 | 12/1998 |
| WO | WO 99/00349 | 1/1999 |
| WO | WO 99/01119 | 1/1999 |
| WO | WO 99/29647 | 6/1999 |
| WO | WO 99/47545 | 9/1999 |
| WO | WO 00/11021 | 3/2000 |
| WO | WO 01/85664 A2 | 11/2001 |

OTHER PUBLICATIONS

Fleishmann, R.D. et al, Science, vol. 269, pp. 496–512, 1995.*

(List continued on next page.)

*Primary Examiner*—Mark Navarro
*Assistant Examiner*—Ginny Allen Portner
(74) *Attorney, Agent, or Firm*—Knobbe Martens Olson & Bear LLP

(57) ABSTRACT

This invention provides a purified extracellular bacterial autoinducer-2 signaling molecule, the production of which is regulated by changes in environmental conditions associated with a shift from a free-living existence to a colonizing or pathogenic existence in a host organism. The signaling molecule stimulates LuxQ luminescence genes, and is believed also to stimulate a variety of pathogenesis related genes in the bacterial species that produce it. This invention also provides is a new class of bacterial genes involved in the biosynthesis of the signaling molecule.

6 Claims, 17 Drawing Sheets

Hybrid quorum sensing circuit of Vibrio harveyi

U.S. PATENT DOCUMENTS

| | | | | |
|---|---|---|---|---|
| 5,925,552 | A | | 7/1999 | Keogh et al. |
| 6,017,722 | A | | 1/2000 | Becvar et al. ................. 435/8 |
| 6,020,121 | A | * | 2/2000 | Bao .............................. 435/4 |
| 6,057,288 | A | * | 5/2000 | Pearson et al. ................ 514/2 |
| 6,117,485 | A | | 9/2000 | Woodhall et al. |
| 6,197,591 | B1 | * | 3/2001 | Stutzman-Engwall et al. ............. 435/486 |
| 6,559,176 | B1 | * | 5/2003 | Bassler et al. .............. 514/408 |

OTHER PUBLICATIONS

Kuntz, F et al, Nature, vol. 390(6657), pp. 249–256, 1997, coding sequence for "jtjb".*

Swiss–Prot and TrEMBL for LuxS polypeptides, polypeptide accession Nos. Q9K7K8;O34667;O50164; Q9PN97;Q97F13;Q9XDU6;Q9RRU8;Q8X902;Q8FEP8; P45578;Q9ZMW8;O24931;Q9CIUO;Q92.*

Fraser, CM et al, Accession No. AE00143, created date Dec. 16, 1997, in Nature, vol. 390(660), pp. 580–586, 1997.*

Tomb, JF et al, Accession No. AE000532, created date Aug. 25, 1997, in Nature vol. 388(6642), pp. 539–547, 1997.*

Surette, MG et al, PNAS, vol. 96, pp. 1639–1644, Feb. 1999.*

Melangeli, C et al, PNAS, vol. 94, pp. 2255–2260, Mar. 1997.*

Eberhard et al., *American Chemical Society*, 20(9):2444–2449 (1981).

Martin et al., *Journal of Bacteriology*, 171(5);2406–2414 (May 1989).

Showalter et al., *Journal of Bacteriology*, 172(6):2946–2954 (Jun. 1990).

Bassler et al., *Molecular Microbiology*, 13(2):273–286.

Mancini et al., *Journal of Biological Chemistry*, 263(28):14308–14314 (1988).

Jones, S., et al., The EMBO Journal, vol. 12(6), pp. 2477–2482, 1993.

Kuo, et al., "Modulation of Luminescence Operon Expression by N–Octanoyl–L–Homoserine Lactone in ainS Mutants of *Vibrio fischerii*" *Journal of Bacteriology*, vol. 178, No. 4, Feb. 1996, pp. 971–976.

Lin, J., et al., Biochemical and Biophysical Research Communications, pp. 938–947, May 24, 1995, vol. 210(3).

Lin, J., et al., Biochemical and Biophysical Research Communications, vol. 219, pp. 868–875, 1996.

Salmond, G.P.C., et al., Molecular Microbiology, vol. 16(4), pp. 615–624, 1995.

Sun, T.S.C., et al., Journal of AOAC International, vol. 76(4), pp. 893–898, 1993.

Swift, S., et al., Molecular Microbiology, vol. (10)3, pp. 511–520, 1993.

Becker et al. (1997) "Evidence for Interspecies Communication and its Potential Role in Pathogen Suppression in a Naturally Occurring Disease Suppressive Soil", *Canadian Journal of Microbiology*, 43:985–990.

Manefield et al. (2001) "Halogenated Furanones from the Red Alga, *Delisea pulchra*, Inhibit Carbapenem Antibiotic Synthesis and Exoenzyme Virulence Factor Production in the Phytopathogen *Erwinia carotovora*", *Federation of European Microbiological Societies—Microbiology Letters*, 205:131–138.

Schaefer et al. (1996) "Quorum Sensing in *Vibrio fischeri*: Probing Autoinducer–LuxR Interactions with Autoinducer Analogs", *Journal of Bacteriology*, 178(10):2897–2901.

Sofer et al. (1999)"'Subinhibitory' Erythromycin Represses Production of *Pseudomonas aeruginosa* Lectins, Autoinducer and Virulence Factors", *Chemotherapy Microbiology*, 45:335–341.

Lilley et al. (2000) "Regulation of Quorum Sensing in *Vibrio harveyi* by LuxO and Sigma–54", *Molecular Microbiology*, 6(4):940–954, Blackwell Science Ltd.

Klose et al. (1998) "Identification of Multiple $\sigma^{54}$–Dependent Transcriptional Activators in *Vibrio chlorae*" *Journal of Bacteriology*, 180(19):5256–5259, American Society for Microbiology.

Swartzman et al. (1992) "*Vibrio harveyi* RNA Polymerase: Purification and Resolution from Gyrase A" *Biochemistry Cell Biology*, 70:698–702.

O'Toole et al. (1997) "RpoN of the Fish Pathogen *Vibrio* (*Listonella*) *anguillarum* is Essential for Flagellum Production and Virulence by the Water–Borne but not Intraperitoneal Route of Inoculation" *Microbiology*, 143:3849–3859.

Ikegami et al. (2000) "Cloning and Characterization of the Gene Encoding RNA Polymerase Sigma Factor $\sigma$–$^{54}$ of Deep–Sea Piezophilic *Shewanella violacea*" *Biochimica et Biophysica Acta*, 1491:315–320.

Kawagishi et al. (1997) "Cloning of *Vibrio alginolyticus rpoN* Gene that is Required for Polar Flagellar Formation" *Journal of Bacteriology*, 179(21):6851–6854, American Society for Microbiology.

Fuqua, C. et al, Annual Review of Microbiology, vol. 50, pp. 727–751, 1996, Census and consensus in bacterial ecosystems: the LuxR–LuxI family of quorum–sensing transcriptional regulators.*

Pesci, E.C. et al., Journal of Bacteriology, vol. 179(10), pp. 3127–3132, Regulation of las and rhl Quorum sensing in *Pseudomonas aeruginosa* , 1997.*

Genbank Accession No. AE000353, dated Nov. 1, 1997, Autoinducer–2 production protein LuxS.*

Adams et al., "The expression of hybrid HIV : Ty virus–like particles in yeast" Nature, vol. 329, pp. 68–70 (Sep. 3, 1987).

Ahmer et al., "*Salmonella typhimurium* Encodes an SdiA Homolog, a Putative Quorum Sensor of the LuxR Family, That Regulates Genes on the Virulence Plasmid", *Journal of Bacteriology*, pp. 1185–1193 (Mar. 1998).

Allart et al., "The catalytic mechanism of adenosylhomocysteine/methylthioadenosine nucleosidase from *Escherichia coli*: Chemical evidence for a transition state with a substantial oxocarbenium character" *Eur. J. Biochem.*, 256, pp. 155–162 (1998).

Baines et al., "Purification of Immunoglobulin G (IgG)" *Methods in Molecular Biology*, vol. 10: Immunochemical Protocols, Ed: M. Manson (1992).

Bassler et al. "Intercellular signaling in *Vibrio harveyi*: sequence and function of genes regulating expression of luminescence" *Molecular Microbiology*, 9(4) 773–786 (1993).

Bassler et al. "Intercellular Communication in Marine Vibrio Species: Density–Dependent Regulation of the Expression of Bioluminescence" *Two–Component Signal Transduction*, pp. 431–445 (1995).

Bassler et al., "Cross–Species Induction of Luminescence in the Qurorum–Sensing Bacterium *Vibrio harveyi*", *Journal of Bacteriology*, vol. 179, No. 12, pp. 4043–4045 (Jun. 1997).

Bassler, "How bacteria talk to each other: regulation of gene expression by quorum sensing" *Current Opinion in Microbiology*, 2:582–587 (1999).

Bassler et al., "A Multichannel Two–Component Signaling Relay Controls Quorum Sensing in *Vibrio Harveyi*" *Cell–Cell Signaling in Bacteria*, pp. 259–273 (1999).

Bitter, "Heterologous Gene Expression in Yeast" *Methods in Enzymology*, vol. 152, pp. 673–684 (1987).

Bitter et al. "Expression and Secretion Vectors for Yeast-"*Methods in Enzymology*, vol. 153, pp. 516–544 (1987).

Blattner et al. "The Complete Genome Sequence of *Escherichia coli* K–12"*Science*, vol. 277 (5331) pp. 1453–1462 (1997), Sep.

Brückner et al. "Regulation of the inducible chloramphenicol acetyltransferase gene of the *Staphylococcus aureus* plasmid pUB112" *The EMBO Journal*, vol. 4, No. 9, pp. 2295–2300 (1985).

Caetano–Annollés, "Amplifying DNA with Arbitrary Oligonucleotide Primers" *PCR Methods and Applications*, 3:85–94 (1993).

Cheung et al. "Diminished Virulence of a sar~lag~Mutant of *Staphylooccus aureus* in the Rabbit Model of Endocarditis" *The Journal of Clinical Investigation, Inc.*, vol. 94, pp. 1815–1822 (1994).

Conner et al., "Detection of sickle cell $\beta^S$–globin allele by hybridization with synthetic oligonucleotides" *Proc. Natl. Acad. Sci. USA*, vol. 80, pp. 278–282 (Jan. 1983).

Cornell et al., "Characterization of Recombinant *Eschericha coli* 5'–Methylthioadenosine/S–Adenosylhomocysteine Nucleosidase: Analysis of Enzymatic Activity and Substrate Specificity" *Biochemical and Biophysical Research Communications*, 228, pp. 724–732, Article No. 1723 (1996).

Cornell and Riscoe, "Cloning and expression of *Eschericia coli* 5'–methylthioadenosine/S–adenosylhomocysteine nucleosidase Identification of the *pfs* gene product" *Biochemica et Biophysica Acta* 1396, pp. 8–14 (1998).

Devereux et al. "A comprehensive set of sequence analysis programs for the VAX" *Nucleic Acids Research*, vol. 12, No. 1, pp. 387–395 (1984).

Dodd et al., "Improved detection of helix–turn–helix DNA–binding motifs in protein sequences" *Nucleic Acids Research*, vol. 18, No. 17, pp. 5019–5026 (1990).

Duerre, "A Hydrolytic Nucleosidase Acting on S–Adenosylhomocysteine and 5'–Methylthiodenosine" *The Journal of Biological Chemistry*, vol. 237, No. 12 pp. 3737–3741 (Dec. 1962).

Duerre and Miller, "Cleavage of S–Rebosyl–L–Homocysteine by Extracts from *Escherichia coli*" *Journal of Bacteriology*, vol. 91, No. 3, pp. 1210–1217 (1966).

Eberhard et al. "Analogs of the autoinducer of bioluminescence in *Vibrio fischeri*" *Arch Microbiol*, 146:35–40 (1986).

Engebrecht et al. "Bacterial Bioluminescence: Isolation and Genetic Analysis of Functions from *Vibrio fischeri*" *Cell*, vol. 32, pp. 773–781 (1983).

Erion et al., "Purine Nucleoside Phosphorylase. 1. Structure–Function Studies"*Biochemistry*, 36, pp. 11725–11734 (1997).

Freeman and Bassler, "A genetic analysis of the function of LuxO, a two–component response regulator involved in quorum sensing in *Vibrio harveyi*", *Molecular Microbiology*, 31(2), pp. 665–677 (1999).

Freeman and Bassler, "Sequence and Function of LuxU: a Two Component Phosphorelay Protein That Regulates Quorum Sensing in *Virbrio harveyi*", *Journal of Bacteriology*, vol. 181, No. 3, pp. 899–906 (Feb. 1999).

Fuqua et al. "Quorum Sensing in Bacteria: the LuxR–LuxI Family of Cell Density–Responsive Transcriptional Regulators" *Journal of Bacteriology*, pp. 269–275 (Jan. 1994).

Garcia–Lara et al. "An Extracellular Factor Regulates Expression of *sdiA*, a Transcriptional Activator of Cell Division Genes in *Escherichia coli*" *Journal of Bacteriology*, pp. 2742–2748 (May 1996).

Gilson et al. "AinS and a New Family of Autoinducer Synthesis Proteins" *Journal of Bacteriology*, pp. 6946–6951 (Dec. 1995), vol. 177(23).

*Goodman and Gilman's The Pharmacological Basis of Therapeutics* $7^{th}$ Ed., Macmillan Publishing Company (1985).

*Goodman & Gilman's The Pharmacological Basis of Therapeutics*, $9^{th}$ Ed., "Chemotherapy of Microbial Diseases", Section IX, pp. 1027–1223 (1996).

Green and Manson, "Production of Polyclonal Antisera" *Methods in Molecular Biology*, vol. 10: Immunochemical Protocols Ed.: M. Manson, Ch. 1, pp. 1–5 (1992).

Greenberg et al. "Induction of Luciferase Synthesis in *Beneckea harveyi* by Other Marine Bacteria" *Arch Microbiol*, 120, pp. 87–91 (1979).

Harlow and Lane, *Antibodies: A Laboratory Manual*, Cold Spring Harbor Laboratory (1988).

Hu et al., "Crystal Structure of S–Adenosylhomocysteine Hydrolase from Rat Liver" *Biochemistry*, 38, pp. 8323–8333 (1999).

Huisman and Kolter, "Sensing Starvation: A Homoserine Lactone–Dependent Signaling Pathway in *Escherichia coli*" *Science*, vol. 265, pp. 537–539 (Jul. 22, 1994).

Jones et al., "Molecular analysis of the operon which encodes the RNA polymerase sigma factor $\sigma^{54}$ of *Escherichia coli*"*Microbiology*, 140, pp. 1035–1043 (1994).

Kaplan et al. "Synthesis of N–[3–OXO–(4,5–$^3$H2) –Hexanoyl]Homoserice Lactone: Biologically Active Tritium–Labelled *Vibrio Fischeri* Autoinducer" *Journal of Labelled Compounds and Radiopharmaceuticals*–vol. XXII, No. 4, pp. 387–395 (1985).

Keen, "Plants and Microorganisms–listening in on the conversation" *Nature Biotechnology*, vol. 17, pp. 958–959 (Oct. 1999).

Klose and Mekalanos, "Distinct roles of an alternative sigma factor during both free–swimming and colonizing phases of the *Vibrio cholerae* pathogenic cycle" *Molecular Microbiology*, 28(3), pp. 501–520 (1998).

Koellner et al., "Crystal Structure of the Ternary Complex of *E. coli* Purine Nucleoside Phosphorylase with Formycin B, a Structural Analogue of the Substrate Inosine, and Phosphate (Sulphate) at 2.1 A Resolution"*J. Mol. Biol.*, 280, pp. 153–166, Article No. mb981799 (1998).

Köhler and Milstein "Continuous cultures of fused cells secreting antibody of predefined specificity" *Nature*, vol. 256, pp. 495–497 (Aug. 7, 1975).

Landergreen et al., "A Ligase–Mediated Gene Detection Technique" *Science*, vol. 241, pp. 1077–1080 (Aug. 26, 1988).

Landergreen et al. "DNA Diagnostics–Molecular Techniques and Automation" *Science*, vol. 242, pp. 229–237 (Oct. 14, 1998).

Langer, "New Methods of Drug Delivery" *Science*, vol. 249, pp. 1527–1533 (Sep. 28, 1990).

Lee and Nathans, "Proliferin Secreted by Cultured Cells Bind to Mannose 6–Phosphate Receptors"*The Journal of Biological Chemistry*, vol. 263, No. 7, pp. 3521–3527 (Mar. 5, 1988).

Maloy et al., *Genetic Analysis of Pathogenic Bacteria: A Laboratory Manual*, Cold Spring Harbor Laboratory Press (1996).

Manefield et al., "Evidence that halogenated furanones from *Delisea pulchra* inhibit acylated homoserine lactone (AHL)–mediated gene expression by displacing the AHL signal from its receptor protein" *Microbiology*, 145, pp. 283–291, (1999).

Manefield et al., "Inhibition of Luminescence of Virulence in the Black Tiger Prawn (*Penaeus monodon*) Pathogen *Vibrio harveyi* by Intercellular Signal Antagonists" *Applied and Environmental Microbiology*, vol. 66, No. 5, pp. 2079–2084 (May 2000).

Mao et al., "The crystal structure of *Escherichia coli* purine nucleoside phosporylase: a comparison with the human enzyme reveals a conserved topology" *Structure*, Research Article, vol. 5, No. 10, pp. 1373–1383 (1997).

Marmur, "A Procedure for the Isolation of Deoxyribonucleic Acid from Micro–organisms" *J. Mol. Biol.*, 3, pp. 208–218 (1961).

Miller and Duerre, "S–Ribosylhomocysteine Cleavage Enzyme from *Escherichia coli*" *The Journal of Biological Chemistry*, vol. 243, No. 1, pp. 92–97 (1968).

Miller, *A Short Course in Bacterial Genetics: A Laboratory Manual and Handbook for Escherichia coli and Related Bacteria*, Cold Spring Harbor Laboratory Press (1992).

Nealson and Hastings, "Bacterial Bioluminescence: Its Control and Ecological Significance" *Microbiological Reviews*, pp. 496–518 (Dec. 1979).

Otto et al., "Structure of the pheromone peptide of the *Staphylococcus epidermidis* agr system" *FEBS Letters*, 424, pp. 89–94 (1998).

Otto et al., "Inhibition of virulence factor expression in *Staphylococcus aureus* by the *Staphylococcus epidermidis* agr pheromone and derivatives"*FEBS Letters*, 450, pp. 257–262 (1999).

Payne, "Detection, Isolation, and Characterization of Siderophores" *Methods in Enzymology*, vol. 235, pp. 329–344 (1994).

Plunkett and Ellman, "Combinatorial Chemistry and New Drugs" *Scientific American*, pp. 69–73, (Apr. 1997).

Poustka and Lehrach, "Genetic approaches to the cloning modification and characterization of cosmid clones and clone libraries" *Choice and use of cosmid vectors*, Ch. 3, pp. 57.

*Remington's Pharmaceutical Sciences*, $15^{th}$ Ed. Easton, Mack Publishing Co., pp. 1461–1487 (1975).

Rosenberg et al., "Vectors for selective expression of cloned DNAs by T7 RNA polymerase" *Gene*, 56, pp. 125–135 (1987).

Saiki et al., "A Novel Method for the Detection of Polymorphic Restriction Sites by Cleavage of Oligonucleotide Probes: Application to Sickle–Cell Anemia" *Bio/Technology*, 3:1008–1012 (1985).

Sambrook et al., *Molecular Cloning: A Laboratory Manual* $2^{nd}$ *Ed.*, Cold Spring Harbor Laboratory Press (1989).

Schägger and von Jagow, "Tricine–Sodium Dodecyl Sulfate–Polyacrylamide Gel Electrophoresis for the Separation of Proteins in the Range from 1 to 100 kDa"*Analytical Biochemistry*, 166, pp. 368–379 (1987).

Schwyn and Neilands, "Universal Chemical Assay for the Detection and Determination of Siderophores" *Analytical Biochemistry*, 160, pp. 47–56 (1987).

Sitnikov et al, "Control of cell division in *Escherichia coli*: Regulation of transcription of *ftsQA* involves both*n rpoS* and SdiA–mediated autoinduction" *Proc. Natl. Acad. Sci. USA*, vol. 93, pp. 336–341 Microbiology (1996).

Sizemore et al., "Organization, promoter analysis and transcriptional regulation of the *Staphylococcus xylosus* xylose utilization operon" *Mol Gen Genet*, 227, pp. 337–384 (1991).

Strathern et al., *The Molecular Biology of the Yeast Saccharomyces*, Cold Spring Harbor Laboratory Press (1982).

Surette and Bassler, "Quorum sensing in *Escherichia coli* and *Salmonella typhimurium*" *Proc. Natl. Acad. Sci. USA*, vol. 95, pp. 7046–7050 (1998).

Surette and Bassler, "Regulation of autoinducer production in *Salmonella typhimurium*" *Molecular Microbiology*, 31(2), pp. 585–595 (1999).

Surette et al., "Quorum sensing in *Escherichia coli, Salmonella typhimurium*, and *Vibrio harveyi*: A new family of genes responsible for autoinducer production" *Proc. Natl. Acad. Sci. USA*, vol. 96, pp. 1639–1644 (Feb. 1999).

Walker and Duerre, "S–Adenosylhomocysteine Metabolism in Various Species" *Can. J. Biochem*, vol. 53, pp. 312–319 (1975).

Wang et al., "A factor that positively regulates cell division by activating transcription of the major cluster of essential division genes of *Escherichia coli*" *The EMBO Journal*, vol. 10, No. 11, pp. 3363–3372 (1991).

Yin et al., "Substrate Binding Stabilizes S–Adenosylhomocysteine Hydrolase in a Closed Conformation" *Biochemistry*, 39, pp. 9811–9818 (2000).

\* cited by examiner

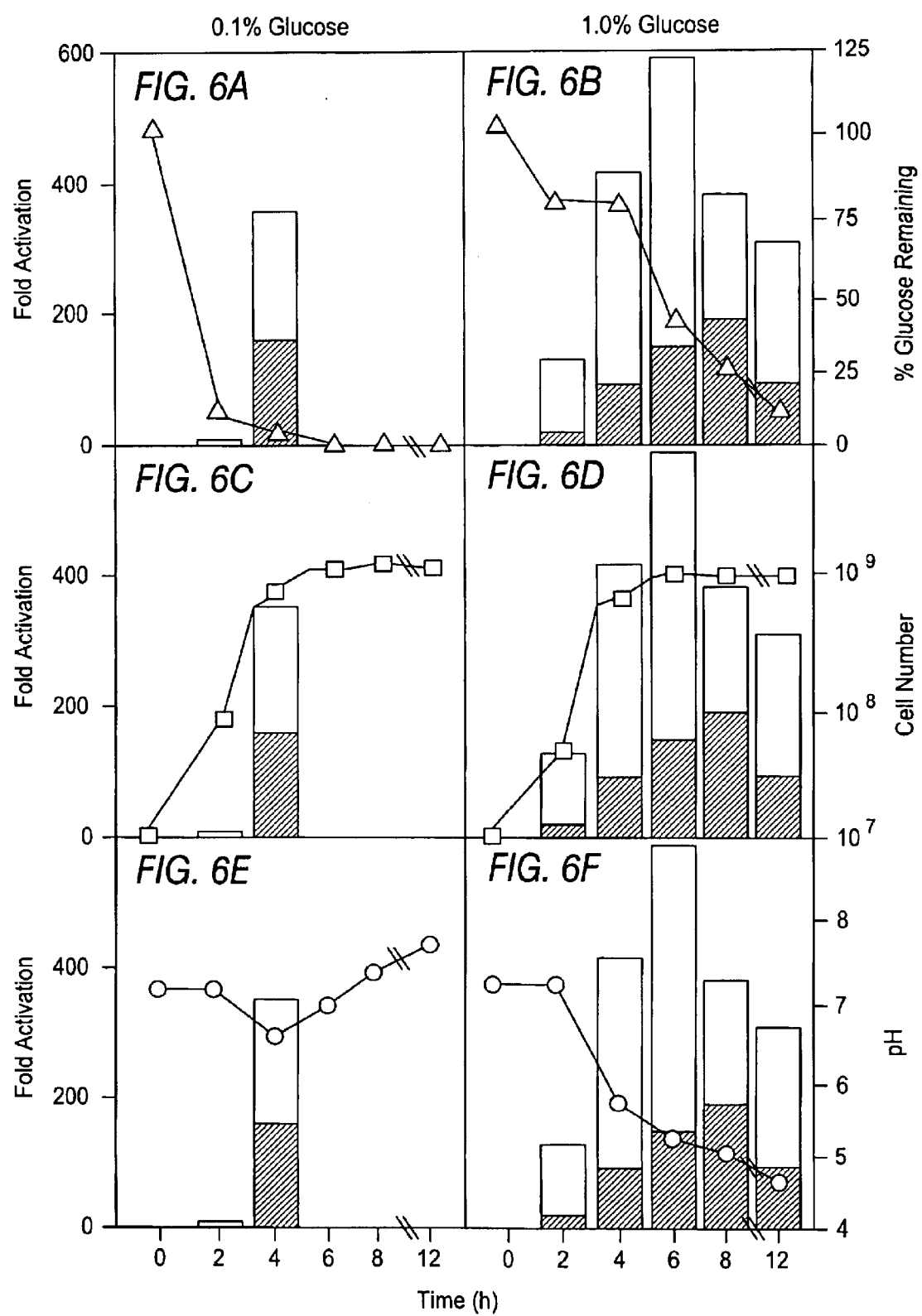

```
V.h. BB120   1  MPLLDSFTVDHTRMMAPAVRVAKTMQTPRGDTITVFDLRFTAPNKDILSEKGIHTLEHLYAGFMRNHLNGDSVIIDISPMGCRTG
E.c. MG1655  1  MPLLDSFTVDHTRMEAPAVRVAKTMQTPMGDAITVFDLRFCVPNLEVMPERGIHTLEHLFAGFMRNHLNGNGVEIIDISPMGCRTG
E.c. O157:H7 1  MPLLDSFTVDHTRMEAPAVRVAKTMQTPMGDAITVFDLRFCVPNLEVMPERGIHTLEHLFAGFMRDHLNGNGVEIIDISPMGCRTG
S.t. LT2     1             NSDHTRMQAPAVRVAKTMQTPMGDAITVFDLRFCIPNKEVMPEKGIHTLEHLFAGFMRDHLNGNGVEIIDISPMGCRTG
E.c. DH5α    1  MPLLDSFTVDHTRMEAPAVRVAKTMQTPMGDAITVFDLRFCVPNLEVMPERGIHTLEHLFAGFMRNHLNGNGVEIIDISPMGCRTG

V.h. BB120   87 FYMSLIGTPSKQQVADAWIAAMEDVLKVENQNKIPELNEYQCGTAAMHSLDEAKQIAKNILEVGVAVNKNDELALPESMLRELRID
E.c. MG1655  87 FYMSLIGTPDKQRVADAWKAAMEDVLKVQDQNQIPELNVYQCGTYQMHSLQEAQDIARSILERDVRINSNEELALPKEKLQELHI
E.c. O157:H7 87 FYMSLIGTPDKQRVADVWKAAMEDVLKVQDQNQIPELNVYQCGTYQMHSLQEAQDIARSILERDVRINSNEELALPKEKLQELHI
S.t. LT2     87 FYMSLIGTPDKQRVADAWKAAMADVLKVQDQNQIPELNVYQCGTYQMHSLSEAQDIARHILERDVRVNSNKELALPKEKLQELHI

E.c. DH5α    87 FYMSLLVRQMSSVLLMPKGKRQWKTC
```

FIG. 12

SEQUENCE LISTING

<160> NUMBER OF SEQ ID NOS: 26

<210> SEQ ID NO 1
<211> LENGTH: 519
<212> TYPE: DNA
<213> ORGANISM: Vibrio harveyi

<400> SEQUENCE: 1

```
atgcctttat tagacagctt taccgtagac cacacgcgta tgaatgcacc agcggttcgt      60
gtggctaaaa cgatgcaaac tccaaaagga gacaccatca cggtattcga cctacgtttc     120
actgctccaa acaaagacat cctttctgag aaaggaattc atacattaga gcatttgtac     180
gcaggcttta tgcgtaatca cctaaatggt gatagcgttg agatcattga tatctcacca     240 atgggtgcc gtactggttt ctacatgagc ttgattggta cgccttcaga gcagcaagtg      300
gctgacgctt ggattgccgc gatggaagac gtactaaaag tagaaaacca aaacaagatc     360
cctgagttga acgaatacca atgtggtaca gcagcgatgc actctctgga tgaagcgaag     420
caaatcgcga gaacattct agaagtgggt gtggcggtga ataagaatga tgaattggca     480
ctgccagagt caatgctgag agagctacgc atcgactaa                             519
```

<210> SEQ ID NO 2
<211> LENGTH: 516
<212> TYPE: DNA
<213> ORGANISM: Escherichia coli

<400> SEQUENCE: 2

```
atgccgttgt tagatagctt cacagtcgat catacccgga tggaagcgcc tgcagttcgg      60
gtggcgaaaa caatgaacac cccgcatggc gacgcaatca ccgtgttcga tctgcgcttc     120
tgcgtgccga acaaagaagt gatgccagaa agagggatcc atacccctgga gcacctgttt     180 gctggtttta tgcgtaacca tcttaacggt aatggtgtag agattatcga tatctcgcca     240
atgggctgcc gcaccggttt ttatatgagt ctgattggta cgccagatga gcagcgtgtt     300
gctgatgcct ggaaagcggc aatggaagac gtgctgaaag tgcaggatca gaatcagatc     360
```

```
ccggaactga acgtctacca gtgtggcact taccagatgc actcgttgca ggaagcgcag    420
gatattgcgc gtagcattct ggaacgtgac gtacgcatca acagcaacga agaactggca    480
ctgccgaaag agaagttgca ggaactgcac atctag                              516

<210> SEQ ID NO 3
<211> LENGTH: 110
<212> TYPE: DNA
<213> ORGANISM: Salmonella typhimurium
<220> FEATURE:
<221> NAME/KEY: misc_feature
<222> LOCATION: (0)...(0)
<223> OTHER INFORMATION: sequence from MudJ

<400> SEQUENCE: 3
gatgtgctga aagtgcagga tcaaaaccag atcccggagc tgaacgttta ccagtgcggt     60
acgtatcaga tgcactcgct cagtgaagcg caggacattg cccgtcatat               110

<210> SEQ ID NO 4
<211> LENGTH: 492
<212> TYPE: DNA
<213> ORGANISM: Salmonella typhimurium
<220> FEATURE:
<221> NAME/KEY: misc_feature
<222> LOCATION: (0)...(0)
<223> OTHER INFORMATION: sequence from alignment;  starts with codon 8
      and requires 3 frameshifts

<400> SEQUENCE: 4
aattcggatc ataccggatg caagcgccgg cggtccgggt tgcaaaaacg atgaacaccc     60
cgcatggcga cgcaatcacg tgtttgatct gcgttttttgc attccgaaca agaagtgat   120 gccggaaaaa gggattcata cgcttgagca tctgtttgct ggctttatgc gcgaccacct   180
caacggtaac ggcgttgaga ttatcgatat ctcgccgatg ggctgccgca ccggcttttta  240 catgagcctg attggcacgc cggacgagca gcgtgttgcc gacgcctgga aagcggcgat   300
ggcggatgtg ctgaaagtgc aggatcaaaa ccagatcccg gagctgaacg tttaccagtg   360
cggtacgtat cagatgcact cgctcagtga agcgcaggac attgcccgtc atattctgga   420
gcgtgatgtg cgcgtgaaca gcaataaaga gctggcgctg ccgaaagaaa aactgcagga   480
actgatattt ag                                                       492

<210> SEQ ID NO 5
<211> LENGTH: 504
<212> TYPE: DNA
<213> ORGANISM: Haemophilus influenzae

<400> SEQUENCE: 5
atgccattac ttgatagttt taaagtggat cacacaaaaa tgaacgcacc tgcagtacgc     60
attgcaaaaa cgatgctcac gccaaaaggc gataatatta ctgtttttga tttacgtttt   120
tgtattccaa acaaagaaat tctttcccca aaaggcattc atacacttga acatttattt   180
gctggattta tgcgcgatca tttaaatggc gatagcatag aaattattga tatttctccg   240
atgggatgtc gcacgggatt ttatatgtct ttgattggca caccaaatga acagaaagtg   300
tctgaggctt ggttagcttc aatgcaagat gttttaggtg tacaagatca agcttctatt   360
cctgaattaa atatctatca atgcggaagc tatacggaac attccttaga agatgcacac   420
gaaattgcca aaaatgttat cgcacgcggt ataggtgtaa ataaaaatga agatttgtca   480
ctcgataatt ccttattaaa atag                                          504
```

```
<210> SEQ ID NO 6
<211> LENGTH: 468
<212> TYPE: DNA
<213> ORGANISM: Helicobacter pylori

<400> SEQUENCE: 6
atgaaaacac caaaaatgaa tgtagagagt tttaatttgg atcacaccaa agtcaaagcc      60
ccttatgtgc gtgtcgctga tcgcaaaaag ggcgttaatg gggatttgat tgtcaaatac     120
gatgtgcgct tcaagcagcc caaccaagat acatggaca tgcctagcct acattcttta     180
gagcatttag tcgctgaaat tatccgcaac catgccagtt atgtcgtgga ttggtcgcct     240
atgggttgcc aaacgggatt ttatctcaca gtgttaaacc atgacaatta cacagagatt     300
ttagaggttt tagaaaagac catgcaagat gtgttaaagg ctacagaagt gcctgccagc     360
aatgaaaagc aatgcggttg ggcggctaac cacactttag agggtgctaa ggatttagcg     420 cgcgctttt tagacaaacg cgctgagtgg tctgaagtgg gggtttga                   468

<210> SEQ ID NO 7
<211> LENGTH: 482
<212> TYPE: DNA
<213> ORGANISM: Bacillus subtilis

<400> SEQUENCE: 7
atgccttcag tagaaagttt tgagcttgat cataatgcgg ttgttgctcc atatgtaaga      60
cattgcggcg tgcataaagt gggaacagac ggcgttgtaa ataaatttga cattcgtttt     120
tgccagccaa ataaacaggc gatgaagcct gacaccattc acacactcga gcatttgctc     180
gcgtttacga ttcgttctca cgctgagaaa tacgatcatt ttgatatcat tgatatttct     240
ccaatgggct gccagacagg ctattatcta gttgtgagcg gagagccgac atcagcggaa     300
atcgttgatc tgcttgaaga cacaatgaag gaagcggtag agattacaga atacctgct      360 gcgaatgaaa agcagtgcgg ccaagcgaag cttcatgatc tggaaggcgc taaacgttta     420
atgcgtttct ggctttcaca ggataaagaa gaattgctaa agtatttggg ctaaaataga     480
aa                                                                   482

<210> SEQ ID NO 8
<211> LENGTH: 537
<212> TYPE: DNA
<213> ORGANISM: Borrelia burdorferi

<400> SEQUENCE: 8
atgaatttga atgggaaaaa ttagattttg taaaaaaaat acaaacagcg ctaaaaaaat      60
gaaaaaaata acaagcttta caatagatca tacaaaactc aaccctggca tatatgtctc     120
aagaaaagat acctttgaaa atgtaatatt tactacaata gacattagaa tcaaagctcc     180
caacatcgaa ccaataattg aaaacgcagc aatacataca atagagcaca taggagctac     240
tttacttaga ataatgaag tttggaccga aaaatagta tattttggcc ctatgggatg     300
cagaactggt ttttacttaa taattttttgg agactatgaa agtaaagatc ttgttgactt     360
agtctcatgg ctttttttccg aaatcgtaaa ttttttcagaa cctatcccag gcgcaagtga     420
taaggaatgc ggaaattaca agaacataa ccttgatatg gctaaatatg aatcttctaa     480
atacttacaa atattaaaca atattaaaga agaaaattta aaatatcctt agctcat        537
```

```
<210> SEQ ID NO 9
<211> LENGTH: 519
<212> TYPE: DNA
<213> ORGANISM: Vibrio cholerae

<400> SEQUENCE: 9
atgccattat tagacagttt taccgtcgat catactcgta tgaatgcacc ggcggtgcgt      60
gttgccaaaa ccatgcaaac cccaaaaggg gatacgatta ccgtatttga tttgcgtttt     120
actatgccaa acaaagatat cttgtctgag cgcggtatcc atactctaga gcatctctac     180
gcgggcttta tgcgcaatca ccttaacggc agccaagtgg agatcatcga tatttcacca     240
atgggttgcc gtacaggttt ctacatgagc ttgattggtg cgccgacaga acagcaagtg     300
gcacaagcat ggctagccgc aatgcaagat gtgttgaaag ttgaaagcca agagcaaatt     360
cctgagctga atgagtacca gtgcggcact gcggcgatgc actcgctcga agaagccaaa     420
gcgattgcga aaacgtgat tgcggcaggc atctcggtta accgtaacga tgagttggcg      480
ctgcccgaat ctatgctcaa tgagctgaag gttcactaa                            519

<210> SEQ ID NO 10
<211> LENGTH: 172
<212> TYPE: PRT
<213> ORGANISM: Vibrio harveyi

<400> SEQUENCE: 10

Met Pro Leu Leu Asp Ser Phe Thr Val Asp His Thr Arg Met Asn Ala
  1               5                  10                  15

Pro Ala Val Arg Val Ala Lys Thr Met Gln Thr Pro Lys Gly Asp Thr
             20                  25                  30

Ile Thr Val Phe Asp Leu Arg Phe Thr Ala Pro Asn Lys Asp Ile Leu
         35                  40                  45

Ser Glu Lys Gly Ile His Thr Leu Glu His Leu Tyr Ala Gly Phe Met
     50                  55                  60

Arg Asn His Leu Asn Gly Asp Ser Val Glu Ile Ile Asp Ile Ser Pro
 65                  70                  75                  80

Met Gly Cys Arg Thr Gly Phe Tyr Met Ser Leu Ile Gly Thr Pro Ser
                 85                  90                  95

Glu Gln Gln Val Ala Asp Ala Trp Ile Ala Ala Met Glu Asp Val Leu
            100                 105                 110

Leu Val Glu Asn Gln Asn Lys Ile Pro Glu Leu Asn Glu Tyr Gln Cys
        115                 120                 125

Gly Thr Ala Ala Met His Ser Leu Asp Glu Ala Lys Gln Ile Ala Lys
    130                 135                 140

Asn Ile Leu Glu Val Gly Val Ala Val Asn Lys Asn Asp Glu Leu Ala
145                 150                 155                 160

Leu Pro Glu Ser Met Leu Arg Glu Leu Arg Ile Asp
                165                 170

<210> SEQ ID NO 11
<211> LENGTH: 171
<212> TYPE: PRT
<213> ORGANISM: Escherichia coli

<400> SEQUENCE: 11

Met Pro Leu Leu Asp Ser Phe Thr Val Asp His Thr Arg Met Glu Ala
  1               5                  10                  15

Pro Ala Val Arg Val Ala Lys Thr Met Asn Thr Pro His Gly Asp Ala
             20                  25                  30
```

-continued

```
Ile Thr Val Phe Asp Leu Arg Phe Cys Val Pro Asn Lys Glu Val Met
         35                  40                  45

Pro Glu Arg Gly Ile His Thr Leu Glu His Leu Phe Ala Gly Phe Met
 50                  55                  60

Arg Asn His Leu Asn Gly Asn Gly Val Glu Ile Ile Asp Ile Ser Pro
 65                  70                  75                  80

Met Gly Cys Ala Thr Gly Phe Tyr Met Ser Leu Ile Gly Thr Pro Asp
                 85                  90                  95

Glu Gln Arg Val Ala Asp Ala Trp Lys Ala Ala Met Glu Asp Val Leu
                100                 105                 110

Lys Val Gln Asp Gln Asn Gln Ile Pro Glu Leu Asn Val Tyr Gln Cys
                115                 120                 125

Gly Thr Tyr Gln Met His Ser Leu Gln Glu Ala Gln Asp Ile Ala Arg
            130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His Ile
                165                 170

<210> SEQ ID NO 12
<211> LENGTH: 164
<212> TYPE: PRT
<213> ORGANISM: Salmonella typhimurium
<220> FEATURE:
<221> NAME/KEY: VARIANT
<222> LOCATION: (0)...(0)
<223> OTHER INFORMATION: starts with residue 8 and has 3 frameshifts

<400> SEQUENCE: 12

Asn Ser Asp His Thr Arg Met Gln Ala Pro Ala Val Arg Val Ala Lys
 1               5                  10                  15

Thr Met Asn Thr Pro His Gly Asp Ala Ile Thr Val Phe Asp Leu Arg
                 20                  25                  30

Phe Cys Ile Pro Asn Lys Glu Val Met Pro Glu Lys Gly Ile His Thr
                 35                  40                  45

Leu Glu His Leu Phe Ala Gly Phe Met Arg Asp His Leu Asn Gly Asn
 50                  55                  60

Gly Val Glu Ile Ile Asp Ile Ser Pro Met Gly Cys Arg Thr Gly Phe
 65                  70                  75                  80

Tyr Met Ser Leu Ile Gly Thr Pro Asp Glu Gln Arg Val Ala Asp Ala
                 85                  90                  95

Trp Leu Ala Ala Met Ala Asp Val Leu Lys Val Gln Asp Gln Asn Gln
                100                 105                 110

Ile Pro Glu Leu Asn Val Tyr Gln Cys Gly Thr Tyr Gln Met His Ser
                115                 120                 125

Leu Ser Glu Ala Gln Asp Ile Ala Arg His Ile Leu Glu Arg Asp Val
            130                 135                 140

Arg Val Asn Ser Asn Lys Glu Leu Ala Leu Pro Lys Glu Lys Leu Gln
145                 150                 155                 160

Glu Thr Asp Ile

<210> SEQ ID NO 13
<211> LENGTH: 167
<212> TYPE: PRT
<213> ORGANISM: Haemophilus influenzae
```

```
<400> SEQUENCE: 13

Met Pro Leu Leu Asp Ser Phe Lys Val Asp His Thr Lys Met Asn Ala
1               5                   10                  15

Pro Ala Val Arg Ile Ala Lys Thr Met Leu Thr Pro Lys Gly Asp Asn
                20                  25                  30

Ile Thr Val Phe Asp Leu Arg Phe Cys Ile Pro Asn Lys Glu Ile Leu
            35                  40                  45

Ser Pro Lys Gly Ile His Thr Leu Glu His Leu Phe Ala Gly Phe Met
        50                  55                  60

Arg Asp His Leu Asn Gly Asp Ser Ile Glu Ile Asp Ile Ser Pro
65                  70                  75                  80

Met Gly Cys Arg Thr Gly Phe Tyr Met Ser Leu Ile Gly Thr Pro Asn
                85                  90                  95

Glu Gln Lys Val Ser Glu Ala Trp Leu Ala Ser Met Gln Asp Val Leu
                100                 105                 110

Gly Val Gln Asp Gln Ala Ser Ile Pro Glu Leu Asn Ile Tyr Gln Cys
            115                 120                 125

Gly Ser Tyr Thr Glu His Ser Leu Glu Asp Ala His Glu Ile Ala Lys
        130                 135                 140

Asn Val Ile Ala Arg Gly Ile Gly Val Asn Lys Asn Glu Asp Leu Ser
145                 150                 155                 160

Leu Asp Asn Ser Leu Leu Lys
                165

<210> SEQ ID NO 14
<211> LENGTH: 155
<212> TYPE: PRT
<213> ORGANISM: Helicobacter pylori

<400> SEQUENCE: 14

Met Lys Thr Pro Lys Met Asn Val Glu Ser Phe Asn Leu Asp His Thr
1               5                   10                  15

Lys Val Lys Ala Pro Tyr Val Arg Val Ala Asp Arg Lys Lys Gly Val
                20                  25                  30

Asn Gly Asp Leu Ile Val Lys Tyr Asp Val Arg Phe Lys Gln Pro Asn
            35                  40                  45

Gln Asp His Met Asp Met Pro Ser Leu His Ser Leu Glu His Leu Val
        50                  55                  60

Ala Glu Ile Ile Arg Asn His Ala Ser Tyr Val Val Asp Trp Ser Pro
65                  70                  75                  80

Met Gly Cys Gln Thr Gly Phe Tyr Leu Thr Val Leu Asn His Asp Asn
                85                  90                  95

Tyr Thr Glu Ile Leu Glu Val Leu Lys Thr Met Gln Asp Val Leu
                100                 105                 110

Lys Ala Thr Glu Val Pro Ala Ser Asn Glu Lys Gln Cys Gly Trp Ala
            115                 120                 125

Ala Asn His Thr Leu Glu Gly Ala Lys Asp Leu Ala Arg Ala Phe Leu
        130                 135                 140

Asp Ile Arg Ala Glu Trp Ser Glu Val Gly Val
145                 150                 155

<210> SEQ ID NO 15
<211> LENGTH: 157
<212> TYPE: PRT
<213> ORGANISM: Bacillus subtilis
```

```
<400> SEQUENCE: 15

Met Pro Ser Val Glu Ser Phe Glu Leu Asp His Asn Ala Val Ala
 1               5                  10                  15

Pro Tyr Val Arg His Cys Gly Val His Lys Val Gly Thr Asp Gly Val
            20                  25                  30

Val Asn Lys Phe Asp Ile Arg Phe Cys Gln Pro Asn Lys Gln Ala Met
         35                  40                  45

Lys Pro Asp Thr Ile His Thr Leu Glu His Leu Leu Ala Phe Thr Ile
 50                  55                  60

Arg Ser His Ala Glu Lys Tyr Asp His Phe Asp Ile Ile Asp Ile Ser
 65                  70                  75                  80

Pro Met Gly Cys Gln Thr Gly Tyr Tyr Leu Val Val Ser Gly Glu Pro
                 85                  90                  95

Thr Ser Ala Glu Ile Val Asp Leu Leu Glu Asp Thr Met Lys Glu Ala
            100                 105                 110

Val Glu Ile Thr Glu Ile Pro Ala Ala Asn Glu Lys Gln Cys Gly Gln
        115                 120                 125

Ala Lys Leu His Asp Leu Glu Gly Ala Lys Arg Leu Met Arg Phe Trp
    130                 135                 140

Leu Ser Gln Asp Lys Glu Glu Leu Leu Lys Val Phe Gly
145                 150                 155

<210> SEQ ID NO 16
<211> LENGTH: 173
<212> TYPE: PRT
<213> ORGANISM: Borrelia burgdorferi

<400> SEQUENCE: 16

Met Gly Lys Ile Arg Phe Cys Lys Lys Asn Thr Asn Ser Ala Lys Lys
 1               5                  10                  15

Met Lys Leu Ile Thr Ser Phe Thr Ile Asp His Thr Lys Leu Asn Pro
            20                  25                  30

Gly Ile Tyr Val Ser Arg Lys Asp Thr Phe Glu Asn Val Ile Phe Thr
         35                  40                  45

Thr Ile Asp Ile Arg Ile Lys Ala Pro Asn Ile Glu Pro Ile Ile Glu
 50                  55                  60

Asn Ala Ala Ile His Thr Ile Glu His Ile Gly Ala Thr Leu Leu Arg
 65                  70                  75                  80

Asn Asn Glu Val Trp Thr Glu Lys Ile Val Tyr Phe Gly Pro Met Gly
                 85                  90                  95

Cys Arg Thr Gly Phe Tyr Leu Ile Ile Phe Gly Asp Tyr Glu Ser Lys
            100                 105                 110

Asp Leu Val Asp Leu Val Ser Trp Leu Phe Ser Glu Ile Val Asn Phe
        115                 120                 125

Ser Glu Pro Ile Pro Gly Ala Ser Asp Lys Glu Cys Gly Asn Tyr Lys
    130                 135                 140

Glu His Asn Leu Asp Met Ala Tyr Glu Ser Ser Lys Leu Tyr Gln
145                 150                 155                 160

Ile Leu Asn Asn Ile Lys Glu Glu Asn Leu Lys Tyr Pro
                165                 170

<210> SEQ ID NO 17
<211> LENGTH: 172
<212> TYPE: PRT
<213> ORGANISM: Vibrio cholerae
```

<400> SEQUENCE: 17

```
Met Pro Leu Leu Asp Ser Phe Thr Val Asp His Thr Arg Met Asn Ala
1               5                   10                  15

Pro Ala Val Arg Val Ala Lys Thr Met Gln Thr Pro Lys Gly Asp Thr
            20                  25                  30

Ile Thr Val Phe Asp Leu Arg Phe Thr Met Pro Asn Lys Asp Ile Leu
        35                  40                  45

Ser Glu Arg Gly Ile His Thr Leu Glu His Leu Tyr Ala Gly Phe Met
50                  55                  60

Arg Asn His Leu Asn Gly Ser Gln Val Glu Ile Ile Asp Ile Ser Pro
65                  70                  75                  80

Met Gly Cys Arg Thr Gly Phe Tyr Met Ser Leu Ile Gly Ala Pro Thr
                85                  90                  95

Glu Gln Gln Val Ala Gln Ala Trp Leu Ala Ala Met Gln Asp Val Leu
            100                 105                 110

Lys Val Glu Ser Gln Glu Gln Ile Pro Glu Leu Asn Glu Tyr Gln Cys
        115                 120                 125

Gly Thr Ala Ala Met His Ser Leu Glu Glu Ala Lys Ala Ile Ala Lys
130                 135                 140

Asn Val Ile Ala Ala Gly Ile Ser Val Asn Arg Asn Asp Glu Leu Ala
145                 150                 155                 160

Leu Pro Glu Ser Met Leu Asn Glu Leu Lys Val His
                165                 170
```

<210> SEQ ID NO 18
<211> LENGTH: 111
<212> TYPE: PRT
<213> ORGANISM: Escherichia coli

<400> SEQUENCE: 18

```
Met Pro Leu Leu Asp Ser Phe Thr Val Asp His Thr Arg Met Glu Ala
1               5                   10                  15

Pro Ala Val Arg Val Ala Lys Thr Met Asn Thr Pro His Gly Asp Ala
            20                  25                  30

Ile Thr Val Phe Asp Leu Arg Phe Cys Val Pro Asn Lys Glu Val Met
        35                  40                  45

Pro Glu Arg Gly Ile His Thr Leu Glu His Leu Phe Ala Gly Phe Met
50                  55                  60

Arg Asn His Leu Asn Gly Asn Gly Val Glu Ile Ile Asp Ile Ser Pro
65                  70                  75                  80

Met Gly Cys Ala Thr Gly Phe Tyr Met Ser Leu Leu Val Arg Gln Met
                85                  90                  95

Ser Ser Val Leu Leu Met Pro Gly Lys Arg Gln Trp Lys Thr Cys
            100                 105                 110
```

<210> SEQ ID NO 19
<211> LENGTH: 32
<212> TYPE: DNA
<213> ORGANISM: Artificial Sequence
<220> FEATURE:
<223> OTHER INFORMATION: Artificial Primer

<400> SEQUENCE: 19
cggagatctg cgctttcaat ggataaacta cg                                    32

```
<210> SEQ ID NO 20
<211> LENGTH: 30
<212> TYPE: DNA
<213> ORGANISM: Artificial Sequence
<220> FEATURE:
<223> OTHER INFORMATION: Artificial Primer

<400> SEQUENCE: 20
cgcggatcct cttcttcgct gtttcgcgtg                                          30

<210> SEQ ID NO 21
<211> LENGTH: 36
<212> TYPE: DNA
<213> ORGANISM: Artificial Sequence
<220> FEATURE:
<223> OTHER INFORMATION: Artificial Primer
<221> NAME/KEY: misc_feature
<222> LOCATION: 30...39
<223> OTHER INFORMATION: n = a,t,g or 6

<400> SEQUENCE: 21
ggccacgcgt cgactagtac nnnnnnnnnn acgccc                                   36

<210> SEQ ID NO 22
<211> LENGTH: 21
<212> TYPE: DNA
<213> ORGANISM: Artificial Sequence
<220> FEATURE:
<223> OTHER INFORMATION: Artificial Primer

<400> SEQUENCE: 22
gcactacagg cttgcaagcc c                                                   21

<210> SEQ ID NO 23
<211> LENGTH: 20
<212> TYPE: DNA
<213> ORGANISM: Artificial Sequence
<220> FEATURE:
<223> OTHER INFORMATION: Artificial Primer

<400> SEQUENCE: 23
ggccacgcgt cgactagtca                                                     20

<210> SEQ ID NO 24
<211> LENGTH: 20
<212> TYPE: DNA
<213> ORGANISM: Artificial Sequence
<220> FEATURE:
<223> OTHER INFORMATION: Artificial Primer

<400> SEQUENCE: 24
tctaatccca tcagatcccg                                                     20

<210> SEQ ID NO 25
<211> LENGTH: 25
<212> TYPE: DNA
<213> ORGANISM: Artificial Sequence
<220> FEATURE:
<223> OTHER INFORMATION: Artificial Primer

<400> SEQUENCE: 25
gtgaagcttg tttactgact agatc                                               25

<210> SEQ ID NO 26
<211> LENGTH: 25
<212> TYPE: DNA
<213> ORGANISM: Artificial Sequence
```

```
<220> FEATURE:
<223> OTHER INFORMATION: Artificial Primer

<400> SEQUENCE: 26
gtgtctagaa aaacacgcct gacag                                              25
```

COMPOSITIONS AND METHODS FOR REGULATING BACTERIAL PATHOGENESIS

CROSS REFERENCE TO RELATED APPLICATIONS

This application claims priority from U.S. Provisional Application Ser. No. 60/110,570, filed Dec. 2, 1998, now abandoned the disclosure of which is incorporated herein by reference.

STATEMENT AS TO FEDERALLY-SPONSORED RESEARCH

Pursuant to 35 U.S.C. §202(c), it is acknowledged that the U.S. Government has certain rights in the invention described herein, which was made in part with funds from the National Science Foundation, Grant No. MCB-9506033.

FIELD OF THE INVENTION

This invention relates to the field of bacterial diseases of humans and other mammals. In particular, the invention provides novel genes and signaling factors involved in inducing pathogenesis in certain bacteria, and methods for controlling such pathogenesis through manipulation of those factors and genes.

BACKGROUND OF THE INVENTION

Several publications are referenced in this application to more fully describe the state of the art to which this invention pertains. The disclosure of each such publication is incorporated by reference herein.

The control of gene expression in response to cell density, or quorum sensing, was first described in the marine luminous bacteria *Vibrio fischeri* and *Vibrio harveyi*. This phenomenon has recently become recognized as a general mechanism for gene regulation in many Gram negative bacteria. Quorum sensing bacteria synthesize, release, and respond to specific acyl-homoserine lactone signaling molecules called autoinducers to control gene expression as a function of cell density. In all acyl-homoserine lactone quorum sensing systems described to date, except that of *V. harveyi*, the autoinducer synthase is encoded by a gene homologous to luxI of *V. fischeri*, and response to the autoinducer is mediated by a transcriptional activator protein encoded by a gene homologous to luxR of *V. fischeri* (Bassler and Silverman, in *Two component Signal Transduction*, Hoch et al., eds, Am. Soc. Microbiol. Washington D.C., pp 431–435, 1995). In contrast, *V. harveyi* has two independent density sensing systems (called Signaling Systems 1 and 2), and each is composed of a sensor-autoinducer pair. *V. harveyi* Signaling System 1 is composed of Sensor 1 and autoinducer 1 (AI-1), and this autoinducer is N-(3-hydroxybutanoyl)-L-homoserine lactone (see Bassler et al., Mol. Microbiol. 9: 773–786, 1993). *V. harveyi* Signaling System 2 is composed of Sensor 2 and autoinducer 2 (AI-2) (Bassler et al., Mol. Microbiol. 13: 273–286, 1994). The structure of AI-2 heretofore has not been determined, nor have the gene(s) involved in biosynthesis of AI-2 been identified. Signaling System 1 is a highly specific system proposed to be used for intra-species communication and Signaling System 2 appears to be less species-selective, and is hypothesized to be for inter-species communication (Bassler et al., J. Bacteriol. 179: 4043–4045, 1997).

Reporter strains of *V. harveyi* have been constructed that are capable of producing light exclusively in response to AI-1 or to AI-2 (Bassler et al., 1993, supra; Bassler et al., 1994, supra). *V. harveyi* reporter strains have been used to demonstrate that a few species of bacteria produce stimulatory substances that mimic the action of AI-2 (Bassler et al., 1997, supra).

Quorum sensing in *V. harveyi*, mediated by Signaling Systems 1 and 2, triggers the organisms to bioluminesce at a certain cell density. These same signaling systems, particularly Signaling System 2, are believed to trigger other physiological changes in *V. harveyi* and other bacteria possessing the same signaling system. Thus, it would be an advance in the art to identify and characterize the signaling factor autoinducer-2 and the genes encoding the proteins required for its production. Such an advance would provide a means to identify a novel class of compounds useful for controlling mammalian enteric or pathogenic bacteria.

SUMMARY OF THE INVENTION

In accordance with the present invention, it has now been discovered that a variety of bacterial species, some of them mammalian pathogens, secrete an organic signaling molecule that stimulates the expression of luminescence in the *V. harveyi* Signaling System 2 bioassay. The molecule secreted by these organisms mimics *V. harveyi* AI-2 in its physical and functional features. The production in bacteria of this novel signaling molecule is regulated by changes in environmental conditions associated with a shift from a free-living existence to a colonizing or pathogenic existence in a host organism. Thus, in addition to stimulating luminescence genes (specifically luxCDABE) in *V. harveyi*, the signaling molecule is expected to stimulate a variety of pathogenesis related genes in the bacterial species that produce it. A highly purified form of the signaling molecule is provided in the present invention. Also provided is a new class of bacterial genes involved in the biosynthesis of the signaling molecule.

According to one aspect, the present invention provides an isolated bacterial extracellular signaling factor comprising at least one molecule that is polar and uncharged, and having an approximate molecular weight of less than 1,000 kDa, wherein said factor interacts with LuxQ protein thereby inducing expression of a *Vibrio harveyi* operon comprising luminescence genes luxCDABE. In a preferred embodiment, the factor possesses a specific activity wherein about 0.1 to 1.0 mg of a preparation of the factor stimulates about a 1,000-fold increase in luminescense, as measured in a bioassay using a *V. harveyi* Sensor 2+ reporter strain. In a particularly preferred embodiment, the factor is purified in such a way that it possesses a specific activity wherein about 1 to 10 µg of a preparation of the factor stimulates about a 1,000-fold increase in luminescence, as measured in a bioassay using a *V. harveyi* Sensor 2+ reporter strain.

The signaling factor of the invention is produced by a variety of bacteria, including but not limited to: *Vibrio harveyi, Vibrio cholerae, Vibrio parahaemolyticus, Vibrio alginolyticus, Pseudomonas phosphoreum, Yersinia enterocolitica, Escherichia coli, Salmonella typhimurium, Haemophilus influenzae, Helicobacter pylori, Bacillus subtilis, Borrelia burgfdorferi, Neisseria meningitidis, Neisseria gonorrhoeae, Yersinia pestis, Campylobacter jejuni, Deinococcus radiodurans, Mycobacterium tuberculosis, Enterococcus faecalis, Streptococcus pneumoniae, Streptococcus pyogenes* and *Staphylococcus aureus*.

In another aspect, the invention provides an isolated bacterial signaling factor having the formula:

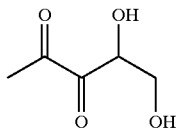

In another aspect, the invention provides a method for identifying a compound that regulates the activity of a signaling factor by contacting the signaling factor with the compound, measuring the activity of the signaling factor in the presence of the compound and comparing the activity of the signaling factor obtained in the presence of the compound to the activity of the signaling factor obtained in the absence of the compound and identifying a compound that regulates the activity of the signaling factor.

In yet another aspect, the invention provides a method for detecting an autoinducer molecule in a sample by contacting the sample with a bacterial cell, or extract thereof, comprising biosynthetic pathways that produce a detectable amount of light in response to an exogenous autoinducer, the bacterial cell having at least two distinct alterations in gene loci that participate in autoinducer pathways, wherein a first alteration in a gene locus comprises an alteration that inhibits detection of a first autoinducer and wherein a second alteration in a gene locus comprises an alteration that inhibits production of a second autoinducer and measuring light produced by the bacterial cell, or extract thereof.

In another aspect, the invention provides a bacterial cell having at least two distinct alterations in gene loci that participate in autoinducer pathways, wherein a first alteration in a gene locus comprises an alteration that inhibits detection of a first autoinducer and wherein a second alteration in a gene locus comprises an alteration that inhibits production of a second autoinducer and wherein the cell is bioluminescent when contacted with an autoinducer.

In another aspect, the invention provides a method for identifying an autoinducer analog that regulates the activity of an autoinducer by contacting a bacterial cell, or extract thereof, comprising biosynthetic pathways which will produce a detectable amount of light in response to an autoinducer with an autoinducer analog and comparing the amount of light produced by the bacterial cell, or extract thereof, in the presence of an autoinducer with the amount produced in the presence of the autoinducer analog, wherein a change in the production of light is indicative of an autoinducer analog that regulates the activity of an autoinducer.

In another aspect, the invention provides a method for producing autoinducer-2 by contacting S-adenosylhomocysteine (SAH) with a LuxS protein under conditions and for such time as to promote the conversion of S-adenosylhomocysteine to autoinducer-2.

In another aspect, the invention provides a method for producing autoinducer-2 by contacting S-ribosylhomocysteine (SRH) with a LuxS protein under conditions and for such time as to promote the conversion of S-ribosylhomocysteine to autoinducer-2.

In another aspect, the invention provides A method for producing autoinducer-2 by contacting S-adenosylhomocysteine (SAH) with a 5'-methylthioadenosine/S-adenosylhomocysteine nucleosidase protein under conditions and for such time as to promote the conversion of S-adenosylhomocysteine to S-ribosylhomocysteine; contacting the above-described S-ribosylhomocysteine with a LuxS protein under conditions and for such time as to promote the conversion of S-ribosylhomocysteine to autoinducer-2.

In another aspect, the invention provides a method for detecting an autoinducer-associated bacterial biomarker by contacting at least one bacterial cell with an autoinducer molecule under conditions and for such time as to promote induction of a bacterial biomarker and detecting the bacterial biomarker.

In another aspect, the invention provides a method for detecting a target compound that binds to a LuxP protein by contacting the LuxP protein with the target compound and detecting binding of the compound to LuxP.

In another aspect, the invention provides a method for regulating bacterial biofilm formation comprising contacting a bacterium capable of biofilm formation with a compound capable of regulating biofilm formation, wherein the compound regulates autoinducer-2 activity.

According to another aspect of the invention, a method is provided for purifying the aforementioned bacterial extracellular signaling factor. The method comprises the steps of: (a) growing, in a culture medium, bacterial cells that produce the signaling molecule; (b) separating the bacterial cells from the culture medium; (c) incubating the bacterial cells in a solution having high osmolarity, under conditions that permit production and secretion of the signaling molecule from the bacterial cells; (d) separating the bacterial cells from the high osmolarity solution; and (e) purifying the factor from the high osmolarity solution. The method may further comprise: (f) separating polar factors from non-polar factors in an evaporated sample of the high osmolarity solution; and (g) subjecting the polar factors to reverse-phase High Performance Liquid Chromatography. In a preferred embodiment, the high osmolarity solution comprises at least 0.4 M monovalent salt, most preferably 0.4–0.5 M NaCl. In another preferred embodiment, the method further comprises growing the bacterial cells in a culture medium containing a carbohydrate selected from the group consisting of glucose, fructose, mannose, glucitol, glucosamine, galactose and arabinose.

According to another aspect of the invention, an isolated nucleic acid molecule is provided, which encodes a protein necessary for biosynthesis of a bacterial extracellular signaling factor that induces expression of a *Vibrio harveyi* LuxQ luminescence gene. The nucleic acid molecule may be isolated from a wide variety of bacteria, including but not limited to: *Vibrio harveyi, Vibrio cholera, Salmonella typhimurium, Escherichia coli, Haemophilus influenzae, Helicobacter pylori, Bacillus subtilis* and *Borrelia burdorferi*.

The aforementioned nucleic acid molecule encodes a protein having between about 150 and 200 amino acid residues. Preferably, the encoded protein comprises an amino acid sequence substantially the same as a sequence selected from the group consisting of any of SEQ ID NOS:10–17, or a consensus sequence derived from a comparison of two or more of SEQ ID NOS: 10–17. The nucleic acid molecule preferably has a sequence substantially the same as a sequence selected from the group consisting of any of SEQ ID NOS:1–9, or a consensus sequence derived from a comparison of two or more of SEQ ID NOS: 1–9.

Recombinant DNA molecules comprising the aforementioned nucleic acid molecules are also provided in accordance with the present invention, as well as proteins produced by expression of any of the nucleic acid molecules.

Additional features and advantages of the present invention will be better understood by reference to the drawings, detailed description and examples that follow.

BRIEF DESCRIPTION OF THE DRAWINGS

FIGS. 6A–F. *S. typhimurium* signaling activity in limiting and non-limiting concentrations of glucose. *S. typhimurium* LT2 was grown in LB in the presence of limiting (0.1%) and non-limiting (1.0%) concentrations of glucose. The activity present in the cell-free culture fluids (black bars) was assayed at the times indicated and normalized to that produced by $1\times10^9$ cells. The increase in signaling activity measured in the 0.4M NaCl osmotic shock fluids prepared from the same cells is shown as the white bars on top of the black bars. These data are also normalized for $1\times10^9$ cells. The signaling activity for limiting glucose is shown in FIGS. 6A, 6C, and 6E, and that for non-limiting glucose is shown in FIGS. 6B, 6D, and 6F. FIGS. 6A and 6B also show the percent glucose remaining (triangles), FIGS. 6C and 6D show the cell number (squares), and Panels E and F show the pH (circles) at each time point.

FIG. 9A shows a restriction map of the *V. harveyi* luxS$_{V.h.}$ chromosomal region which was defined by Tn5 insertion. The sites of Tn5 insertions that disrupted the AI-2 production function and one control Tn5 insertion outside of the luxS$_{V.h.}$ locus are shown (triangles). FIG. 9B depicts the ygaG region in the *E. coli* MG1655 chromosome. This ORF is flanked by the emrB and gshA genes. The direction of transcription of each gene is indicated by the horizontal arrows. The corresponding position of the MudJ insertion that eliminated AI-2 production in *S. typhimurium* LT2 is shown by a vertical arrow. H, R, P, and B denote HindIII, EcoRI, PstI and BamHI restriction sites respectively.

FIG. 10A: AI-2 production phenotypes of the wild type *V. harveyi* strain MM28 which contains a Tn5 insertion outside of luxS$_{V.h.}$ (denoted WT) and the luxS$_{V.h.}$::Tn5 mutant strain MM30 (denoted luxS$^-$). FIG. 10B: AI-2 production phenotypes of wild type *S. typhimurium* LT2 (denoted WT) and the ygaG::MudJ insertion mutant strain CS132 (denoted ygaG$^-$). Activity is reported as fold-induction of luminescence expression of the *V. harveyi* BB170 reporter strain over that when sterile medium was added.

FIG. 11A: AI-2 activity in cell-free fluids from wild type *V. harveyi* BB120, *E. coli* O157:H7, and *S. typhimurium* LT2. FIG. 11B: Complementation of *S. typhimurium* CS132 (ygaG::MudJ) and FIG. 11C: Complementation of *E. coli* DH5. In Panel B and C, the in trans AI-2 production genes are the following: vector control (denoted: none), *E. coli* O157:H7 ygaG; and *V. harveyi* BB120 luxS$_{V.h.}$. *E. coli* and *V. harveyi* are abbreviated E.c. and V.h. respectively.

FIG. 12. Alignment of LuxS and YgaG protein sequences. The translated protein sequences for the AI-2 production family of proteins are shown. We determined the sequences for the luxS$_{v.h.}$ gene from *V. harveyi* BB120 (SEQ ID NO:10), and the ygaG genes (re-named herein as luxS$_{E.C.}$ from *E. coli* MG1655 (SEQ ID NO: 11), *E. coli* O157:H7 (SEQ ID NO: 11), and *E. coli* DH5 (SEQ ID NO: 18). The *S. typhimurium* LT2 ygaG (re-named herein luxS$_{S.T.}$ partial sequence (SEQ ID NO: 12) came from the *S. typhimurium* database. Amino acid residues that are not identical to the LuxS$_{V.H.}$ protein are underlined and not in bold font. The site of the frame shift mutation in the *E. coli* DH5 DNA sequence is denoted by an "*" The 20 altered amino acid residues that are translated following the frame shift are enclosed by the box.

DETAILED DESCRIPTION OF THE INVENTION

Figure 1B:
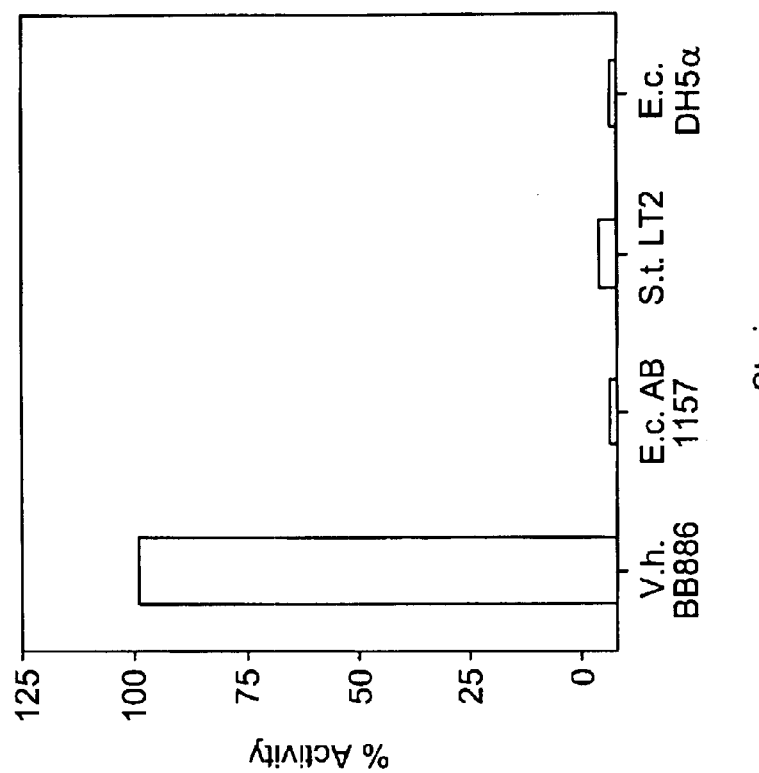
FIGS. 1A–B. Signaling substance from *E. coli* AB1157 and *S. typhimurium* LT2 cell-free culture fluids that induces luminescence in *V. harveyi*. The responses of *V. harveyi* reporter strains BB170 (Sensor 1⁻, Sensor 2⁺) (FIG. 1A), and BB886 (Sensor 1⁺, Sensor 2⁻) (FIG. 1B) to signaling substances present in cell-free culture fluids from *E. coli*, *S. typhimurium* and *V. harveyi* strains are shown. A bright culture of each reporter strain was diluted 1:5000 into fresh medium, and the light production per cell was then measured during the growth of the diluted culture. Cell-free culture fluids or sterile growth medium were added at a final concentration of 10% (v/v) at the start of the experiment. The data for the 5 hour time point are shown and are presented as the percent of the activity obtained when *V. harveyi* cell-free spent culture fluids are added. Abbreviations used for the different strains are: V.h; *Vibrio harveyi*, S.t; *Salmonella typhimurium*, and E.c; *Escherichia coli*.

In accordance with the present invention, we have identified, isolated and characterized an extracellular signaling factor produced by several strains of pathogenic bacteria, including *Salmonella typhimurium* and *Escherichia coli*, which has a role in regulating the pathogenesis or virulence of these bacteria. We have also identified and cloned genes involved in the biosynthesis of this signaling factor. The purification and/or cloning of this signaling molecule and the genes that encode proteins that catalyze its biosynthesis open a new avenue for drug design aimed at either inhibition of production of or response to this molecule by bacteria. Drugs designed to interfere with signaling by this molecule will constitute a new class of antibiotics. The invention further provides methods for detecting an autoinducer and methods for the in vitro production of autoinducr-2.

I. Definitions:

Various terms relating to the biological molecules of the present invention are used throughout the specifications and claims. The terms "substantially the same," "percent similarity" and "percent identity" are defined in detail below.

With reference to the novel signaling factor of the present invention, this molecule is alternatively referred to herein as "signaling factor", "signaling molecule", "autoinducer", and more specifically, "autoinducer-2" or "AI-2". The terms "autoinducer-2" and "AI-2" refer specifically to the signaling factor as produced by *Vibrio harveyi*. The terms "signaling factor" or "signaling molecule", "autoinducer" or "AI-2-like molecule" are intended to refer generally to the signaling factors of the present invention, of which AI-2 is an example.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the factor of interest (e.g., pathogenesis signaling factor, nucleic acid, oligonucleotide, protein, etc.). More preferably, the preparation comprises at least 75% by weight, and most preferably 90–99% by weight, the factor of interest. Purity is measured by methods appropriate for the factor of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "promoter region" refers to the transcriptional regulatory regions of a gene, which may be found at the 5' or 3' side of the coding region, or within the coding region, or within introns.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

The term "operably linked" means that the regulatory sequences necessary for expression of the coding sequence are placed in the DNA molecule in the appropriate positions relative to the coding sequence so as to enable expression of the coding sequence. This same definition is sometimes applied to the arrangement of transcription units and other regulatory elements (e.g., enhancers or translation regulatory sequences) in an expression vector.

II. Description of the Signaling Factor

The invention provides a heterologous bio-assay that has enabled the identification of an extracellular signaling factor produced by *S. typhimurium* and *E. coli*, among other pathogenic bacteria. The factor is sometimes referred to herein as a "pathogenesis signaling" factor or molecule, though it acts as a signal for a variety of physiological changes in bacteria other than pathogenesis. The factor mimics the action of AI-2 (autoinducer-2) of the quorum sensing bacterium *Vibrio harveyi*, and it acts specifically through the *V. harveyi* Signaling System 2 detector, LuxQ.

The signaling factor is a small, soluble, heat labile organic molecule that is involved in intercellular communication in all three bacteria. In *E. coli* and Salmonella, maximal secretion of the molecule occurs in mid-exponential phase and the extracellular activity is degraded as glucose becomes depleted from the medium or by the onset of stationary phase. Destruction of the signaling molecule in stationary phase indicates that, in contrast to other quorum sensing systems, quorum sensing in bacteria that utilize the signaling molecule is critical for regulating behavior in the pre-stationary phase of growth. Protein synthesis is required for degradation of the activity, indicating that a complex regulatory circuitry controls quorum sensing in these enteric bacteria.

Increased signaling activity is observed if, after growing in the presence of glucose, the bacteria are transferred to a high osmolarity (e.g., 0.4M NaCl) or to a low pH (e.g., pH 5.0) environment. Moreover, degradation of the signal is induced by conditions of low osmolarity (e.g., 0.1M NaCl. High osmolarity and low pH are two conditions encountered by pathogenic enteric bacteria, such as *S. typhimurium* and *E. coli*, when they undergo the transition to a pathogenic existence inside a host organism. Thus, quorum sensing in these bacteria appears to play a role in regulating their virulence, by way of directing the bacteria to undergo the transition between a host-associated (i.e., pathogenic) and a free-living existence.

Other factors that regulate the activity of the signaling molecule are described in greater detail in Example 2. Particularly exemplified is the regulation of the molecule in *S. typhimurium*

The timing of lux induction in the bio-assay and the shape of the response curve of *V. harveyi* to the *S. typhimurium* and *E. coli* signals are indistinguishable from those of *V. harveyi* responding to its own Signaling System 2 inducer, AI-2. Furthermore, each of the signaling molecules from *S. typhimurium, E. coli* and *V. harveyi* can be partially purified according to the same protocol. These results indicate that the signaling molecules from each of the aforementioned organisms are either identical or very closely related. Accordingly, AI-2 from *V. harveyi* is a signaling molecule of the invention, but appears to play a different role in that organism than it does in pathogenic enteric bacteria such as Salmonella and Escherichia.

A. Structure of the AI-2 Signaling Factor

Thus, in another aspect, the invention provides autoinducer-2 (AI-2) signaling factor and derivatives thereof. AI-2 of the invention can be used to regulate bacterial growth in a variety of applications. The present invention provides autoinducer-2 molecules having the structure:

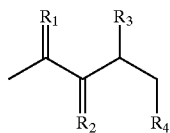

wherein R1, R2, R3 and R4 are independently selected from hydrido, halo, alkyl, haloalkyl, cycloalkyl, cycloalkenyl, heterocyclyl, methyl, cyano, alkoxycarbonyl, amino, carboxyl, hydroxyl, formyl, nitro, fluoro, chloro, bromo, methyl, aryl, heteroaryl, aralkyl, heteroarylalkyl, alkylsulfonyl, haloalkylsulfonyl, arylsulfonyl, heteroarylsulfonyl, hydroxyalkyl, mercaptoalkyl, alkoxyalkyl, aryloxyalkyl, heteroaryloxyalkyl, aralkyloxyalkyl, heteroarylalkyloxyalkyl, alkylthioalkyl, arylthioalkyl, heteroarylthioalkyl, aralkylthioalkyl, heteroarylalkylthioalkyl, haloalkylcarbonyl, haloalkyl (hydroxy)alkyl, alkylcarbonyl, arylcarbonyl, aralkylcarbonyl, heteroarylcarbonyl, heteroarylalkylcarbonyl, carboxyalkyl, alkoxycarbonylalkyl, alkylcarbonyloxyalkyl, aminoalkyl, alkylaminoalkyl, arylaminoalkyl, aralkylaminoalkyl, heteroarylaminoalkyl, heteroarylalkylaminoalkyl, alkoxy, and aryloxy; phenyl, cyclohexyl, cyclohexenyl, benzofuryl, benzodioxolyl, furyl, imidazolyl, thienyl, thiazolyl, pyrrolyl, oxazolyl, isoxazolyl, triazolyl, pyrimidinyl, isoquinolyl, quinolinyl, benzimidazolyl, indolyl, pyrazolyl and pyridyl, aminosulfonyl, fluoro, chloro, bromo, methylthio, methyl, ethyl, isopropyl, tert-butyl, isobutyl, pentyl, hexyl, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, methylcarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, methylenedioxy, ethoxy, propoxy, n-butoxy, hydroxymethyl, hydroxyethyl, methoxymethyl, ethoxymethyl, trifluoromethoxy, methylamino, N,N-dimethylamino, phenylamino, ethoxycarbonylethyl, and methoxycarbonylmethyl, methyl, ethyl, fluoromethyl, difluoromethyl, trifluoromethyl, cyano, methoxycarbonyl, ethoxycarbonyl, tert-butoxycarbonyl, benzyl, phenylethyl, phenylpropyl, methylsulfonyl, phenylsulfonyl, trifluoromethylsulfonyl, hydroxymethyl, hydroxyethyl, methoxymethyl, ethoxymethyl, methylcarbonyl, ethylcarbonyl, trifluoromethylcarbonyl, trifluoro(hydroxy)ethyl, phenylcarbonyl, benzylcarbonyl, methoxycarbonylmethyl, ethoxycarbonylethyl, carboxymethyl, carboxypropyl, methylcarbonyloxymethyl, phenyloxy, phenyloxymethyl, thienyl, furyl, and pyridyl, wherein the thienyl, furyl, pyridyl, methylthio, methylsulfinyl, methyl, ethyl, isopropyl, tert-butyl, isobutyl, pentyl, hexyl, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, methylenedioxy, ethoxy, propoxy, n-butoxy, hydroxymethyl, hydroxyethyl and trifluoromethoxy.

The chemical groups disclosed herein are known to those of skill in the art. For example, as used herein, the term "hydrido" denotes a single hydrogen atom (H). This hydrido radical may be attached, for example, to an oxygen atom to form a hydroxyl radical or two hydrido radicals may be attached to a carbon atom to form a methylene (—CH2—) radical. In addition, alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "halo" means halogens such as fluorine, chlorine, bromine or iodine. The terms "carboxy" or "carboxyl" denotes —CO2H. The term "carbonyl", whether used alone or with other terms, denotes —(S=O)—.

Preferably, the autoinducer-2 molecule of the invention is 4,5-Dihidroxy-2,3-pentanedione having the structure:

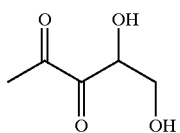

As used herein, an "autoinducer-2 (AI-2)" molecule of the invention includes a molecule that acts as a diffusable sensor for quorum sensing Signaling System 2. For example, AI-2 can regulate gene expression by increasing or decreasing expression of genes associated with pathogenesis of a microorganism. Typically, autoinducer molecules are produced by microorganisms, such as bacteria, during metabolism. For example, the autoinducer-2 (AI-2) molecule of the invention can interact with LuxP which is the protein encoded by the homologue of the luxP gene of pathogenic bacteria such as *V. cholerae, S. typhimurium* and *E. coli*. In turn, the AI-2-LuxP complex can interact with LuxQ which is the protein product encoded by the luxQ gene. The AI-2-LuxP-LuxQ interaction can promote luminescence in bacteria such as Vibrio spp. The AI-2-LuxP-LuxQ interaction has been linked to the activation of biochemical pathways required for bacterial pathogenicity. Thus, the invention provides a method for controlling bacterial gene expression and for regulating bacterial pathogenicity by modulating AI-2-LuxP-LuxQ interactions.

In another aspect, the invention provides methods for using homocysteine as an autoinducer molecule. The structure of homocysteine is as follows:

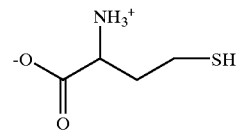

Figure 16:
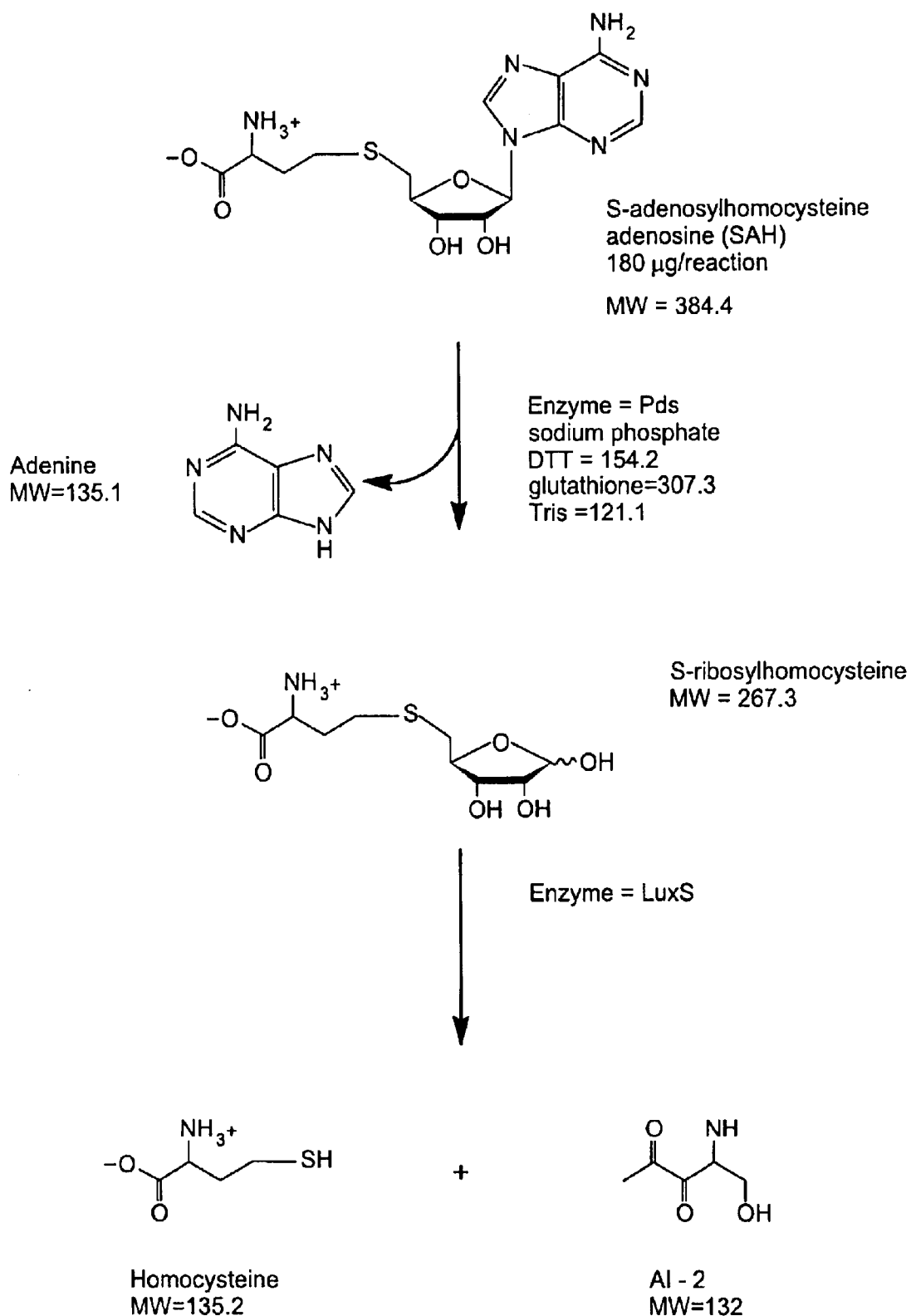
FIG. 16. The structure of AI-2 and the biosynthetic precursors from which AI-2 is derived are shown.

Homocysteine is produced by the activity of the LuxS protein on S-ribosylhomocysteine (FIG. 16). Thus, the invention provides methods for using homoserine as an autoinducer.

The present invention also encompasses optically active isomers of an autoinducer-2 molecule. As used herein, an "isomer" is intended to include molecules having the same molecular formula as an autoinducer-2 molecule of the invention but possessing different chemical and physical properties due to a different arrangement of the atoms in the molecule. Isomers include both optical isomers and structural isomers. As used herein, "optically active" is intended to include molecules that have the ability to rotate a plane of polarized light. An optically active isomer includes the L-isomer and the D-isomer of an autoinducer-2 molecule of the invention.

In addition to optically active isomers, analogs of an autoinducer-2 molecule are included in the invention. As used herein, an AI-2 "analog" is intended to include molecules that are structurally similar but not identical to the claimed autoinducer molecule 4,5-Dihidroxy-2,3-pentanedione. Analogs of AI-2 can include molecules that inhibit rather than stimulate the activity of the LuxP protein. For example, an analog of AI-2 that is capable of a nonproductive interaction with LuxP can be produced. Such a molecule can retain the ability to bind to LuxP, but the analog AI-2-LuxP complex will not be able to productively interact with LuxQ resulting in an inhibition of bacterial pathogenicity. Thus, an AI-2 analog of the invention can act as an inhibitor of bacterial pathogenesis by competing with endogenous AI-2 for binding to LuxP. In addition, an analog of AI-2 can be constructed such the analog AI-2-LuxP complex is capable of nonproductively interacting with LuxQ. In this case, the analog AI-2-LuxP-LuxQ complex is rendered nonfunctional for subsequent biochemical processes such as, for example, transcriptional activation of genes required for pathogenicity. The invention also includes AI-2 analogs which act synergistically to enhance the ability of AI-2 to increase the activity of the LuxP protein.

B. Preparation of the Signaling Factor

Initial strategies for purifying the signaling molecule of the invention resulted in a partially purified preparation comprising the molecule with a specific signaling activity estimated at about 0.1–1.0 mg of the partially purified material stimulating a 1,000-fold increase in luminescence, as measured in the *V. harveyi* bioassay. The signaling activity does not extract quantitatively into organic solvents and it does not bind to either a cation or an anion exchange column. The molecule is a small (less than 1,000 kDa), polar but uncharged organic factor. The activity is acid stable and base labile, and it is heat resistant to 80° C. but not 100° C. These features of the signaling molecule make it clear that the molecule is different from any previously described autoinducer.

The signaling factor of the present invention may be purified from its natural sources, i.e. the bacteria that produce it. With regard to purifying AI-2 from natural sources, altering the culture medium, e.g., by adding glucose or another sugar, by increasing the osmolarity, and/or decreasing pH, can increase production of the signaling molecule in Salmonella and other enteric bacteria, has also enabled purification of the signaling molecule to near-homogeneity. Thus, the molecule has now been highly purified from culture fluids of enteric bacteria (e.g., *E. coli*, *S. typhimurium*) using the following protocol:

1. Grow a culture of the signal producing enteric bacterium overnight in LB containing 0.5% glucose or another sugar (37° C., with aeration). Inoculate fresh LB containing glucose or another sugar at 0.5% with the overnight culture, at a 1:100 dilution. Grow the diluted culture to mid-exponential phase (3.5 h, 37° C., with aeration).
2. Pellet the cells (10,000 rpm, 10 min, 4° C.). Discard the culture medium. Resuspend the cells and wash in 1/10 th the original volume of low osmolarity NaCl solution (0.1M NaCl in water).
3. Pellet the cells again (10,000 rpm, 10 min, 4° C.). Discard the low osmolarity culture fluid. Resuspend the cells in 1/10 th the original volume of high osmolarity NaCl solution (0.4M NaCl in water). Incubate the suspension at 37° C. for 2 h with aeration. During this time, increased production and secretion of the signaling molecule occurs.
4. Pellet the cells (10,000 rpm, 10 min, 4° C.). Collect the supernatant containing the secreted signaling molecule, filter the supernatant through a 0.2 M bacterial filter to remove any remaining cells.
5. Evaporate the aqueous filtrate using a rotary evaporator at 30° C. Extract the dried filtrate in 1/10 th the original volume of chloroform:methanol (70:30).
6. Evaporate the organic extract using a rotary evaporator at room temperature. Re-dissolve the dried extract in methanol at 1/100 th of the original volume.
7. Subject the partially purified signal to High Performance Liquid Chromatography (HPLC), using a preparative reverse phase C18 column. Elute the molecule with a linear gradient of 0–100% acetonitrile in water at 5 ml per minute. Collect 30 fractions, 5 ml each.
8. Assay the HPLC fractions in the *V. harveyi* BB170 AI-2 assay, and pool the active fractions.

The product from the C18 column contains the signaling molecule and a small number of other organic molecules. This highly purified preparation of the signaling molecule has activity 50–100 times greater than that of the partially purified material described above (the preparation of which did not include the high osmoticum step or the final HPLC step), i.e., 1–10 μg material stimulates a 1,000-fold increase in luminescence in the *V. harveyi* bioassay.

Subsequent strategies for purifying the AI-2 signaling molecule have led to the identification of a novel in vitro system for producing AI-2. Thus, in addition to providing a cloned, overexpressed and purified *S. typhimurium* LuxS protein, the present invention also provides a method for producing AI-2 in vitro. The present invention provides a mechanism for generating large quantities of pure AI-2 useful for mass spectral and NMR analysis, and for screening compounds which regulate the activity of AI-2. Moreover, the present invention provides a method for determining the in vivo biosynthetic pathway for AI-2 synthesis. The in vitro method for AI-2 production is described below in Example 5 and FIG. 15. The method provides a novel means for efficiently producing autoinducer molecules for further study. The method also provides a means for producing substantial quantities of AI-2 for use in commercial applications. Such applications include, but are not limited to, adding AI-2 of the invention to a growth media to increase bacterial growth. Such a method is particularly useful in the in the production of antibiotics from cultured bacteria. The addition of AI-2 can increase the antibiotic production of such organisms by promoting cell growth. Preferably, the signaling factor AI-2 is produced by the in vitro method set forth in Example 5 of the disclosure.

C. Uses of the Signaling Factor

The isolated and purified signaling molecules of the present invention are used as targets for the design of compounds that regulate the activity of AI-2. As used herein, "regulate" includes increasing or decreasing the activity of AI-2. As used herein, the "activity" of AI-2 encompasses any aspect of the molecules ability to act as a signaling factor in bacterial quorum sensing. A "compound" can be any agent or composition that effects the activity of AI-2. For example, a compound of the invention can be a nucleic acid, a protein or small molecule. Thus, the invention provides a means for identifying a new class of antibiotics that inhibit the activity of the AI-2 molecule or otherwise block the signaling pathway in which the molecule participates. Such inhibitors may be identified by large-scale screening of a variety of test compounds, using the *V. harveyi* bioassay in the presence of the purified signaling molecule. A reduction in signaling activity in the presence of a test compound would be indicative of the ability of that compound to inhibit the activity of the signaling molecule or to block some other part of the pathogenesis signaling pathway.

Further, the invention provides a basis for the rational design of specific inhibitors or non-functional analogs of AI-2. Such structure-specific inhibitors or analogs may be tested in the *V. harveyi* bioassay for their ability to inhibit the signaling molecule or to block the pathogenesis signaling pathway.

The invention also encompasses methods for identifying naturally produced compounds that inhibit the activity of a signaling molecule such as autoinducer-2. For example, a defensive strategy employed by eucaryotic organisms to avoid bacterial colonization is to specifically target and inhibit quorum sensing controlled functions. Such a mechanism has been identified in *D. pulchra*. Recent studies indicate that halogenated furanones produced by *D. pulchra* inhibit quorum sensing by competing for the homoserine-lactone (HSL) autoinducer-binding site in LuxR. Thus, by providing a novel autoinducer and the cellular components that interact with the autoinducer, the present invention also provides a method to screen naturally produced compounds for their effect on quorum sensing system-2. For example, naturally produced compounds can be screened for their effect on the autoinducer-2-LuxP interaction. Alternatively, such compounds can be screened for their effect on autoinducer-2-LuxP-LuxQ interactions.

It will be appreciated by persons skilled in the art that, now that targets for the signaling molecule have been identified in *E. coli*, inhibition of the *E. coli* target can also be used to screen potential signaling molecule inhibitors or analogs. The inventors have prepared a ler-lacZ reporter fusion construct to be used in testing for reduction of expression of the Type III secretion gene in *E. coli* O157:H7 (pathogenic strain) directly. Furthermore, a similar locus exists in *S. typhimurium*.

Thus, the invention provides a method for selecting inhibitors or synergists of the autoinducer-2 molecule, 4,5-Dihidroxy-2,3-pentanedione. As used herein, an "inhibitor" of AI-2 is intended to include molecules that interfere with the ability of the autoinducer molecule to act as a signal for luminescence or pathogenesis. Inhibitors include molecules that degrade or bind to AI-2. The method comprises contacting the autoinducer molecule with a suspected inhibitor or synergist, measuring the ability of the treated autoinducer molecule to stimulate the activity of a selected gene then determining whether the suspected inhibitor or synergist represses or enhances the activity of the autoinducer molecule. Actual inhibitors and synergists of the autoinducer molecule are then selected. For example, a suspected inhibitor can be mixed with 4,5-Dihidroxy-2,3-pentanedione and the mixture then combined with a reporter strain of *V. harveyi* disclosed herein. The amount of luminescence in the presence of the suspected inhibitor can be compared with a control mixture which does not include the inhibitor. A decrease in luminescence is indicative of AI-2 inhibition. In this manner, compounds that regulate bacterial pathogenesis can be rapidly screened.

In another aspect, the invention also provides methods of selecting inhibitory and synergistic analogs of AI-2. The method comprises mixing a known amount of the autoinducer molecule with a known amount of the suspected inhibitory or synergistic analog, measuring the ability of the treated autoinducer molecule to stimulate the activity of a selected gene then determining whether the suspected inhibitory or synergistic analog represses or enhances the activity of the autoinducer molecule. Actual inhibitory or synergistic analogs of the autoinducer molecule are then selected.

The autoinducer-2 molecule can be purified from the native source using conventional purification techniques, derived synthetically by chemical means, or preferably, produced by the in vitro method of the invention described below. As used herein, "purified from a native source" is intended to include an autoinducer-2 molecule of the above formula that has been manufactured by an organism. "Purified from the native source" includes isolating the autoinducer molecule from the culture media or cytoplasm of bacteria such as *S. typhimurium* using conventional purification techniques. As used herein, "synthesized by chemical means" is intended to include autoinducer molecules of the claimed formula that have been artificially produced outside of an organism. The invention includes an autoinducer of the invention manufactured by a person skilled in the art from chemical precursors using standard chemical synthesis techniques.

The invention further provides methods of inhibiting the infectivity of a pathogenic organism as well as therapeutic compositions containing an AI-2 analog or AI-2 inhibitor of the invention. The methods comprise administering to a subject a therapeutically effective amount of an pharmaceutical composition that is capable of inhibiting the activity of AI-2. As used herein, "inhibiting infectivity" includes methods of affecting the ability of a pathogenic organism to initially infect or further infect a subject that would benefit from such treatment. A pharmaceutical composition of the invention can include, but is not restricted to, an agent that prevents the transcriptional activation of extracellular virulence factors such as exotoxin A and elastolytic proteases. As used herein, an "agent" includes molecules that inhibit the ability of the LuxP protein and LuxQ protein to activate transcription of extracellular virulence factors. Agents include inhibitors that interact directly with AI-2 such that AI-2 is prevented from acting as a sensor for quorum sensing Signaling System-2. Preferably, the agent interacts with 4,5-Dihidroxy-2,3-pentanedione. Agents further include analogs of AI-2 that can compete with 4,5-Dihidroxy-2,3-pentanedione for binding to LuxP or LuxQ.

The invention further provides pharmaceutical compositions for preventing or treating pathogen-associated diseases by targeting factors involved in the Signaling System type-2 pathway. For example, LuxP or LuxQ, or homologues thereof, provide a common target for the development of a vaccine. Antibodies raised to LuxP or LuxQ, or homologues thereof, can inhibit the activation of bacterial pathways associated with virulence. Thus, LuxP and LuxQ provide common antigenic determinants which can be used to immunize a subject against multiple pathogen-associated disease states. For example, the autoinducer Signaling System type-2 is believed to exist in a broad range of bacterial species including bacterial pathogens. As discussed above, the autoinducer-2 signaling factor is believed to be involved in inter-species as well as intra-species communication. In order for the quorum sensing Signaling System type-2 to be effective for inter-species communication, it is likely to be highly conserved among various bacterial species. Thus, challenging a subject with the LuxP or LuxQ polypeptide, or an antigenic fragment thereof, isolated from a particular organism may confer protective immunity to other disease states associated with a different organism. For example, a vaccine developed to the LuxP protein isolated from *V. cholerae* may be capable of cross-reacting with a LuxP homologue expressed by a different organism. Thus, it is envisioned that methods of the present invention can be used to treat pathogen-associated disease states.

Generally, the terms "treating", "treatment", and the like are used herein to mean obtaining a desired pharmacologic and/or physiologic effect. The effect may be prophylactic in terms of completely or partially preventing a spirochete infection or disease or sign or symptom thereof, and/or may be therapeutic in terms of a partial or complete cure for an infection or disease and/or adverse effect attributable to the infection or disease. "Treating" as used herein covers any treatment of (e.g., complete or partial), or prevention of, an infection or disease in a mammal, particularly a human, and includes:

(a) preventing the disease from occurring in a subject that may be predisposed to the disease, but has not yet been diagnosed as having it;

(b) inhibiting the infection or disease, i.e., arresting its development; or (c) relieving or ameliorating the infection or disease, i.e., cause regression of the infection or disease.

Thus, the invention includes various pharmaceutical compositions useful for ameliorating symptoms attributable to a bacterial infection or, alternatively, for inducing a protective immune response to prevent such an infection. For example, a pharmaceutical composition according to the invention can be prepared to include an antibody against, for example, LuxP or LuxQ, a peptide or peptide derivative of LuxP or LuxQ, a LuxP or LuxQ mimetic, or a LuxP or LuxQ-binding agent according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's *The Pharmacological Basis for Therapeutics* (7th ed.).

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science,* 249: 1527, (1990); Gilman et al. (eds.) (1990), each of which is herein incorporated by reference.

As used herein, "administering a therapeutically effective amount" is intended to include methods of giving or applying a pharmaceutical composition of the invention to a subject which allow the composition to perform its intended therapeutic function. The therapeutically effective amounts will vary according to factors such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids and other natural conditions which may inactivate the pharmaceutical composition. The pharmaceutical composition can also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle which contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5 to about 80% of the weight of the unit. The amount of pharmaceutical composition in such therapeutically useful compositions is such that a suitable dosage will be obtained.

The tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the agent, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

As used herein, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the individual to be treated; each unit containing a predetermined quantity of pharmaceutical composition is calculated to produce the desired therapeutic effect in association with the required pharmaceutical carrier. The specification for the novel dosage unit forms of the invention are dictated by and directly dependent on (a) the unique characteristics of the pharmaceutical composition and the particular therapeutic effect to be achieve, and (b) the limitations inherent in the art of compounding such an pharmaceutical composition for the treatment of a pathogenic infection in a subject.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In addition to generating antibodies which bind to antigenic epitopes of proteins of the invention, it is further envisioned that the method of the invention can be used to induce cellular responses, particularly cytotoxic T-lymphocytes (CTLs), to antigenic epitopes of, for example LuxP or LuxQ. Typically, unmodified soluble proteins fail to prime major histocompatibility complex (MHC) class I-restricted CTL responses whereas particulate proteins are extremely immunogenic and have been shown to prime CTL responses in vivo. CTL epitopes and helper epitopes have been identified in proteins from many infectious pathogens. Further, these epitopes can be produced concurrently such that multiple epitopes can be delivered in a form that can prime MHC class I restricted CTL responses. An example of a system that can produce recombinant protein particles carrying one or more epitopes entails the use of the p1 protein of the retrotransposon Ty1 of *Saccharomyces cerevisiae* (Adams, et al., *Nature*, 329:68, 1987). Sequences encoding CTL epitopes can, for example, be fused to the C-terminus of p1 and the resulting Ty virus-like particles (Ty-VLPS) may be able to generate a CTL response. Thus, conserved regions of pathogenic antigens, such as those that are involved in, or result from, the activation of Signaling System type-2, can be identified and incorporated together in a particle which enables the host immune system to mount an effective immune response against multiple spirochetal organisms. Further, the method of the invention can be used to generate particles with multiple epitopes to a single protein, such as LuxP, or multiple epitopes from various proteins.

The method of the invention also includes slow release antigen delivery systems such as microencapsulation of antigens into liposomes. Such systems have been used as an approach to enhance the immunogenicity of proteins without the use of traditional adjuvants. Liposomes in the blood stream are generally taken up by the liver and spleen, and are easily phagocytosed by macrophages. Liposomes also allow co-entrapment of immunomodulatory molecules along with the antigens, so that such molecules may be delivered to the site of antigen encounter, allowing modulation of the immune system towards protective responses.

In another embodiment, the invention provides a method for identifying a compound which binds to a protein of the invention, such as LuxP or LuxQ. The method includes incubating components comprising the compound and LuxP or LuxQ under conditions sufficient to allow the components to interact and measuring the binding of the compound to LuxP or LuxQ. Compounds that bind to LuxP or LuxQ include peptides, peptidomimetics, polypeptides, chemical compounds and biologic agents as described above.

Incubating includes conditions which allow contact between the test compound and LuxP or LuxQ. Contacting includes in solution and in solid phase. The test ligand(s)/compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988). Also included in the screening method of the invention are combinatorial chemistry methods for identifying chemical compounds that bind to LuxP or LuxQ. See, for example, Plunkett and Ellman, "*Combinatorial Chemistry and New Drugs*", *Scientific American*, April, p.69, (1997).

The invention further provides a method for promoting the production of a bacterial product, such as, for example, an antibiotic, by contacting a culture of bacteria with an AI-2 of the invention at a concentration effective to stimulate or promote cellular metabolism, growth or recovery. For example, it is known that antibiotic-producing bacteria only produce an antibiotic at or near the peak of log phase growth. By contacting a culture medium containing such antibiotic-producing bacteria with AI-2 of the invention, production of an antibiotic can be induced at an earlier phase of growth. Thus, AI-2 of the invention provides a method for increasing the amount of antibiotic produced by a culture. "Culture medium", as used herein, is intended to include a substance on which or in which cells grow. The autoinducer molecule can be included in commercially available cell culture media including broths, agar, and gelatin.

The invention further provides a method for identifying factors that degrade or inhibit synthesis autoinducer-2. For example, it is known that autoinducer-1 concentration peaks in mid- to late log phase of a bacterial cell culture. In contrast, autoinducer-2 concentration increases earlier in log phase of bacterial cell culture growth and is present in lower amounts in late log phase and stationary phase. This data indicates that a mechanism exists for the degradation of autoinducer-2 at a specific point in bacterial growth. By providing isolated and purified autoinducer-2, the invention allows for the identification of the mechanism whereby autoinducer-2 levels are controlled. For example, partially purified bacterial extracts can be assayed against isolated autoinducer-2 to identify those fractions which degrade autoinducer-2. Fractions that degrade autoinducer-2 can be further fractionated by techniques known to those skilled in the art until those cellular components involved in autoinducer degradation are isolated.

The present invention also provides a method of regulating the expression of a gene. The method comprises inserting a gene into bacteria chosen for enhancement of gene expression by an agent capable of stimulating the activity of the LuxQ protein and incubating the bacteria with an agent capable of stimulating the activity of the LuxP protein. Thus, the signaling molecule of the invention can also be used in screens for other targets that are regulated by the molecule. Cloned promoter-fusion libraries can be prepared from any species of bacteria and these libraries can be used to identify genes that are induced or repressed by the signaling factor, simply by screening for differences in reporter activity in petri or microtiter plates containing the signaling molecule compared to plates that do not contain the molecule.

In addition, quorum sensing is a major regulator of biofilm control and quorum sensing blockers can therefore be used to prevent and/or inhibit biofilm formation. Also, quorum sensing blockers are effective in removing, or substantially decreasing the amount of, biofilms which have already formed on a surface. Thus, by providing the structure of autoinducer-2 (AI-2), the present invention provides a new approach to identifying compounds which inhibit bacterial infections by regulating biofilm formation.

It is known that quorum sensing blockers can reduce protease production by 50% in some strains of bacteria but the discovery that certain compounds can substantially eliminate protease production imparts clear significant clinical advantages. Furthermore, the unexpected finding that biofilm formation can be inhibited or prevented by quorum sensing blockers leads to the reasonable conclusion that other quorum sensing blockers which are known to exhibit quorum sensing blocking in other systems, such as protease production, will also be effective against biofilm formation.

The compounds of the invention are advantageously used to treat and/or prevent infections, such as those caused by *V. angufflarum* or Aeromonas spp. Examples of this type of infection are vibriosis and furunculosis disease in fish. Inhibition of biofilm formation by the bacteria, optionally together with a reduction or elimination of extracellular protease production, renders the bacteria substantially non-pathogenic. The compounds of the invention may be formulated by conventional methods for use in the treatment and/or prevention of bacterial infection. For example, the compounds may be used as solid or liquid preparations (such as tablets, suspensions or solutions for oral administration or sterile injectable compositions), optionally together with pharmaceutically acceptable diluents, carriers or other additives.

For the treatment of vibriosis or furunculosis disease in fish, the compounds or compositions containing them may be applied directly to the fish or they may be added to the fish's food or water.

In another embodiment, the invention provides a method of removing a biofilm from a surface which comprises treating the surface with a compound of the invention. The surface is preferably the inside of an aqueous liquid distribution system, such as a drinking water distribution system or a supply line connected to a dental air-water system. The removal of biofilms from this type of surface can be particularly difficult to achieve. The compound is preferably applied to the surface as a solution of the compound either alone or together with other materials such as conventional detergents or surfactants.

A further embodiment of the invention is an antibacterial composition comprising a compound of the invention together with a bacteriocidal agent. In the antibacterial compositions, the compound of the invention helps to remove the biofilm whilst the bacteriocidal agent kills the bacteria. The antibacterial composition is preferably in the form of a solution or suspension for spraying and/or wiping on a surface.

In yet another aspect, the invention provides an article coated and/or impregnated with a compound of the invention in order to inhibit and/or prevent biofilm formation thereon. The article is preferably of plastics material with the compound of the invention distributed throughout the material.

III. Description of Nucleic Acids Encoding Proteins Involved in Signaling Factor Biosynthesis In accordance with another aspect of the present invention, we have cloned and characterized the genes responsible for production of the signaling molecule of the invention in *V. harveyi, S. typhimurium* and *E. coli*. These genes encode a novel family of proteins responsible for autoinducer production. We have designated the members of this family of autoinducer production genes as luxS, specifically $luxS_{E.c.}$, $luxS_{S.t.}$, and $luxS_{V.h.}$ for *E. coli, S. typhimurium* and *V. harveyi* respectively.

Mutagenesis of luxS in *V. harveyi, S. typhimurium* and *E. coli* eliminates production of the signaling molecule in all three species of bacteria. *S. typhimurium* could be complemented to full production of the molecule by the introduction of either the *E. coli* O157:H7 $luxS_{E.c.}$ gene or the *V. harveyi* BB120 $luxS_{V.h.}$ gene. These results indicate that both the *E. coli* and *V. harveyi* LuxS proteins can function with *S. typhimurium* cellular components to produce the signaling molecule. *E. coli* DH5 was only partially complemented to production of the signaling molecule by the introduction of either the *E. coli* O157:H7 $luxS_{E.c.}$ or the *V. harveyi* BB120 $luxS_{V.h.}$ gene. Because in trans expression of luxS genes in *E. coli* DH5 did not completely restore signaling molecule production, other biochemical or physiological factors may contribute to signal production.

The regulation of signaling molecule production differs between pathogenic and non-pathogenic strains. For example *E. coli* O157:H7 strains produce AI-2 at 30° and 37° C. with or without glucose while *E. coli* K-12 strains do not produce the molecule in the absence of a preferred carbon source. And, all of the *E. coli* O157 strains tested produce greater signaling activity than do non-pathogenic *E. coli* strains. Likewise, pathogenic *S. typhimurium* 14028 produces significantly more signaling activity than does *S. typhimurium* LT2.

Sequence analysis shows that the LuxS proteins are highly homologous, and complementation data suggest that the proteins can function across species. These results indicate that the enzymatic activity carried out by the LuxS proteins and any other cellular machinery that contributes to synthesis of the signaling molecule are conserved. We did not identify any amino acid sequence motif in the LuxS proteins that is indicative of a particular function. Therefore, the LuxS proteins most likely catalyze one specific enzymatic step in biosynthesis of the signaling molecule. The remainder of the steps involved in signaling molecule biosynthesis could be a consequence of normal intermediary metabolic processes. The luxS genes identified here bear no homology to other genes known to be involved in production of acyl-homoserine lactone autoinducers (luxI-like (Fuqua et al., J. Bacteriol. 176, 269–275, 1994), luxLM-ainS-like (Bassler et al, 1993, supra; Gilson et al, J. Bacteriol. 177, 6946–6951, 1995), further indicating that the signaling molecules of the present invention are novel.

Database analysis of finished and unfinished bacterial genomes reveals that many other species of bacteria possess a gene homologous to luxS from *V. harveyi*, *S. typhimurium* and *E. coli*. The species of bacteria identified and the percent homology/identity (H/I) to the LuxS protein of *V. harveyi* are as follows: *Haemophilus influenzae* (88/72), *Helicobacter pylori* (62/40), *Bacillus subtilis* (58/38), *Borrelia burgfdorferi* (52/32), *Neisseria meningitidis* (89/80), *Neisseria gonorrhoeae* (89/80), *Yersinia pestis* (85/77), *Campylobacter jejuni* (85/74), *Vibrio cholerae* (95/90), *Deinococcus radiodurans* (65/45), *Mycobacterium tuberculosis* (59/41), *Enterococcus faecalis* (60/44), *Streptococcus pneumoniae* (57/36) and *Streptococcus pyogenes* (57/36). As reported earlier (Bassler et al., 1997, supra), a few of these species were tested for production of the signaling molecule. We showed that *V. cholerae* and *Y. enterocolitica* but not *B. subtilis* produced signaling activity. We believe that *B. subtilis* does produce the molecule but the environmental conditions that induce its synthesis have not yet been determined. Furthermore, we believe that all of the species identified in the database analysis produce an AI-2-like molecule.

The nucleotide sequences of the luxS genes from *V. harveyi*, *E. coil* and *S. typhimurium are set forth at the end of the specification as SEQ ID NO:*1, SEQ ID NO:2 and SEQ ID NO:3 and 4, respectively (the sequences read in the 5' to 3' direction). These genes are sometimes referred to herein as "LuxS$_{V.h.}$", "LuxS$_{E.c.}$" and Lux$_{S.t.}$", respectively. The amino acid sequences deduced from SEQ ID NOS: 1–4 are set forth at the end of the specification (and in FIG. 12) as SEQ ID NO: 10, SEQ ID NO:11 and SEQ ID NO:12, respectively. It is believed that SEQ ID NOS:1 and 2 constitate full-length clones, whereas SEQ ID NO:3 and SEQ ID NO:4 do not.

The LuxS genes from *V. harveyi*, *E. coli* and *S. typhimurium* are described in greater detail in Example 3. Although those particular LuxS genes and their encoded proteins are exemplified herein, this invention encompasses LuxS genes and their encoded enzymes from any bacterial species, having the sequence, structural and functional properties of the LuxS-encoded proteins described herein. As mentioned in Example 3, homologous nucleic acid sequences have been identified in a variety of bacterial species, but identity of those sequences as LuxS genes heretofore had not been appreciated. LuxS nucleotide and deduced amino acid sequences from other bacterial species are set forth at the end of the specification as SEQ ID NOS: 5–9 and 13–17, respectively, and include sequences from the following species: *Haemophilus influenzae, Helicobacter pylori, Bacillus subtilis, Borrelia burgdorferi* and *Vibrio cholerae*.

In addition to LuxS homologs from species other than *V. harveyi, E. coli* or *S. typhimurium*, variants and natural mutants of SEQ ID NOS:1–9 are likely to exist within different species or strains of Vibrio, Escherichia and Salmonella (indeed, *E. coli* strain DH5 possesses a nonfunctional mutant form of the gene). Because such variants are expected to possess certain differences in nucleotide and amino acid sequence, this invention provides an isolated LuxS nucleic acid molecule and encoded protein having at least about 50–60% (preferably 60–80%, most preferably over 80%) sequence homology in the coding region with the nucleotide sequences set forth as SEQ ID NOS:1–9, respectively (and, preferably, specifically comprising the coding regions of SEQ ID NOS:1–9), and the amino acid sequence of SEQ ID NOS:10–17. Because of the natural sequence variation likely to exist among these proteins and nucleic acids encoding them, one skilled in the art would expect to find up to about 40–50% sequence variation, while still maintaining the unique properties of the LuxS-encoded proteins of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. the structural characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function. The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the University of Wisconsin, and the parameters used by that program are the parameters intended to be used herein to compare sequence identity and similarity.

A. Preparation of LuxS Nucleic Acid Molecules, Encoded Proteins, and Immunologically Specific Antibodies 1. Nucleic Acid Molecules LuxS Nucleic acid molecules of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the DNAs having SEQ ID NOS:1–9, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Such long double-stranded molecules may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.8 kb double-stranded molecule. A synthetic DNA molecule so constructed may then be cloned and amplified in an appropriate vector.

LuxS Nucleic acids also may be isolated from appropriate biological sources using methods known in the art. In a preferred embodiment, a genomic clone is isolated from a cosmid expression library of an *S. typhimurium* or *E. coli* genome. In another embodiment, a genomic clone is isolated from a cosmid library of another bacterial genome.

In accordance with the present invention, nucleic acids having the appropriate level sequence homology with the protein coding region of any of SEQ ID NOS:1–9 may be identified by using hybridization and washing conditions of appropriate stringency. For example, hybridizations may be performed, according to the method of Sambrook et al., using a hybridization solution comprising: 5×SSC, 5×Denhardt's reagent, 1.0% SDS, 100 g/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology (Sambrook et al., 1989):

$$T_m = 81.5C + 16.6 \text{ Log } [Na+] + 0.41(\% \ G+C) - 0.63 \ (\% \text{ formamide}) - 600/\#bp \text{ in duplex}$$

As an illustration of the above formula, using [N+]=[0.368] and 50% formamide, with GC content of 42% and an average probe size of 200 bases, the $T_m$ is 57C. The $T_m$ of a DNA duplex decreases by 1–1.5C with every 1% decrease in homology. Thus, targets with greater than about 75% sequence identity would be observed using a hybridization temperature of 42C.

Another way to isolate the luxS nucleic acids is to search the publicly available databases for the luxS sequence in the bacterial genome of interest, design PCR primers from the sequence and amplify the gene directly from the chromosome. The PCR product can then be cloned. Alternatively, if the complete sequence of a specific bacterial genome is not available, the sequences set forth in the present invention, or any other luxS sequence, may be used to design degenerate oligonucleotides for PCR amplification and cloning of luxS from the chromosome.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable E. coli host cell.

LuxS nucleic acid molecules of the invention include DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the DNA having SEQ ID NOS:1, 2 or 3. Such oligonucleotides are useful as probes for detecting LuxS genes or transcripts.

2. Proteins and Antibodies

A full-length LuxS gene product of the present invention may be prepared in a variety of ways, according to known methods. The protein may be purified from appropriate sources, e.g., cultured bacteria such as *S. typhimurium, E. coli* or *V. harveyi*.

The availability of full-length LuxS nucleic acid molecules enables production of the encoded protein using in vitro expression methods known in the art. According to a preferred embodiment, the enzyme may be produced by expression in a suitable expression system. For example, part or all of a DNA molecule, such as the DNA having SEQ ID NO:1 or 2, may be inserted into a plasmid vector adapted for expression in a bacterial cell, such as *E. coli*, or a eucaryotic cell, such as *Saccharomyces cerevisiae* or other yeast. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The protein produced by LuxS gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The protein encoded by the LuxS gene of the invention, prepared by one of the aforementioned methods, may be analyzed according to standard procedures. For example, the protein may be subjected to amino acid sequence analysis, according to known methods. The stability and biological activity of the enzyme may be determined according to standard methods, such as by the ability of the protein to catalyze production of the signaling molecule under different conditions.

The present invention also provides antibodies capable of immunospecifically binding to the LuxS-encoded protein of the invention. Polyclonal antibodies may be prepared according to standard methods. In a preferred embodiment, monoclonal antibodies are prepared, which react immunospecifically with various epitopes of the protein. Monoclonal antibodies may be prepared according to general methods of Köhler and Milstein, following standard protocols. Polyclonal or monoclonal antibodies that immunospecifically interact with the LuxS-encoded proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

B. Uses of LuxS Nucleic Acid Molecules, Encoded Protein and Immunologically Specific Antibodies LuxS nucleic acids may be used for a variety of purposes in accordance with the present invention. DNA, RNA, or fragments thereof may be used as probes to detect the presence of and/or expression of LuxS genes. Methods in which LuxS nucleic acids may be utilized as probes for such assays include, but are not limited to: (1) in situ hybridization; (2) Southern hybridization (3) northern hybridization; and (4) assorted amplification reactions such as polymerase chain reactions (PCR).

The LuxS nucleic acids of the invention may also be utilized as probes to identify related genes from other bacteria. As is well known in the art, hybridization stringencies may be adjusted to allow hybridization of nucleic acid probes with complementary sequences of varying degrees of homology.

As described above, LuxS nucleic acids are also used to advantage to produce large quantities of substantially pure encoded protein, or selected portions thereof. It should be noted in this regard that the cloned genes inserted into expression vectors can be used to make large quantities of the signaling molecule itself, from any selected bacterial species, in a recombinant host such as *E. coli* DH5. Specific luxS genes are cloned, a large quantity of the encoded protein produced, thereby producing a large quantity of the specific signaling molecule. This will be particularly useful determining differences in the structures of signaling molecules from different species, if such differences are found to exist. Alternatively, a large quantity of signaling molecule from the species of interest could be made using the cloned gene in an expression vector, and thereafter used in library screens for potential targets in petri plate assays, as described above.

Purified LuxS gene products, or fragments thereof, may be used to produce polyclonal or monoclonal antibodies which also may serve as sensitive detection reagents for the presence and accumulation of those proteins in cultured cells. Recombinant techniques enable expression of fusion proteins containing part or all of a selected LuxS-encoded protein. The full length protein or fragments of the protein may be used to advantage to generate an array of monoclonal or polyclonal antibodies specific for various epitopes of the protein, thereby providing even greater sensitivity for detection of the protein in cells or tissue.

Other uses of the LuxS proteins include overproduction to make a quantity of the LuxS proteins sufficient for crystallization. Solving the crystal structure of the LuxS proteins would enable the exact determination of the LuxS active site for catalysis of production of the signaling molecule. The LuxS crystal structure can therefore be used for computer modeling that would greatly facilitate design of signaling molecule analogs, LuxS inhibitors, and rational drug design in general.

Polyclonal or monoclonal antibodies immunologically specific for a LuxS-encoded protein may be used in a variety of assays designed to detect and quantitate the protein. Such assays include, but are not limited to: (1) flow cytometric analysis; (2) immunochemical localization of a LuxS protein in cells or tissues; and (3) immunoblot analysis (e.g., dot blot, Western blot) of extracts from various cells and tissues. Additionally, as described above, antibodies can be used for purification of the proteins (e.g., affinity column purification, immunoprecipitation).

IV. *Vibrio Harveyi* Screening Strain

Figure 13:
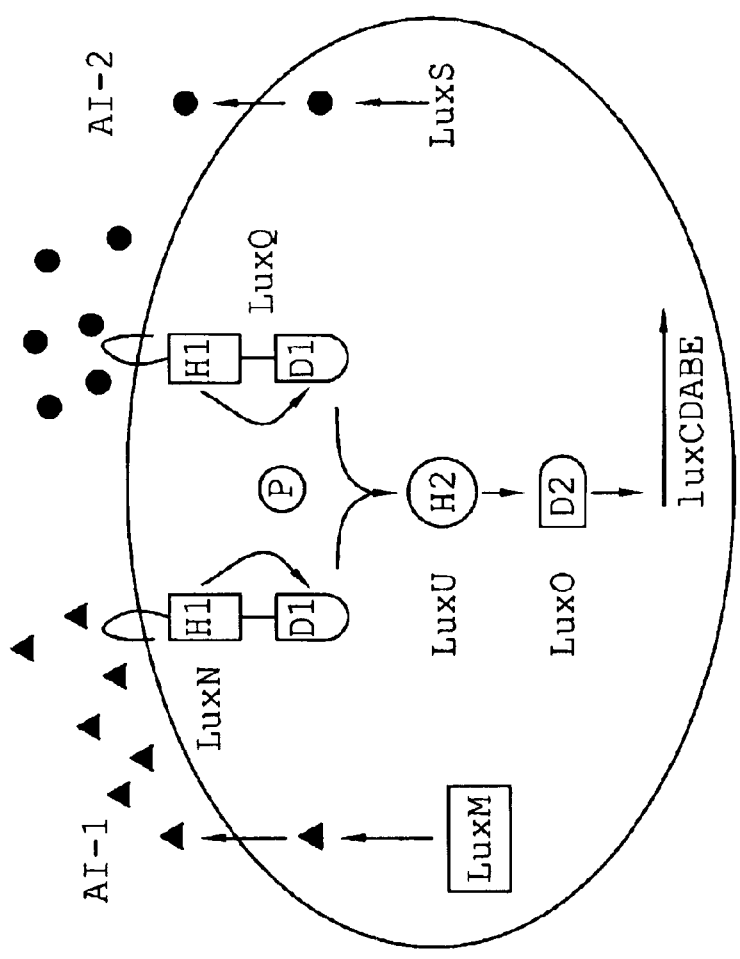
FIG. 13. A diagram of the hybrid quorum sensing circuit of *Vibrio harveyi* is provided. The AI-1 and AI-2 circuits are independently stimulated but integrate their signals for light expression. Each pathway, however, is also independently competent to generate light. This allows for reciprocal mutations in the LuxN or LuxQ sensors to be used to construct a reporter specific for AI-2 or AI-1, respectively.
Figure 14:
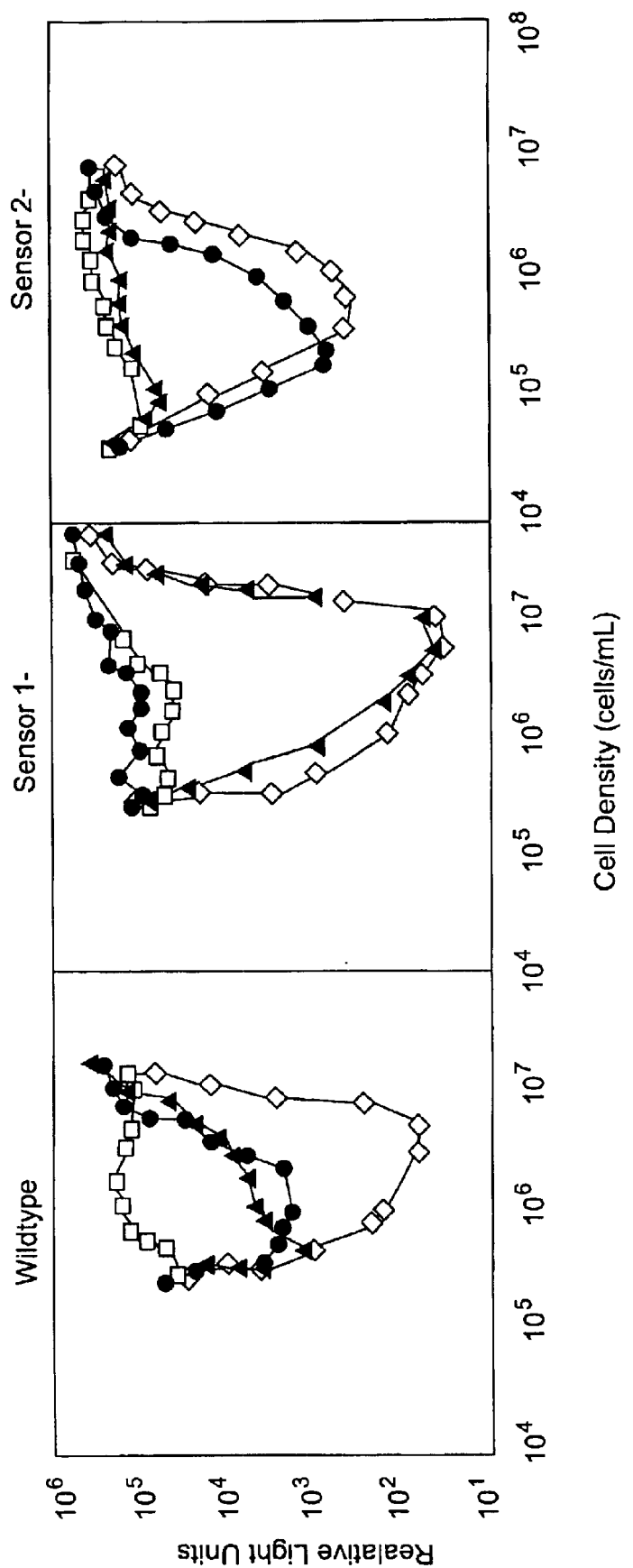
FIG. 14. Response phenotypes of *V. harveyi* wild-type and lux regulatory mutants. At the first time point, cell-free culture fluids (10%), or nothing (N.A) was added. Wild-type, cell-free culture fluid (AI-1+AI2); LuxS-cell-free culture fluid (AI-1); LuxM$^-$ cell-free culture fluid (AI-2). Relative light units are defined as cpm×10$^3$/CFU/ml.

In another aspect, the invention provides a novel strain of *Vibrio Harveyi* having a genotype that is luxN$^-$, luxS$^-$. The The Gram negative bacterium *Vibrio harveyi* contains two parallel quorum sensing circuits which synthesize and detect two different autoinducer molecules (FIG. 13). Circuit 1 synthesizes AI-1 a HSL autoinducer similar in structure to autoinducers synthesized by the LuxI/R pathway found in other gram negative bacteria. Circuit 2 synthesizes AI-2, the structure of which has not been determined. Synthesis of AI-1 and AI-2 is dependent on LuxLM and LuxS respectively. Following the buildup of a critical external concentration of the autoinducers, signaling occurs via a series of a phosphorylation/dephosphorylation reactions. The AI-1 and AI-2 detectors, LuxN and LuxQ respectively, contain both a sensor kinase domain with a conserved histidine (H1) and an attached response regulator domain with a conserved aspartate (D1). Signals from both sensors are channeled to the shared integrator protein LuxU, which is phosphorylated on a histidine residue (H2). Subsequently, the signal is transduced to a conserved aspartate residue (D2) on the response regulator protein LuxO. LuxO-phosphate controls the expression of the luciferase structural operon luxCD-ABE which results in the emission of light. The presence of either AI-1 or AI-2 is sufficient to turn on light production in wild-type *V. harvyi* (strain BB120). For this reason, we have *V. harvyi* strains containing separate mutations in Lux genes L, M, S or Q which are defective in their ability to synthesize or detect AI-1 or AI-2, respectively. AI-2 is detectable using strain BB170 which is sensor 1$^-$, sensor 2$^+$ (LuxN$^-$, LuxQ$^+$). This strain was used to detect AI-2 in diverse bacteria. The light emission response of wild type, LuxN- and LuxQ-phenotypes to increasing cell density is shown in FIG. 14.

BB170 is a sensitive reporter for AI-2, however, the BB170 strain is not optimal for use as a reporter for inhibitors of the quorum pathway in a microtiter based assay. The desired strain is defective in its ability to detect AI-1 (sensor 1$^-$) and defective in its ability to synthesize AI-2. Thus, the invention provides a strain of *V. harveyi* that is genotypically luxN$^-$ and luxS$^-$. The new strain, designated MM32, is useful for identifying inhibitors of the quorum sensing pathway. For example, since the new strain is sensor 1$^-$, its growth or ability to luminesce will not be affected by those organisms producing AI-1. Further, since MM32 is defective for production of AI-2, the addition of exogenous AI-2, or analogs thereof, allows for the rapid identification of inhibitors of AI-2.

In addition, the materials described above are ideally suited for the preparation of a kit. Such a kit may comprise a carrier means being compartmentalized to receive in close confinement one or more container means such as vials, tubes, and the like, each of the container means comprising one of the separate elements to be used in the method.

The container means may comprise a strain of bacteria capable of detecting the presence of an autoinducer. Preferably, the bacterial strain will be capable of providing an easily detectable signal in the presence of autoinducer-2. More preferably, he desired strain is defective in its ability to detect AI-1 (sensor 1$^-$, and defective in its ability to synthesize AI-2. Thus, the kit may provide a strain of *V. harveyi* that is genotypically luxN$^-$ and luxS$^-$ designated MM32. The bacterial strain is useful for identifying autoinducer-2 as well as inhibitors of autoinducer-2 and the quorum sensing pathway.

V. Methods for Detecting a Bacterial Biomarker

Many bacteria presently known to utilize the autoinducer-1 signaling factor associate with higher organisms, i.e., plants and animals, at some point during their lifecycles. For example, *Pseudomonas aeruginosa* is an opportunistic pathogen in humans with cystic fibrosis. *P. aeruginosa* regulates various virulence determinants with AI. Other examples of AI producing bacteria include *Erwinia carotovora, Pseudomonas aureofaciens, Yersinia enterocolitica, Vibrio harveyi,* and *Agrobacterium tumefaciens. E. carotovora* infects certain plants and creates enzymes that degrade the plant's cell walls, resulting in what is called "soft rot disease." *Yersinia enterocolitica* is a bacterium which causes gastrointestinal disease in humans and has been reported to produce an autoinducer. *P.aureofaciens* associates with the roots of plants and produces antibiotics that block fungus growth in the roots. The antibiotic synthesis is under autoinducer control. The present invention provides novel autoinducer-2 and methods of using autoinducer-2. In contrast to autoinducer-1, autoinducer-2 is believed to be an intra-species as well as inter-species signaling factor. Autoinducer-2 is further believed to regulate the expression of pathogenic and virulence factors not regulated by autoinducer-1. Thus, the present invention provides a method to identify and regulate the expression of bacterial biomarkers in, for example, pathogenic bacteria. Methods of the invention can be used to regulate the activity of bacterial pathogens that are present in both plants and animals.

The invention further provides a method for detecting an autoinducer-associated bacterial biomarker by contacting at least one bacterial cell with an autoinducer molecule under conditions and for such time as to promote induction of a bacterial biomarker. As used herein, an "autoinducer-associated bacterial biomarker" is any bacterial cell component which is regulated, modified, enhanced, inhibited or induced in response to an autoinducer. A biomarker can be any bacterial cell component that is identifiable by known microscopial, histological or molecular biological techniques. Such biomarkers can be used, for example, to distinguish pathogenic from non-pathogenic bacteria. Such a biomarker can be, for example, a molecule present on a cell surface, a protein, a nucleic acid, a phosphorylation event or any molecular or morphological characteristic of a bacterial cell that is modified as a result of the bacterium being contacted with an autoinducer. Preferably, the autoinducer is autoinducer-2. The method of the invention is particularly useful for identifying a biomarker which is indicative of bacterial pathogenicity. As previously noted, autoinducers are extracellular signalling factors used by a variety of bacteria to regulate cellular functions in response to various environmental stimuli, including high population density. It is believed that pathogenic bacteria express a biomarker, such as an antigenic determinant, as a result of increased autoinducer concentration in the surrounding environment. Thus, the present invention provides a method for identifying a biomarker by contacting a bacterium with autoinducer-2 and assaying for the presence of the biomarker.

The method of the invention contemplates the use of a probe to identify a biomarker present in a bacterial cell. As used herein, a "probe" can be a nucleic acid, protein, small molecule or antibody useful for detecting a bacterial biomarker present in a sample. The probe can be used in a screening assay to identify a biomarker present in a sample after the sample has been contacted with, for example, an autoinducer. For example, a bacterial biomarker produced by a bacterium following contact with an autoinducer can be identified by contacting a sample containing the bacterium with a probe that binds to the biomarker. Such assays can be used to detect, prognose, diagnose, or monitor various conditions, diseases, and disorders, or monitor the treatment thereof. A probe can be detectably labeled such that the probe is detectable when bound to its target marker. Such means for detectably labeling a probe include a biotin-binding protein, such as avidin or streptavidin, bound to a reporter molecule, such as an enzymatic, fluorescent, or radionuclide label. Other reporter means and labels are well known in the art. In addition, the method of the invention can be used to analyze differential gene expression in a bacterial cell following contact with an autoinducer. For example, where the expression of genes in different cells, normally a cell of interest and a control, is compared and any discrepancies in expression are identified. In such assays, the presence of discrepancies indicates a difference in the classes of genes expressed in the cells being compared. Methods that can be used to carry out the foregoing are commonly known in the art.

The present invention provides a method for identifying a biomarker which can be a protein. For example, a bacterial protein expressed in response to an autoinducer molecule can be detected using the appropriate antibody. The expressed protein can be, for example, an antigenic determinant indicative of a pathogenic bacterium. Antibodies used in the method of the invention are suited for use, for example, in immunoassays for the detection of such a determinant. The term "antibody" as used herein is meant to include intact molecules of polyclonal or monoclonal antibodies, as well as fragments thereof, such as Fab and $F(ab')_2$. For example, monoclonal antibodies are made from antigen containing fragments of a protein by methods well known to those skilled in the art (Kohler, et al., *Nature*, 256:495, 1975).

In addition, the monoclonal antibodies in these immunoassays can be detectably labeled in various ways. For example, radioisotopes may be bound to an immunoglobulin either directly or indirectly by using an intermediate functional group. Intermediate functional groups which often are used to bind radioisotopes which exist as metallic ions to immunoglobulins are the bifunctional chelating agents such as diethylenetriamine-pentacetic acid (DTPA) and ethylene-diaminetetraacetic acid (EDTA) and similar molecules. Typical examples of metallic ions which can be bound to monoclonal antibodies are $^{111}$In, $^{97}$Ru, $^{67}$Ga, $^{68}$Ga, $^{72}$As, $^{89}$Zr, and $^{201}$Tl.

A probe useful in the method of the invention can also be a nucleic acid probe. For example, nucleic acid hybridization techniques are well known in the art and can be used to identify an RNA or DNA biomarker present in a sample containing a bacterium contacted with an autoinducer. Screening procedures which rely on nucleic acid hybridization make it possible to identify a biomarker from any sample, provided the appropriate probe is available. For example, oligonucleotide probes, which can correspond to a part of the sequence encoding a target protein, can be synthesized chemically. The DNA sequence encoding the protein can be deduced from the genetic code, however, the degeneracy of the code must be taken into account. For such screening, hybridization is preferably performed under in vitro or in in vivo conditions known to those skilled in the art.

In addition, the materials described above are ideally suited for the preparation of a kit. Such a kit may comprise a carrier means being compartmentalized to receive in close confinement one or more container means such as vials, tubes, and the like, each of the container means comprising one of the separate elements to be used in the method. A kit of the invention may contain a first container means comprising isolated autoinducer-2. The isolated autoinducer-2 can be used to regulate the expression of a biomarker in a target bacterium. For example, autoinducer-2 can be used to induce expression of a particular biomarker which can then be identified by a probe. Thus, the kit may contain a second container means comprising a probe that can be detectably labeled. The kit may also have a third container comprising a reporter-means, such as a biotin-binding protein, such as avidin or streptavidin, bound to a reporter molecule, such as an enzymatic, fluorescent, or radionuclide label. Other reporter means and labels are well known in the art. For example, the kit of the invention may provide reagents necessary to perform nucleic acid hybridization analysis as described herein or reagents necessary to detect antibody binding to a target.

The following description sets forth the general procedures involved in practicing this aspect of the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1998) (hereinafter "Ausubel et al.") are used.

EXAMPLE 1

Quorum Sensing in *Escherichia coli* and *Salmonella typhimurium*

There have been preliminary indications that *E. coli* senses cell density (Huisman et al., Science 265: 537–539, 1994; Sitnikov et al., Proc. Natl. Acad. Sci. USA 93: 336–341, 1996; Garcia-Lara et al., J. Bacteriol. 178: 2742–2748, 1996). We took advantage of the reduced selectivity of the Signaling System 2 sensor in *V. harveyi* to develop a sensitive assay for detection of extracellular signal molecules produced by *E. coli* and *S. typhimurium*. Using this assay we could determine the conditions under which many strains of *E. coli* and *S. typhimurium* synthesize, secrete, and degrade a signaling substance that will interact with the *V. harveyi* System 2 detector.

Materials and Methods

Preparation of cell-free culture fluids. *E. coli* strains AB1157 and DH5 and *S. typhimurium* strain LT2 were grown at 30° C. overnight with aeration in LB broth containing glucose at the concentrations specified in the text. The following morning fresh LB medium containing the same concentration of glucose used for the overnight growth was inoculated at a 1:100 dilution with the overnight grown cultures. The fresh cultures were grown for various times at 30° C. with aeration. Cell-free culture fluids were prepared by removing the cells from the growth medium by centrifugation at 15,000 rpm for 5 min in a microcentrifuge. The cleared culture fluids were passed through 0.2 m HT Tuffryn filters (Gelman) and stored at −20° C. Cell-free culture fluids containing *V. harveyi* Autoinducer-2 were prepared from *V. harveyi* strain BB152 (Autoinducer 1⁻, Autoinducer 2⁺). *V. harveyi* BB120 (Autoinducer 1⁺, Autoinducer 2⁺) was used to prepare culture fluids containing Autoinducer-1. In both cases, the *V. harveyi* strains were grown overnight at 30° C. with aeration in AB (Autoinducer Bioassay) (Bassler et al., 1993, supra) medium. Cell-free culture fluids from *V. harveyi* were prepared from the overnight culture exactly as described above for *E. coli* and *S. typhimurium*.

Assay for Production of Signaling Molecules.

Cell-free culture fluids from *E. coli*, *S. typhimurium* and *V. harveyi* strains were tested for the presence of signaling substances that could induce luminescence in the *V. harveyi* reporter strain BB170 or BB886. In the assays, 10 l of cell-free culture fluids from *E. coli* AB1157, *E. coli* DH5, and *S. typhimurium* LT2 strains grown and harvested as described above were added to 96-well microtiter dishes. The *V. harveyi* reporter strain BB170 or BB886 was grown for 16 h at 30° C. with aeration in AB medium, diluted 1:5000 into fresh AB medium, and 90 l of the diluted cells were added to the wells containing the *E. coli* and *S. typhimurium* cell-free culture fluids. Positive control wells contained 10 l of cell-free culture fluid from strain *V. harveyi* BB152 (Autoinducer-1⁻, Autoinducer-2⁺) or *V. harveyi* BB120 (Autoinducer-1⁺, Autoinducer-2⁺). Negative control wells contained 10 l of sterile growth medium. The microtiter dishes were shaken in a rotary shaker at 175 rpm at 30° C. Every hour, light production was measured using a Wallac Model 1450 Microbeta Plus liquid scintillation counter in the chemiluminescence mode. The *V. harveyi* cell density was measured by diluting the same aliquots of cells used for measuring luminescence, spreading the dilutions onto solid LM medium (Bassler et al., 1993, supra), incubating the plates overnight at 30C, and counting the resulting colonies the following day.

Preparation of *E. coli* and *S. typhimurium* viable and UV-killed cells for the activity assay. *E. coli* AB1157, *E. coli* DH5 and *S. typhimurium* LT2 cultures were grown for 8 h in LB containing 0.5% glucose at 30° C. with aeration. The cultures were subjected to centrifugation for 5 min at 15,000 rpm in a microcentrifuge and the growth medium was removed from the cell pellets by aspiration. The cell pellets were resuspended in AB medium and washed by vigorous mixing. The cells were again subjected to centrifugation for 5 min at 15,000 rpm. The AB wash medium was removed and discarded and the cells were resuspended in fresh AB medium. Each cell suspension was diluted to give $1 \times 10^6$ cells/10 l, and multiple 10 l aliquots were added to wells of microtiter dishes. Half of the cell aliquots were treated with short wavelength ultraviolet light for 15 min at a distance of 10 cm. This treatment was sufficient to kill all of the cells as judged by plating and incubating the UV-treated cells, and ensuring that no growth occurred by the next day. 90 l of the diluted *V. harveyi* reporter strain BB170 was next added to the wells containing either the viable or dead *E. coli* and *S. typhimurium* cells, and the activity assay was carried out exactly as described in the previous section.

Analysis of glucose in *S. typhimurium* LT2 culture fluids. Glucose concentrations were determined in cell-free culture fluids prepared from *S. typhimurium* using a Trinder assay (Diagnostic Chemicals Ltd.) according to the recommendations of the manufacturer, except that the glucose standards were prepared in LB medium. The assay was sensitive to less than 0.002% glucose. No interfering substances were present in LB medium or spent LB culture fluids.

Results and Discussion

*E. coli* AB1157 and *S. typhimurium* LT2 produce a signaling substance that specifically induces one of the two quorum sensing systems of *V. harveyi*. The *V. harveyi* reporter strain BB170 has the quorum sensing phenotype Sensor 1⁻, Sensor 2⁺. It induces lux expression in response to extracellular signals that act exclusively through the Signaling System 2 detector. Addition of 10% cell-free spent culture fluid prepared from *V. harveyi* strain BB152 (which contains the System 2 autoinducer) stimulates the reporter strain roughly 1000-fold over the endogenous level of luminescence expression. In FIG. 1, the light production by *V. harveyi* BB170 induced by the addition of 10% cell-free spent culture fluids is normalized to 100% activity.

Figure 1A:
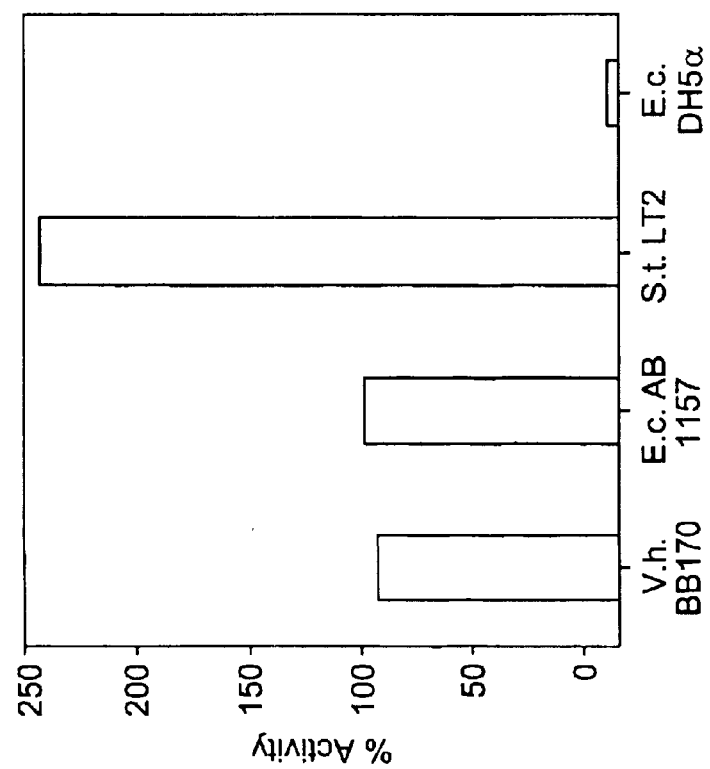

*E. coli* strain AB1157 and *S. typhimurium* strain LT2 were grown for 8 h in LB broth or LB broth containing 0.5% glucose. The *E. coli* and *S. typhimurium* cells were removed from the growth medium and the cell-free culture fluids were prepared and assayed for an activity that could induce luminescence expression in *V. harveyi*. Addition of 10% cell-free culture fluid from *S. typhimurium* LT2 or *E. coli* AB1157 grown in LB containing glucose maximally induced luminescence in the reporter strain BB170, similar to culture fluids from *V. harveyi* BB152 (FIG. 1A). Specifically, *E. coli* AB1157 produced 106% and *S. typhimurium* produced 237% of the *V. harveyi* BB1S2 activity. When the *E. coli* and *S. typhimurium* were grown in LB without added glucose they did not produce the signaling factor. Substitution of 10% (v/v) of LB medium containing 0.5% glucose did not stimulate luminescence in the reporter strain, indicating that there is no substance in the LB-glucose growth medium that induces luminescence expression in *V. harveyi*. We tested obvious candidates for the signal including glucose, amino acids, cAMP, acetate, homoserine lactone, -ketoglutarate and other keto acids that are known to be excreted. None of these compounds has activity. These results suggest that *V. harveyi* BB170 can respond to some substance secreted by *E. coli* AB1157 and *S. typhimurium* LT2 when they are grown on LB containing glucose.

Analogous experiments were performed with the *V. harveyi* reporter strain BB886 (Sensor 1⁺, Sensor 2⁻). *V. harveyi*

BB886 is defective in its response to signaling molecules that act through the Signaling System 2 detector, but it is an otherwise wild type strain (Bassler et al., Mol. Microbiol. 13: 273–286, 1994). FIG. 1B shows the normalized 100% activation of V. harveyi BB886 by cell-free spent culture fluids prepared from V. harveyi BB120. V. harveyi BB120 produces the System 1 autoinducer N-(3-hydroxybutanoyl)-L-homoserine lactone (Bassler et al., 1993, supra). Addition of S. typhimurium LT2 and E. coli AB1157 cell-free culture fluids to V. harveyi strain BB886 caused a 5% and a 1% increase above the control level (FIG. 1B). Together the results of FIGS. 1A and 1B show that the signaling molecule produced by E. coli and S. typhimurium must act specifically through V. harveyi Signaling System 2 and not some other, unidentified pathway.

Figure 2:
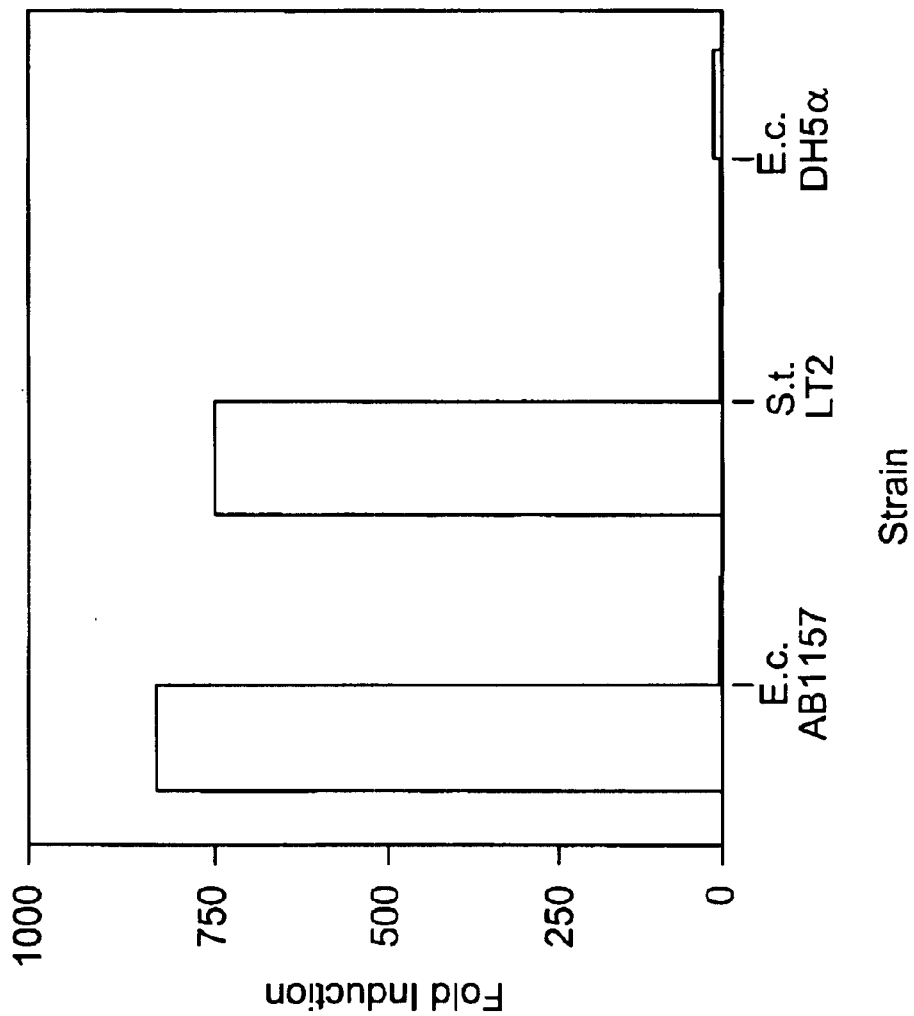
FIG. 2. Active secretion of the signaling molecule by viable *E. coli* and *S. typhimurium*. The response of the *V. harveyi* reporter strain BB170 (Sensor 1⁻, Sensor 2⁺) to a signaling substance produced and secreted by *E. coli* AB1157 and *S. typhimurium* LT2 but not *E. coli* DH5 is shown. *V. harveyi* reporter strain BB170 was diluted 1:5000 in AB medium and light output per cell was monitored during growth. At the start of the experiment, either $1\times10^6$ *E. coli* AB1157, *S. typhimurium* LT2 or *E. coli* DH5 washed and resuspended viable cells (left-hand, white bars) or UV-killed cells (right-hand, black bars) was added. The data are presented as the fold-activation above the endogenous level of luminescence expressed by *V. harveyi* BB170 at the 5 hour time point. Abbreviations used for the different strains are: S.t; *Salmonella typhimurium*, and E.c; *Escherichia coli*.

Viable E. coli AB1157 and S. typhimurium LT2 are required for secretion of the signaling molecule. We considered the possibility that growth of E. coli AB1157 and S. typhimurium LT2 in LB medium containing glucose simply allowed them to utilize and therefore remove some pre-existing inhibitor of induction of luminescence. To show that the cells themselves produce the soluble signaling factor, we added washed E. coli and S. typhimurium cells directly to the luminescence assay. These results are presented in FIG. 2. In this experiment, E. coli AB1157 and S. typhimurium LT2 were grown for 8 h in LB containing 0.5% glucose; the conditions for maximal production of the signaling factor. The cells were removed from the LB-glucose growth medium by centrifugation, and sterile V. harveyi luminescence assay medium was used to wash and resuspend the cell pellets. $1 \times 10^6$ E. coli AB1157 or S. typhimurium LT2 cells were added to the diluted V. harveyi BB170 culture at the start of the experiment. In FIG. 2, the left-hand bar in each series shows that the presence of washed E. coli AB1157 or S. typhimurium LT2 cells is sufficient to fully induce luminescence in V. harveyi BB170. E. coli AB1157 and S. typhimurium LT2 stimulated lux expression in V. harveyi BB170 821-fold and 766-fold respectively. Identical aliquots of the washed E. coli or S. typhimurium cells were killed with short wave ultraviolet light prior to addition to the assay. When dead cells were included in the assay, no stimulation of luminescence occurred. In FIG. 2, these results are shown in the right-hand bar for each strain. Taken together, the results show that the stimulatory factor is produced by the E. coli AB1157 and S. typhimurium LT2 cells themselves during the time course of the experiment; the factor could not have come from the medium in which the cells had been grown. This factor is actively released into the medium by E. coli and S. typhimurium because dead cells have no activity.

E. coli DH5 does not produce the signaling activity. Clinical isolates of E. coli and Salmonella also produce the signaling compound. Ten clinical isolates of Salmonella and five pathogenic isolates of E. coli O157 were assayed and all produced the activity. It was conceivable that the signal was some normal byproduct of glucose metabolism that simply diffuses out of the cells. This is not the case however, because we show that E. coli DH5, which is equally capable of utilizing glucose as E. coli AB1157 and S. typhimurium LT2, does not produce the signaling activity. FIG. 1A demonstrates that unlike E. coli AB1157 and S. typhimurium LT2, the addition of 10% cell-free culture fluid prepared from E. coli DH5 grown 8 h in LB containing 0.5% glucose does not stimulate light production in V. harveyi BB170. Similarly, inclusion of washed viable or killed E. coli DH5 cells in the luminescence assay does not stimulate V. harveyi BB170 to produce light (FIG. 2). The inability of E. coli DH5 to produce the activity indicates that this highly domesticated strain lacks the gene or genes necessary for either the production or the export of the signaling activity. We assayed other laboratory strains of E. coli for the signaling activity (Table 1). Only E. coli DH5 was completely defective in producing the extracellular signal.

TABLE 1

| Species and Strain | Induction of luminescence (%) |
|---|---|
| V. harveyi | |
| V. harveyi BB152 | 100 |
| Salmonella | |
| S. typhimurium LT2 | 237 |
| E. coli | |
| E. coli AB1157 | 106 |
| E. coli DH5 | 5 |
| E. coli JM109 | 76 |
| E. coli MG1655 | 100 |
| E. coli MC4100 | 93 |

The induction of luminescence in V. harveyi reporter strain BB170 by cell-free culture fluids from V. harveyi, S. typhimurium and E. coli is shown. Cell-free culture fluids were prepared from various strains of V. harveyi, S. typhimurium and E. coli as described and tested for production of a signaling substance that could stimulate light production in the reporter strain V. harveyi BB170. The level of V. harveyi stimulation was normalized to 100%. The data for the 5 h time point are shown.

Glucose regulates the production and degradation of the signaling factor by S. typhimurium LT2. Cell-free culture fluids from S. typhimurium LT2 and E. coli AB1157 cells grown in LB without added glucose did not stimulate the expression of luminescence in the reporter strain, indicating that metabolism of glucose is necessary for the production of the signal. We tested other carbohydrates, and in general, growth in the presence of PTS sugars (see Postma et al., in Escherichia coli and Salmonella Cellular and Molecular Biology, (F. C. Niehardt, ed), Am. Soc. Microbiol., Washington D.C., pp. 1149–1174, 1996) enabled E. coli AB1157 and S. typhimurium LT2 to produce the signal. Of the sugars tested, growth on glucose induced the synthesis of the highest level of activity. Growth on other carbon sources, for example TCA cycle intermediates and glycerol, did not induce significant production of the signaling activity.

Figures 3A, 3B:
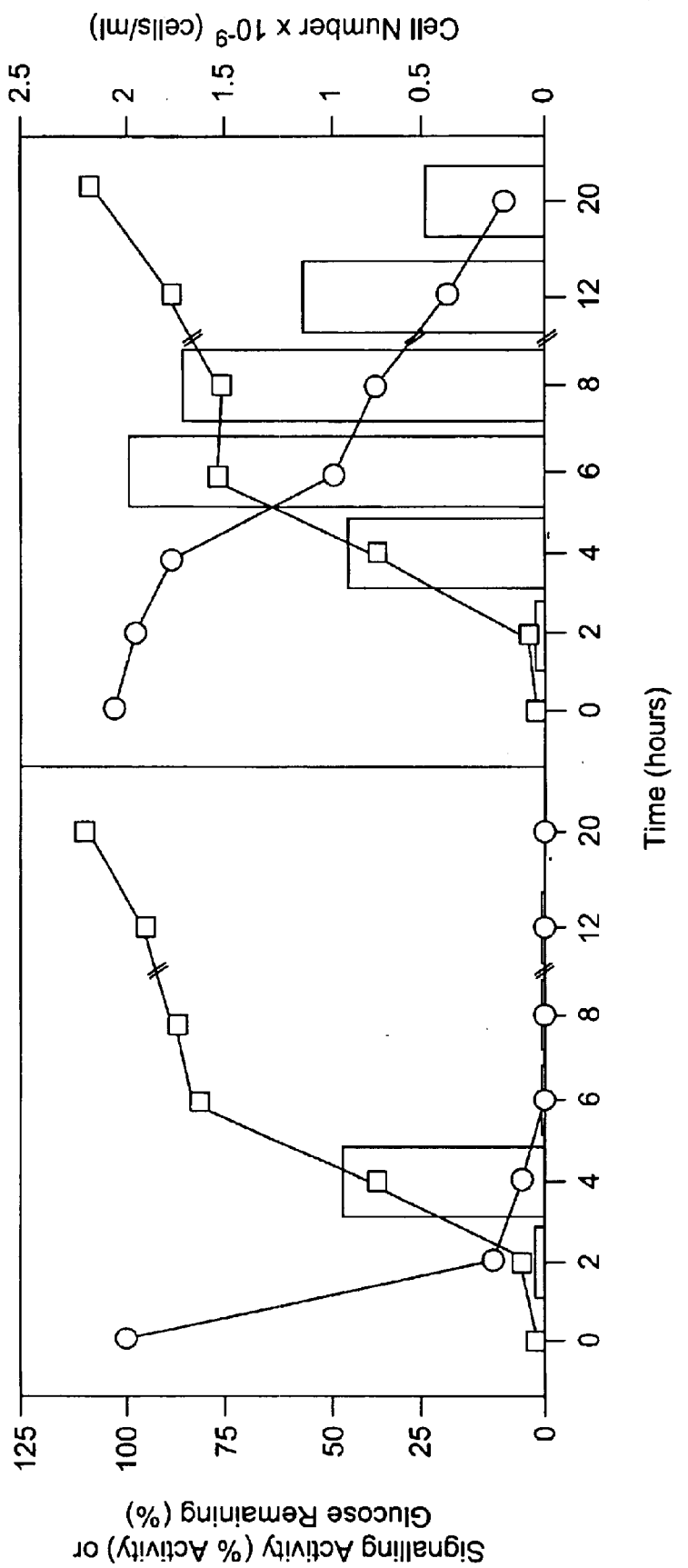
FIGS. 3A–B. Effect of glucose depletion on the production and degradation of the signaling activity by *S. typhimurium* LT2. *S. typhimurium* LT2 was grown in LB medium containing either 0.1% glucose (FIG. 3A) or 0.5% glucose (FIG. 3B). At the specified times cell-free culture fluids were prepared and assayed for signaling activity in the luminescence stimulation assay (Bars), and the concentration of glucose remaining (circles). The cell number was determined at each time by diluting and plating the *S. typhimurium* LT2 on LB medium and counting colonies the next day (squares). The signaling activity is presented as the percent of the activity obtained when *V. harveyi* cell-free spent culture fluids are added. These data correspond to the 5 h time point in the luminescence stimulation assay. The glucose concentration is shown as % glucose remaining. Cell number is cells/ml$\times10^{-9}$. The symbol \\ indicates that the time axis is not drawn to scale after 8 h.

We tested whether the presence of glucose was required for the cells to continue to produce the signal. FIG. 3 shows results with S. typhimurium LT2 grown in LB containing limiting (0.1%) and non-limiting (0.5%) glucose concentrations. FIG. 3A shows that when glucose is limiting, S. typhimurium LT2 produces the signal in mid-exponential phase (after 4 h growth), but stops producing the signaling activity once glucose is depleted from the medium. FIG. 3B shows that when glucose does not become limiting, S. typhimurium LT2 produces greater total activity and continues to produce the signaling activity throughout exponential phase, with maximal activity at 6 h growth. Furthermore, the Figure also shows that the signaling activity synthesized by mid-exponential phase cells is degraded by the time the cells reach stationary phase. In conditions of limiting glucose, no activity remained at stationary phase, and when glucose was plentiful, only 24% of the activity remained. Increasing the concentration of glucose in the growth medium did not change these results, i.e., the activity was secreted during mid-exponential growth and severely reduced activity remained in the spent culture fluids by stationary phase.

In sum, the results presented in this example show that E. coli and S. typhimurium produce a signaling substance that stimulates one specific quorum sensing system in V. harveyi.

Many other bacteria have previously been assayed for such an activity, and only rarely were species identified that are positive for production of this factor (Bassler et al., 1997, supra). Furthermore, as shown here, the *E. coli* and *S. typhimurium* signal is potent, these bacteria make activity equal to that of *V. harveyi*. The degradation of the *E. coli* and *S. typhimurium* signal prior to stationary phase indicates that quorum sensing in these bacteria is tuned to low cell densities, suggesting that quorum sensing in *E. coli* and *S. typhimurium* is modulated so that the response to the signal does not persist into stationary phase. Additionally, quorum sensing in *E. coli* and *S. typhimurium* is influenced by several environmental factors. The production and the degradation of the signal are sensitive not only to growth phase but also to the metabolic activity of the cells. These results indicate that the quorum sensing signal in *E. coli* and *S. typhimurium* has two functions; it allows the cells to communicate to one another their growth phase and also the metabolic potential of the environment.

Understanding the regulation of quorum sensing in *E. coli* and *S. typhimurium* is important for understanding community structure and cell-cell interactions in pathogenesis. In the wild, pathogenic *E. coli* and *S. typhimurium* may never reach stationary phase because dispersion is critical. It is therefore appropriate that quorum sensing in *E. coli* and *S. typhimurium* should be functioning at low cell density. This situation is in contrast to that of *V. fischeri*, the luminescent marine symbiont, where the quorum sensing system is only operational at high cell densities; cell densities indicative of existence inside the specialized light organ of the host. The specific quorum sensing systems of *V. fischeri* and *E. coli* and *S. typhimurium* appear appropriately regulated for the niche in which each organism exists. In both cases, quorum sensing could be useful for communicating that the bacteria reside in the host, not free-living in the environment. Additional complexity exists in the *E. coli* and *S. typhimurium* systems because these bacteria channel both cell density information and metabolic cues into the quorum sensing circuit. Again, signals relaying information regarding the abundance of glucose or other metabolites could communicate to the bacteria that they should undergo the transition from a free-living mode to the mode of existence inside the host.

Under all the conditions we have tested, the signaling activity described in this example does not extract quantitatively into organic solvents and it does not bind to either a cation or anion exchange column. Preliminary characterization indicates that the signal is a small (less than 1000 MW) polar but apparently uncharged organic compound. The activity is acid stabile and base labile, it is heat resistant to 80 but not 100° C. Purification of the *E. coli, S. typhimurium* and *V. harveyi* signal is described in greater detail in the following examples.

EXAMPLE 2

Regulation of Autoinducer Production in *Salmonella typhimurium*

In this example, the conditions under which *S. typhimurium* LT2 produces AI-2, the extracellular factor that stimulates lux expression in the *V. harveyi* Sensor $1^-$, Sensor $2^+$ reporter strain, are elucidated. Production of the signaling molecule by *S. typhimurium* occurs during growth on preferred carbohydrates that, upon utilization by the bacteria, result in a decrease in the pH of the medium. Lowering the pH of the growth medium in the absence of a preferred carbon source induces limited production of the factor, indicating that the cells are influenced by both the changing pH and the utilization of the carbon source. The signaling activity is degraded by the time the cells reach stationary phase, and protein synthesis is required for degradation of the activity. Osmotic shock following growth on an appropriate carbon source greatly increases the amount of activity present in the *S. typhimurium* culture fluids. This increased activity is apparently due to induction of synthesis of the autoinducer and repression of degradation of the activity. *E. coli* and *S. typhimurium* possess a protein called SdiA which is homologous to LuxR from *V. fischeri* (Wang et al., EMBO J. 10: 3363–3372, 1991; Ahmer et al., J. Bacteriol. 180: 1185–1193, 1998). SdiA is proposed to respond to an extracellular factor (Sitnikov et al., Proc. Natl. Acad. Sci. USA 93: 336–341, 1996; Garcia-Lara et al., J. Bacteriol. 178: 2742–2748, 1996), and it has been shown to control virulence factor production in *S. typhimurium* (Ahmer et al., 1998, supra). The analysis set forth below shows that the AI-2 autoinducer signaling activity does not function through the SdiA pathway.

Materials and Methods

Strains and Media. The bacterial strains used in this study and their genotypes and phenotypes are listed in Table 2.

TABLE 2

Bacterial strains; their genotypes and relevant phenotypes.

| Strain | Genotype | Relevant Phenotype |
|---|---|---|
| *S. typhimurium* LT2 type | | Wild |
| *E. coli* O157 type | | Wild |
| *E. coli* MG1655 type | $F^-$, ilvG, rfb-50 | Wild |
| *E. coli* MC4100 | (lac)U169, araD139, rpsL, thi | LacZ$^-$ |
| *E. coli* DH5 | supE44, hsdR17, recA1, endA1, gyrA96, thi-1, relA1 | AI-2$^-$ |
| *V. harveyi* BB170 | luxN::Tn5 | Sensor 1$^-$, Sensor 2$^+$ |
| *V. harveyi* BB152 | luxL::Tn5 | AI-1$^-$, AI-2$^+$ |
| *V. harveyi* JAF305 | luxN::Cm$^r$ | Sensor 1$^-$, Sensor 2$^+$ |

Luria broth (LB) contained 10 g Bacto Tryptone (Difco), 5 g Yeast Extract (Difco) and 10 g NaCl per liter (Sambrook et al., 1989). The recipe for Autoinducer Bioassay (AB) medium has been reported previously (Greenberg et al., Arch. Microbiol. 120: 87–91, 1979). LM medium (L-Marine) contains 20 g NaCl, 10 g Bacto Tryptone, 5 g Bacto Yeast Extract and 15 g Agar per liter (Bassler et al., 1994, supra). Regulation of AI-2 production similar to that reported here was also observed with the ATCC strain Salmonella enterica Serovar Typhimurium 14028, an independent clinical isolate of *Salmonella enterica* Serovar Typhimurium, and nine other *Salmonella enterica* serovars (other than Typhimurium).

Growth conditions for *S. typhimurium* LT2 and preparation of cell-free culture fluids. *S. typhimurium* LT2 was grown overnight in LB broth with shaking at 30° C. The next day, 30 l of the overnight culture was used to inoculate 3 ml of fresh LB broth. In cultures containing additional carbon sources, at the time of inoculation, 20% sterile stock solutions were added to give the specified final concentrations. Following subculturing of the cells, the tubes were shaken at 200 rpm at 30C for the time periods indicated in the text. Cell-free culture fluids were prepared by removal of the cells from the culture medium by centrifugation for 5 min at 15,000 rpm in a microcentrifuge. The cleared supernatants were passed through 0.2 m cellulose acetate Spin X filters (CoStar, Cambridge, Mass.) by centrifugation for 1 min at 8000×g. Samples were stored at −20C. Similar results to those reported here were obtained when we grew the *S. typhimurium* at 37° C. The preparation of cell-free culture fluids from *V. harveyi* strains has already been reported (Bassler et al., 1993, supra; Bassler et al., 1997, supra).

Density-dependent bioluminescence assay. The *V. harveyi* reporter strain BB170 (Sensor 1−, Sensor 2+) (Bassler et al., 1993, supra) was grown for 12 h at 30° C. in AB medium, and diluted 1:5000 into fresh AB medium. Luminescence was measured as a function of cell density by quantitating light production at different times during growth with a Wallac Model 1409 liquid scintillation counter (Wallac Inc., Gaithersburg, Md.). The cell density was measured by diluting the same aliquots of cells used for measuring luminescence, spreading the dilutions onto solid LM medium, incubating the plates overnight at 30° C., and counting the resulting colonies the following day. Relative Light Units are (counts $min^{-1}$ $ml^{-1} \times 10^3$)/(colony forming units $ml^{-1}$). Cell-free culture supernatants from *V. harveyi* or *S. typhimurium* strains were added to a final concentration of 10% (v/v) at the time of the first measurement. In control experiments, 10% (v/v) of AB medium, LB medium or LB medium containing 0.5% glucose was added instead of cell-free culture fluids.

*S. typhimurium* autoinducer activity assay. The quorum sensing signaling activity released by *S. typhimurium* LT2 was assayed following growth under various conditions. 10 l of cell-free culture fluids from *S. typhimurium* LT2 grown and harvested as described above were added to 96-well microtiter dishes. The *V. harveyi* reporter strain BB170 was grown overnight and diluted as described above. 90 l of the diluted *V. harveyi* cells were added to the wells containing the *S. typhimurium* cell-free culture fluids. Positive control wells contained 10 l of cell-free culture fluid from *V. harveyi* BB152 (AI-1−, AI-2+) (Bassler et al., 1993, supra). The microtiter dishes were shaken in a rotary shaker at 200 rpm at 30° C. Light production was measured hourly using a Wallac Model 1450 Microbeta Plus liquid scintillation counter designed for microtiter dishes (Wallac Inc., Gaithersburg, Md.). In these experiments, the cell density was not measured at each time point. Rather, to ensure that increased light production was due to a signaling activity and not a growth medium component, the luminescence production by *V. harveyi* in wells containing cell-free culture fluids was compared to that produced by *V. harveyi* in wells containing 10 l of the identical growth medium alone. Data are reported as fold-stimulation over that obtained for growth medium alone.

Factors controlling signal production in *S. typhimurium*. *S. typhimurium* LT2 was grown for 6 h in LB containing 0.5% glucose as described above. The mid-exponential phase culture was divided into several identical aliquots. One aliquot of cells was grown to stationary phase (24 h at 30° C. with shaking). In the remaining aliquots, the cells were removed from the LB-glucose growth medium by centrifugation for 5 min at 15,000 rpm in a microcentrifuge. The resulting cell pellets were resuspended at an $OD_{600}$ of 2.0 in either LB, LB+0.5% glucose, LB at pH 5.0, or in 0.1M NaCl, or 0.4M NaCl (in water). The resuspended cells were shaken at 30° C. or 43° C. for 2 h. Cell-free fluids were prepared from the stationary phase culture, and from the cells that had been resuspended and incubated in the various media or the osmotic shock solutions. The cell-free fluids were tested for signaling activity in the *S. typhimurium* activity assay as described above.

Effects of growth phase, pH, glucose concentration and osmolarity on autoinducer production by *S. typhimurium*. *S. typhimurium* LT2 was grown at 30° C. for various times in LB containing limiting (0.1%) and non-limiting (1.0%) glucose concentrations. At the times specified in the text, the cell number was determined by plating dilutions of the *S. typhimurium* cultures onto LB medium and counting colonies the following day. The pH of the two cultures was measured, and the percent glucose remaining in each culture was determined using the Trinder assay as described in Example 1. Cell-free culture fluids were prepared from the LB-glucose cultures as described above. The same cells from which the cell-free culture fluids were prepared were resuspended in 0.4M NaCl osmotic shock solution and shaken at 200 rpm, 30° C. for 2 h. We determined that this timing was optimal for production of autoinducer. The cells were removed from the osmotic shock solution by centrifugation at 15,000 rpm for 5 min in a microcentrifuge. Cell-free osmotic shock fluids were prepared from the resuspended cells exactly as described for cell-free culture fluids. Signaling activity in both the cell-free culture fluids and the cell-free osmotic shock fluids was assayed as described above. In experiments in which the pH was maintained at 7.2, the cells were grown in LB+0.5% glucose containing 50 mM MOPS at pH 7.2. The pH was adjusted every 15–30 min using 1 M MOPS pH 7.2. In experiments performed at pH 5.0, LB broth was maintained between pH 5.0 and 5.2 with 1M NaOH.

Requirement for protein synthesis in signal production, release and degradation by *S. typhimurium* LT2. *S. typhimurium* LT2 was pre-grown in LB containing 0.5% glucose at 30° C. to an $OD_{600}$ of 2.5 (approximately 6–8 h) The culture was divided into four identical aliquots. Two aliquots were treated with 100 g/ml Cm for 5 min at room temperature after which the cells were harvested by centrifugation at 15,000 rpm for 5 min. One Cm-treated cell pellet was resuspended in 0.1M NaCl containing 30 g/ml Cm, and the second pellet was resuspended in 0.4M NaCl containing 30 g/ml Cm. Each of these pellets was resuspended to a final $OD_{600}$ of 2.0. The remaining two culture aliquots were not treated with Cm. Instead, the cells in these two aliquots were harvested by centrifugation and resuspended in 0.1M and 0.4M NaCl exactly as described for the Cm-treated cells. The cell suspensions were incubated at 30° C. with shaking. At the times indicated in the text, 1.5 ml aliquots were removed from the cell suspensions and cell-free osmotic shock fluids were prepared by the procedure described above.

"Analysis of the effect of autoinducer on SdiA regulated gene expression. A sequence that includes the fisQ1p and ftsQ2p promoters (Wang et al., 1991, supra) was amplified from *E. coli* MG1655 chromosomal DNA using the following primers: fisQ1p, 5'-CGGAGATCTGCGTTTCAATGGATAAACTACG-3' (SEQ ID NO: 19); ftsQ2p, 5'-CGCGGATCCTCTTCTTCGCTGTTTCGCGTG-3' (SEQ ID NO: 20). The amplified product contained both the ftsQ promoters and the first 14 codons of the ftsQ gene flanked by BamHI and BglII sites. The ftsQ1p2p PCR product was cloned into the BamHI site of vector pMLB 1034 (Silhavy et al., Experiments with Gene Fusions, Cold Spring Harbor Press, 1984) to generate a lacZ fusion that contained the promoters, ribosome binding site, and initiation codon of ftsQ. A correctly oriented clone, pMS207, and a clone containing the ftsQ1p2p insert in the opposite orientation, pMS209, were chosen for further analysis. Both inserts were sequenced to ensure that no errors were introduced during the PCR reaction."

For ftsQ regulation in *E. coli*, the plasmids pMS207 and pMS209 were transformed into *E. coli* strain MC4100

(Silhavy et al., 1984, supra), and the transformants were grown overnight in LB containing 100 mg/L ampicillin at 30° C. with aeration. For rck regulation, *S. typhimurium* strains BA1105 (rck::MudJ) and BA1305 (rck::MudJ sdiA) were grown overnight in LB containing 100 mg/L kanamycin at 30° C. with aeration. The overnight cultures were diluted 20-fold into fresh medium and grown for an additional 4.5 h. At this time, each culture was divided into five identical aliquots and 10% (v/v) of one of the following was added to each aliquot: LB, 0.4M NaCl, 0.4M osmotic shock fluids from *S. typhimurium* LT2, *E. coli* O157 or *E. coli* strain DH5 (negative control). The osmotic shock fluids were prepared as described above, following pre-growth of the *S. typhimurium* LT2 and *E. coli* in LB containing 0.5% glucose for 6 h. The cell suspensions were incubated at 30° C. for 2 h, after which standard -galactosidase reactions were performed on the samples (Miller, A Short Course in Bacterial Genetics, Cold Spring Harbor Laboratory Press, 1992).

Results

Figure 4:
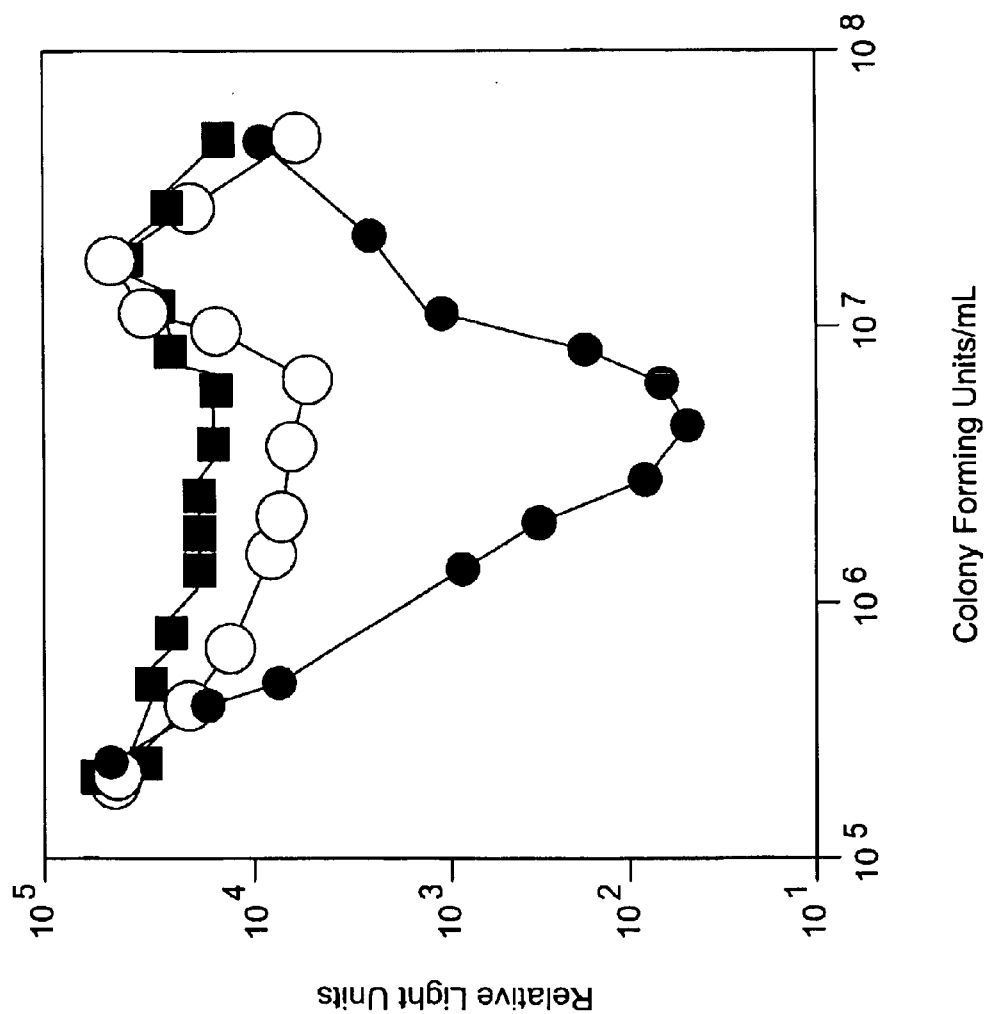
FIG. 4. Response curve of *V. harveyi* to AI-2 produced by *V. harveyi* and *S. typhimurium*. The *V. harveyi* reporter strain BB170 (Sensor 1⁻, Sensor 2⁺) was tested for its response to the addition of exogenous AI-2 made by *V. harveyi* strain BB152 (AI-1⁻, AI-2⁺) and to that made by *S. typhimurium* LT2. A bright culture of the reporter strain was diluted 1:5000 and either 10% (v/v) growth medium (closed circles), cell-free culture fluid from *V. harveyi* BB152 grown overnight in AB (open circles), or cell-free culture fluid from *S. typhimurium* LT2 grown for 6 h on LB+0.5% glucose (closed squares) was added at the start of the experiment. RLU denotes relative light units and is defined as (counts min$^{-1}\times10^3$)/(colony-forming units ml$^{-1}$).

*S. typhimurium* LT2 produces an autoinducer-like activity. In Example 1 it was demonstrated that *S. typhimurium* and *E. coli* strains produce a signaling activity that stimulates lux expression in *V. harveyi*, and the signaling molecule acts exclusively through the *V. harveyi* quorum sensing System 2. FIG. 4 shows the induction of luminescence in the *V. harveyi* System 2 reporter strain BB170 (Sensor 1$^-$, Sensor 2$^+$). The characteristic quorum sensing behavior of *V. harveyi* is shown in the control experiment (closed circles). Immediately after dilution into fresh medium, the light emitted per cell by *V. harveyi* drops rapidly, over 1000-fold. At a critical cell density, which corresponds to the accumulation of a critical concentration of endogenously produced autoinducer (AI-2) in the medium, the luminescence per cell increases exponentially, approximately 3 orders of magnitude, to again reach the pre-dilution level.

Addition of 10% cell-free culture fluid prepared from *V. harveyi* BB152 (AI-1$^-$, AI-2$^+$) caused the reporter strain to maintain a high level of light output following dilution (open circles). The increased light output is due to the *V. harveyi* BB170 cells responding to the presence of AI-2 in the cell-free culture fluids prepared from *V. harveyi* strain BB152 (Bassler et al., 1993, supra). Similarly, addition of cell-free culture fluid from *S. typhimurium* LT2 grown in LB+0.5% glucose induced luminescence in the reporter strain approximately 800-fold over the control level (solid squares). No activity similar to *V. harveyi* AI-1 was produced by *S. typhimurium* LT2 under these conditions and there is no AI-1 or AI-2 activity in LB+0.5% glucose (see Example 1).

Figures 5A, 5B:
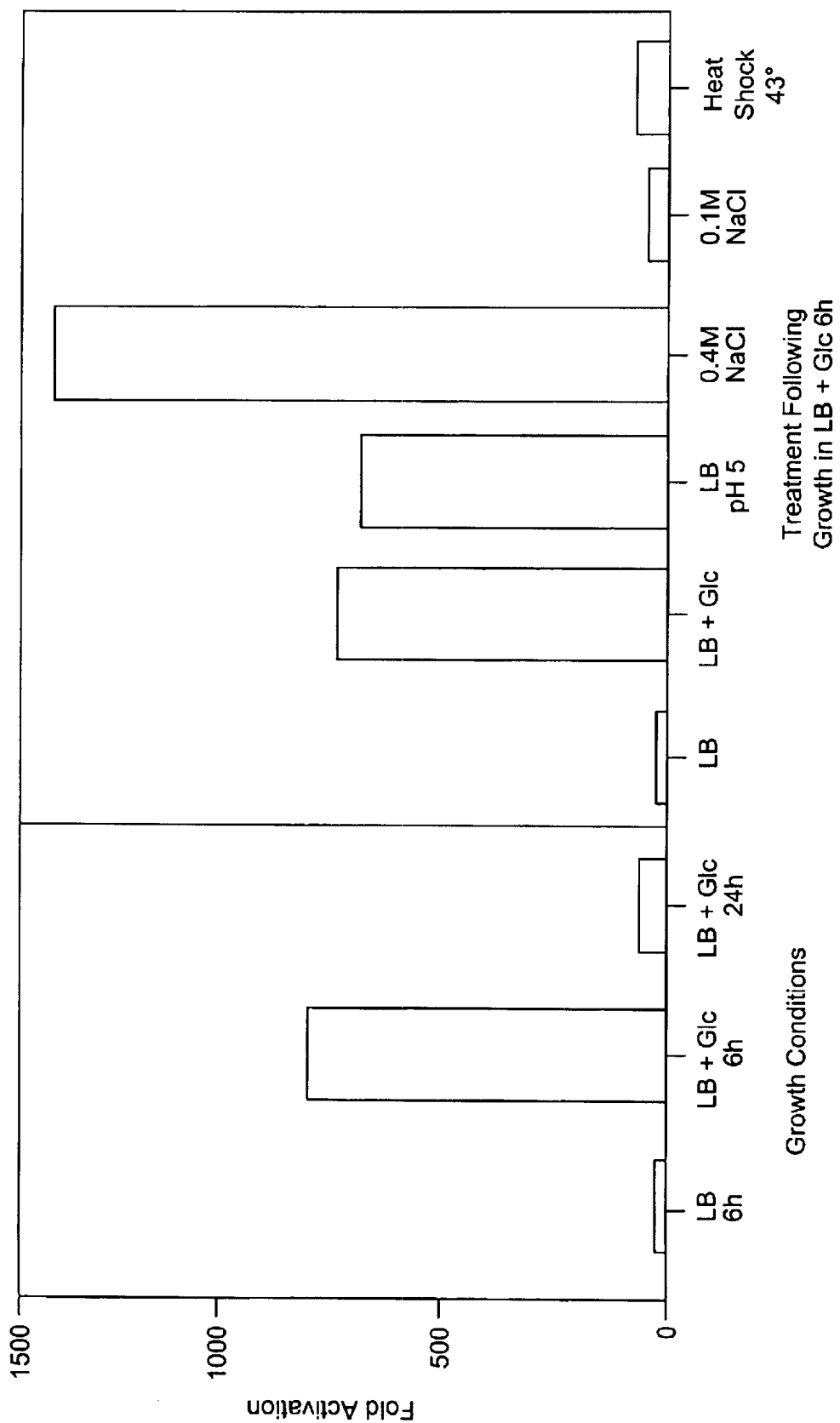
FIGS. 5A–B. Conditions affecting autoinducer production in *S. typhimurium*. *S. typhimurium* LT2 was subjected to a variety of treatments after which cell-free culture fluids or osmotic shock fluids were prepared. These preparations were added to a diluted culture of the *V. harveyi* AI-2 reporter strain BB170 at 10% (v/v) and light output was measured thereafter. Fold activation is the level of light produced by the reporter following addition of the specified *S. typhimurium* preparation divided by the light output of the reporter when growth medium alone was added. The bars in FIG. 5A represent cell-free fluids prepared from *S. typhimurium* after the following treatments: LB 6 h; 6 h growth in LB at 30° C., LB+Glc 6 h; 6 h growth in LB+0.5% glucose at 30° C., LB+Glc 24 h; 24 h growth in LB+0.5% glucose at 30° C. In all the experiments presented in FIG. 5B, the *S. typhimurium* were pre-grown at 30° C. for 6 h in LB containing 0.5% glucose, then pelleted and resuspended for 2 h under the following conditions: LB; in LB at 30° C., LB+Glc; in LB+0.5% glucose at 30° C., LB pH 5; in LB at pH 5.0 at 30° C., 0.4M NaCl; in 0.4M NaCl at 30° C., 0.1M NaCl; in 0.1M NaCl at 30° C., and Heat Shock 430; in LB+0.5% glucose at 43° C. After these two hour treatments, cell-free fluids were prepared from each sample and assayed.

Environmental factors influence autoinducer production and degradation in *S. typhimurium*. Control of autoinducer production in *S. typhimurium* is different than in other described quorum sensing systems. FIG. 5A demonstrates three important aspects of the regulation of autoinducer production in *S. typhimurium*. First, no autoinducer activity is observed when *S. typhimurium* is grown for 6 h in LB in the absence of glucose. Second, growth in the presence of glucose for 6 h results in substantial production of autoinducer (760-fold activation of the reporter strain). Third, activity, while detectable, is severely reduced when the *S. typhimurium* culture is allowed to grow to stationary phase (33-fold activation of the reporter strain).

We subjected *S. typhimurium* LT2 to several different treatments including some environmental stresses in order to begin to understand what conditions favor autoinducer production versus those that favor autoinducer degradation. In the experiment presented in FIG. 5B, the *S. typhimurium* cells were induced for signal production by pre-growth in LB containing 0.5% glucose for 6 h. We have shown that under these conditions, the glucose is not depleted (Surette and Bassler, 1998). After the induction phase of growth, the culture fluid was removed and aliquots of the cells were resuspended and incubated for 2 h under a variety of conditions that are described in the description of FIG. 2. Following each of these treatments cell-free fluids were prepared and tested for activity on BB170.

It is important to note that in the results presented in FIG. 5B, the *S. typhimurium* were pre-induced for autoinducer production at the start of the experiment, i.e., their cell-free culture fluid activated the reporter strain 760-fold. FIG. 5B shows that removal of the pre-growth culture fluid from these cells and resuspension of the cells in LB without glucose, in 0.1 M NaCl (hypotonic conditions), or heat shock at 43° C. for 2 h resulted in no or very low autoinducer production. These results indicate that the above treatments result in termination of autoinducer production, or degradation of newly released autoinducer, or both.

In contrast to the above results, resuspension of pre-induced cells in fresh LB+glucose resulted in continued high-level production of autoinducer (735-fold activation of the reporter). Similarly, acidic pH promoted continued production of autoinducer (600-fold activation), and hypertonic osmotic shock (0.4M NaCl) resulted in 1300-fold induction of the reporter. Increased AI-2 activity was only observed in the pH 5.0 fluids or 0.4M NaCl osmotic shock fluids of cells that were already actively producing AI-2, i.e., if glucose was not included during the pre-growth, no measurable activity was produced following the identical 2 h treatments.

Shifting *S. typhimurium* cells from LB+glucose to 0.4M NaCl resulted in an accumulation of AI-2 activity to a level much greater than that observed under any other condition tested. Below it is shown that *S. typhimurium* cells resuspended in 0.4M NaCl increase the biosynthesis and/or release of autoinducer, and furthermore they apparently do not degrade significant quantities of the released activity. A similar increase in AI-2 production occurs when the *S. typhimurium* cells are resuspended in 0.4M NaCl, 0.4M KCl or 0.8M sucrose, indicating that the NaCl effect on AI-2 production is an osmotic one, not an ionic one. This apparent osmotic shock effect on the *S. typhimurium* cells was extremely useful because it enabled us to measure maximal release of autoinducer activity in the absence of loss due to degradation.

The effect of glucose on signal production in *S. typhimurium*. In Example 1 we showed that the continued presence of glucose was required for *S. typhimurium* to produce the quorum sensing signaling factor. Because sugar utilization both increases the growth rate while decreasing the pH of the culture, we further analyzed the effect of metabolism of glucose, decreasing pH and increasing cell number on signal production by *S. typhimurium*. In the experiment presented in FIG. 6, we measured signal production, growth rate, and pH in growing *S. typhimurium* LT2 cultures containing limiting (0.1%) and non-limiting (1.0%) concentrations of glucose. In the data presented in FIG. 6, at various times, the level of autoinducer produced in both the cell-free culture fluids and in the corresponding 0.4M NaCl osmotic shock fluids was measured and normalized for $1 \times 10^9$ cells. It should be noted that unlike in FIG. 5, the cells in this experiment were not pre-induced for signal production.

FIG. 6 shows that the pattern of production and disappearance of autoinducer observed in 0.4M NaCl osmotic shock fluids mimics that observed in cell-free culture fluids.

However, at every time point that autoinducer is produced, much greater activity is detected in the osmotic shock fluids than in the corresponding cell-free culture fluids. Under conditions of limiting (0.1%) glucose (FIGS. 6A, 6C and 6E), S. typhimurium produces the signaling activity between 2–4 h (Bars). However, the glucose becomes completely depleted at 4 h, and at that time production of the factor ceases (FIG. 6A). In contrast, when the cells are grown in 1.0% glucose (FIGS. 6B, 6D, and 6F), glucose is present in the medium throughout the entire experiment (FIG. 6B). Under these conditions, the cells continue to synthesize activity for 12 hours. Similar to the results shown in FIG. 5 and those reported in Example 1, almost no activity was observed in cell-free culture fluids or osmotic shock fluids from stationary phase cells at 24 h regardless of the glucose concentration.

S. typhimurium grows at roughly the same rate in both high and low glucose media during exponential phase. In fact, the S. typhimurium culture grown in high glucose medium does not reach the cell density achieved by the S. typhimurium grown in the low glucose medium (FIGS. 6C and 6D). Cell growth is probably inhibited in this culture by the dramatically reduced pH that occurs from increased glucose utilization. These results show that the higher level of activity produced by S. typhimurium in the LB containing 1% glucose is not due to higher cell number, but due to induction of signal production caused by glucose metabolism.

FIGS. 6E and 6F show the pH of the low and high glucose cultures at each time point. Under conditions of low glucose (FIG. 6E), the pH of the culture initially decreases as the cells utilize the glucose. However, simultaneous to the complete depletion of the glucose, the pH begins to rise. In contrast, under conditions of high glucose, the pH of the medium decreases to below pH 5 (FIG. 6F). In the experiments presented in FIG. 6, both glucose catabolism and decreasing pH occur simultaneously suggesting that either or both of these factors could be responsible for signal production by S. typhimurium.

Figures 7A, 7B:
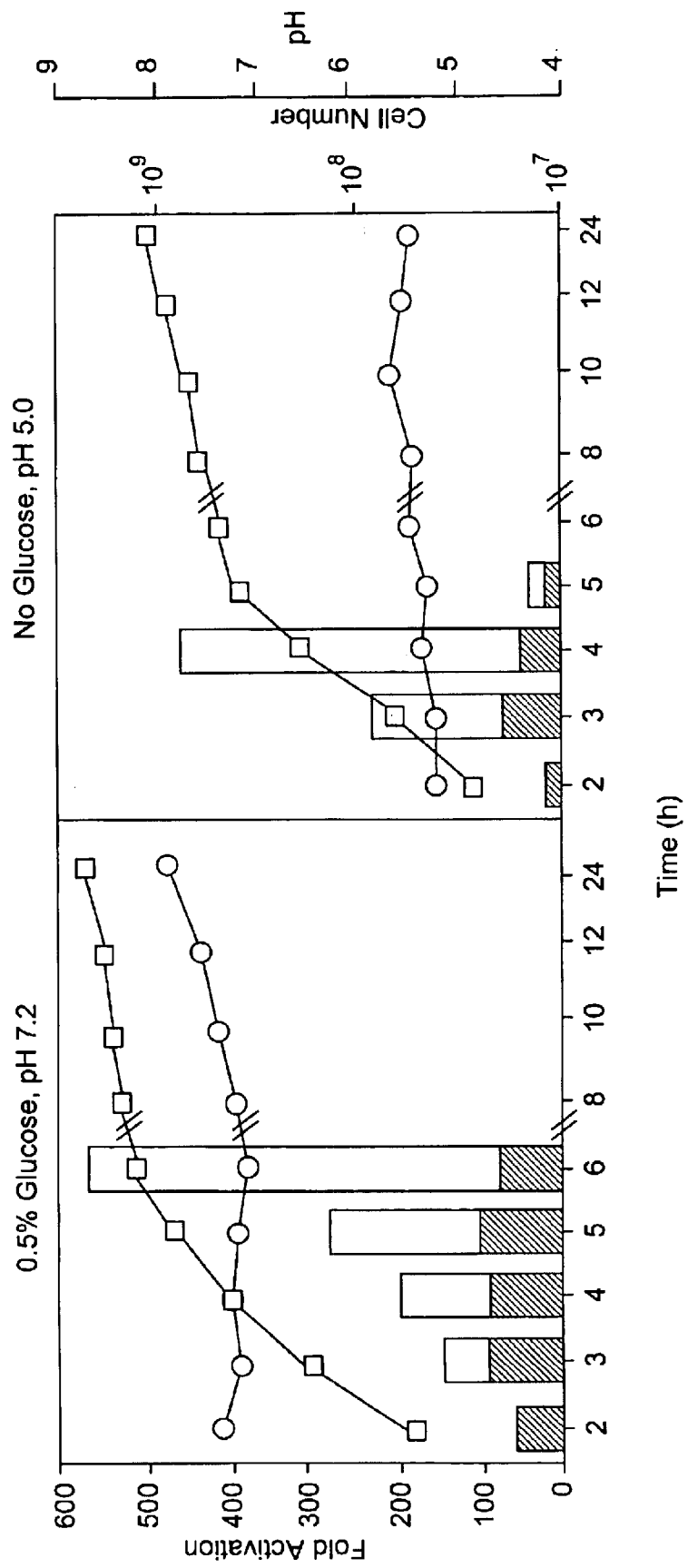
FIGS. 7A–B. Effects of glucose and pH on signal production by *S. typhimurium*. The quorum sensing signal released by *S. typhimurium* LT2 was measured when the cells were grown in LB medium containing 0.5% glucose at pH 7.2 (FIG. 7A, bars), and when the cells were grown in LB at pH 5.0 without an added carbon source (FIG. 7B, bars). The level of signal present in cell free culture fluids (black bars) and in 0.4M NaCl osmotic shock fluids was measured (white bars on top of black bars) at the time points indicated. In each panel, the circles represent the pH of the medium, and the squares show the cell number at the different time points.

Both glucose metabolism and low pH independently control signal production in S. typhimurium. To distinguish between the contribution from glucose metabolism and that from low pH in signal production by S. typhimurium, we compared the activity produced by S. typhimurium grown in LB containing 0.5% glucose in a culture in which the pH was maintained at 7.2 (FIG. 7A), to that produced by S. typhimurium grown in LB without glucose where the pH was maintained at 5.0 (FIG. 7B). Again, we measured the signal present in cell-free culture fluids and in 0.4M NaCl osmotic shock fluids. Similar to the data presented in FIG. 3, the level of signal observed in cell-free culture fluids was lower than that observed in the 0.4M osmotic shock fluids.

When S. typhimurium was grown in LB+0.5% glucose at pH 7.2 increasing amounts of the quorum sensing signal were detected for 6 h. At 6 h, in 0.4M NaCl osmotic shock fluids, there was an approximately 550-fold stimulation of light production of the V. harveyi reporter strain BB170. No activity was produced after the 6 h time point. FIG. 7A shows that the pH was maintained between 7.15 and 7.25 for 8 h, after this time, the pH of the culture no longer decreased, but began increasing presumably because the cells had depleted the glucose. We allowed the pH to continue to increase for the duration of the experiment. Also shown in the Figure is the cell number at each time point. At pH 7.2, the cells grew rapidly and reached a high cell density.

Analysis of time courses similar to those presented here, has shown that S. typhimurium does not produce any signal when it is grown in LB without glucose at neutral pH (see Example 1). However, S. typhimurium did transiently produce the quorum sensing factor in the absence of glucose when grown at pH 5.0 (FIG. 7B). Signal was produced for 4 h, and about 450-fold stimulation of the reporter was the maximum activity achieved in 0.4M NaCl osmotic shock fluids. Very little signal was produced by 5 h, and signal was completely absent after 6 h of incubation. FIG. 7B shows that the pH was maintained between 5.0 and 5.2 in this experiment. Note that the cells grew much more slowly at pH 5.0 than at pH 7.2.

Preliminary characterization of the S. typhimurium autoinducer degradative apparatus. The quorum sensing activity produced by S. typhimurium LT2 is degraded by the onset of stationary phase. We have determined that the activity contained in cell-free culture supernatants and 0.4M NaCl osmotic shock fluids from cells grown for 6 h in LB+glucose is stable for at least 24 h at 30° C., indicating that no degradative activity is present in these cell-free fluids. Furthermore, mixing cell-free culture fluids prepared from actively producing S. typhimurium (i.e., from cultures grown for 6 h in LB+glucose) with cell-free culture fluids prepared from S. typhimurium that have degraded the factor (i.e., from cultures grown for 12 or 24 h in LB+glucose) does not result in degradation of the activity. This result indicates that the degradative activity is not released, but instead, is associated with the cells.

We show in FIG. 5 that no further autoinducer is produced if S. typhimurium cells that are actively releasing autoinducer are shifted to 0.1M NaCl. However, when these same cells are shifted to 0.4M NaCl, we observe even greater autoinducer production. This result implies that low osmolarity could be a signal that induces the autoinducer degradative machinery. To begin to analyze the mechanism by which osmolarity affects autoinducer production and degradation in S. typhimurium, we investigated the requirement for protein synthesis in signal production and degradation by S. typhimurium in high and low osmolarity. As described in the legend to FIG. 5, S. typhimurium LT2 was grown in LB containing 0.5% glucose to achieve maximal induction of signal production then treated with 0.1M or 0.4M NaCl in the presence and absence of protein synthesis. Cell-free fluids were prepared and tested for signaling activity. Because half of the cell-free osmotic shock fluids contained chloramphenicol (Cm), V. harveyi JAF305 was used as the reporter strain in the activity assay. This V. harveyi strain contains a $Cm^r$ cassette in the luxN gene, and its phenotype is Sensor $1^-$, Sensor $2^+$, a phenotype identical to that of V. harveyi BB170.

Figures 8A, 8B:
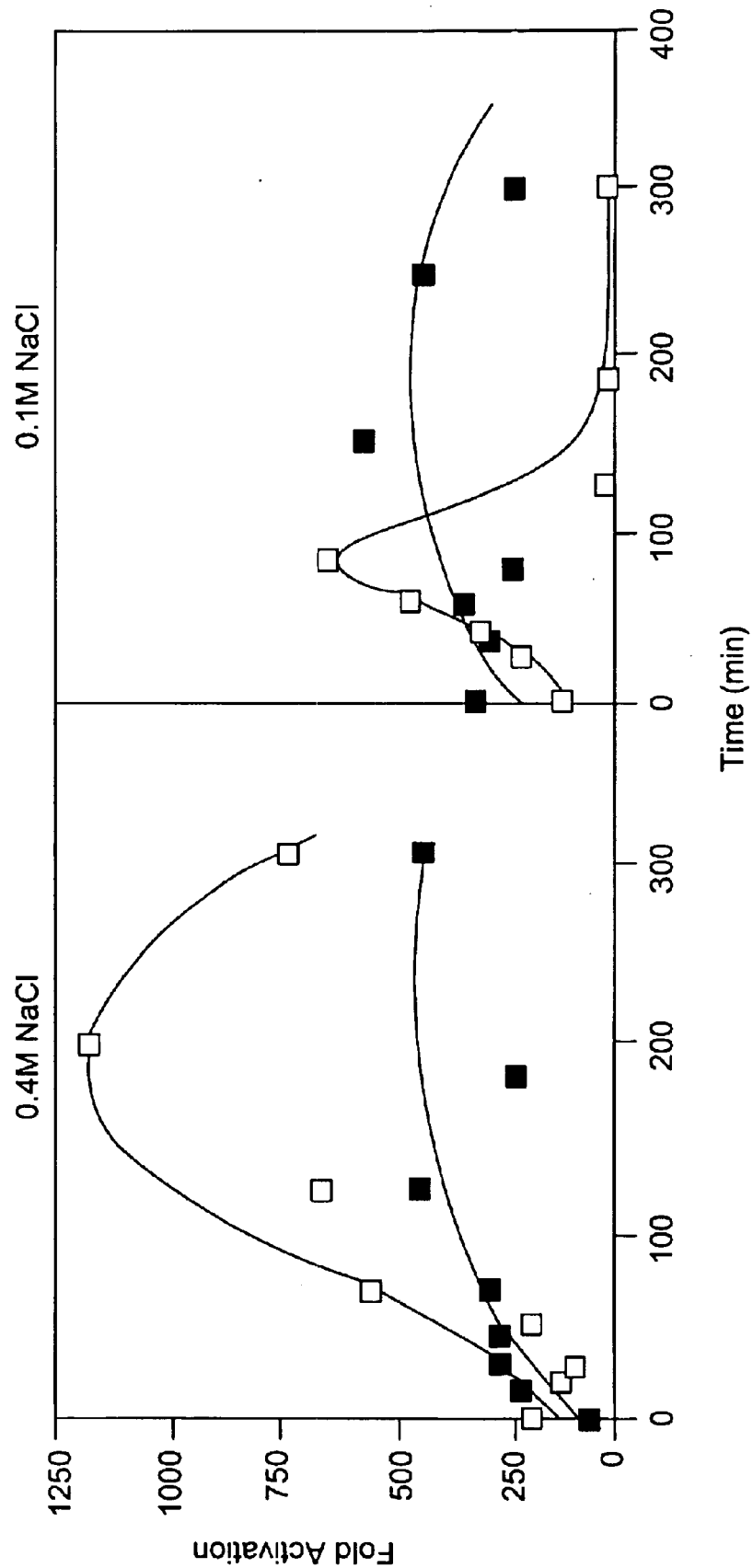
FIGS. 8A–B. High osmolarity induces signal release and low osmolarity induces signal degradation in *S. typhimurium* LT2. The quorum sensing signal released by *S. typhimurium* LT2 resuspended in 0.4M NaCl and in 0.1M NaCl was measured in the presence and absence of protein synthesis. *S. typhimurium* LT2 was pre-grown in LB containing 0.5% glucose for 6 h. The cells were harvested and resuspended in 0.4 M NaCl (FIG. 8A) or 0.1 M NaCl (FIG. 8B) in the presence or absence of 30 g/ml Cm for the time periods indicated. In each panel, the open symbols represent the activity measured in the absence of Cm and the closed symbols represent the activity measured in the presence of Cm.

When the cells were resuspended in 0.4M NaCl, the S. typhimurium produced and released increasing amounts of the signal for 200 min (FIG. 8A, open squares). After this time, the level of signaling activity present in the cell-free osmotic shock fluid decreased somewhat, suggesting that some of the released signal was degraded. Quite different results were obtained when the S. typhimurium cells were resuspended in 0.1M NaCl (FIG. 8B, open squares). In this case, at early time points, the S. typhimurium produced a quantity of activity equivalent to that produced by cells resuspended in 0.4M NaCl. However, by 120 min, no activity remained in the cell-free low osmolarity fluid. This result indicates that under conditions of low osmolarity, the released activity is rapidly degraded. We do not observe degradation of the activity in cell-free culture fluids, indicating that the disappearance of the activity from low osmolarity cell-free fluids is not due to chemical instability of the signaling molecule.

Under conditions of high osmolarity, when the cells were treated with Cm to inhibit protein synthesis, only about one quarter of the activity was produced compared to untreated cells. The closed squares in FIG. 8A show that 300-fold induction of the reporter strain occurred in the presence of Cm as compared to 1200-fold induction with the untreated cells (FIG. 8A, open squares). When the S. typhimurium was resuspended in low osmolarity (FIG. 8B), roughly three-quarters of the activity produced in the absence of Cm (open squares) was produced in the presence of Cm (closed squares). In the presence of Cm, the released activity was not degraded by 300 min in high osmolarity and only partially degraded in low osmolarity.

To show that high osmolarity does not inhibit AI-2 signal degradation, we added the activity contained in the 0.4M NaCl cell-free osmotic shock fluids to S. typhimurium cells that had been resuspended in 0.1M NaCl for two hours. As shown in FIG. 8, these are cells that can degrade the factor. Table 3 shows that these S. typhimurium cells degraded greater than 98% of the signaling activity while incubated at high osmolarity. The table also shows that S. typhimurium cells that had been incubated in 0.4M NaCl (these are cells that are actively producing the signal) released no further activity when resuspended in the 0.1M NaCl incubation fluid obtained from the actively degrading cells. Furthermore, mixing active and inactive 0.4M and 0.1M cell-free osmotic fluids did not result in degradation of the activity in the 0.4M fluids.

TABLE 2

High osmolarity induces release and low osmolarity induces degradation of the S. Typhimurium signaling factor.

| Treatment | Fold-induction of luminescence |
| --- | --- |
| 0.1 M NaCl activity[a] | 4 |
| 0.4 M NaCl activity[a] | 944 |
| 0.1 M cells + 0.4 M activity[b] | 17 |
| 0.4 M cells + 0.1 M activity[c] | 6 |

[a]S. typhimurium was grown for 6 h in LB containing 0.5% glucose. The cells were pelleted and resuspended in either 0.1 M or 0.4 M NaCl for 2 h. Cell-free fluids were prepared and tested for activity.
[b]S. typhimurium cells that had been incubated in 0.1 M NaCl for two hours were pelleted and resuspended in the activity contained in the cleared osmotic shock fluids obtained from cells suspended in 0.4 M NaCl for 2 h. Cell-free fluids were prepared after a 2 h incubation and assayed for signaling activity.
[c]S. typhimurium cells that had been suspended in 0.4 M NaCl were pelleted and incubated for 2 h in the cleared osmotic shock fluids obtained from cells suspended for 2 h in 0.1 M NaCl. Cell-free fluids were prepared after the 2 h incubation and assayed for signaling activity.

The LuxR homolog SdiA is not involved in response to the AI-2 autoinducer. A gene homologous to luxR of V. fischeri has been identified in E. coli and S. typhimurium and is called sdiA. Two reports suggest that in E. coli, SdiA modestly regulates the expression of the cell division locus ftsQAZ in response to a factor present in cell-free culture fluids (Garcia-Lara et al., 1996, supra), and in response to a few homoserine lactone autoinducers (Sitnikov, et al., 1996, supra). Completion of the sequence of the E. coli genome shows that no LuxI homologue exists in E. coli so the locus responsible for the biosynthesis of the hypothesized soluble factor(s) has not been determined. Overexpression of SdiA in S. typhimurium has recently been shown to influence the expression of several ORFs located on the S. typhimurium virulence plasmid (Ahmer, et al., 1998, supra). As in the E. coli studies, SdiA activity in S. typhimurium is proposed to be modulated by an extracellular factor.

It was possible that the AI-2 autoinducer that we have been characterizing in S. typhimurium and E. coli acted through SdiA. We tested whether AI-2 had an effect on genes regulated by SdiA in E. coli and S. typhimurium. In E. coli, we assayed an ftsQ1p2p-lacZ reporter, and in S. typhimurium we assayed an rck::MudJ fusion in both an sdiA[+] and sdiA[−] background. We tested the effects of addition of LB, 0.4M NaCl, 0.4M NaCl osmotic shock fluids containing AI-2 activity from S. typhimurium LT2, E. coli O157, and 0.4M NaCl osmotic shock fluid from E. coli DH5. We have shown previously in Example 1 that DH5 does not produce AI-2 activity under our growth conditions.

For the E. coli experiments we determined that MC4100 and MC4100/pMS209 (containing ftsQ1p2p in the incorrect orientation) had no measurable -galactosidase activity. The level of -galactosidase produced by MC4100/pMS207 (containing the ftsQ1p2p-lacZ fusion) was roughly 20–30 Miller units, and this level of activity did not change under any of the conditions tested here. This level of activity of the fusion was comparable to that reported previously (Sitnikov et al., 1996, supra; Garcia-Lara et al., 1996, supra). In the S. typhimurium SdiA studies, similar to Ahmer et al. (1998, supra), we obtained ~30 Miller units of rck::MudJ activity in the sdiA[+] background and this level was reduced to 10 units in the sdiA[−] background. No change in -galactosidase production occurred following the addition of AI-2 from E. coli or S. typhimurium. These results indicate that, if an extracellular factor exists that modulates the activity of SdiA, under the conditions we have tested, it is not AI-2.

Discussion

Quorum Sensing in E. coli and S. typhimurium. We have developed a heterologous bio-assay that enables us to detect an extracellular signaling factor produced by S. typhimurium. The factor mimics the action of AI-2 of the quorum sensing bacterium V. harveyi, and it acts specifically through the V. harveyi Signaling System 2 detector LuxQ. Results using lacZ fusions to the ftsQ and rck promoters indicate that, under our assay conditions, the AI-2 quorum sensing factor does not signal to SdiA, at least with respect to regulation of these genes. The AI-2 quorum sensing system is therefore involved in a different S. typhimurium and E. coli signal transduction pathway than the one(s) investigated previously.

S. typhimurium LT2 produces an amount of activity roughly equivalent to that produced by V. harveyi. We observe approximately 800-fold stimulation of the V. harveyi reporter strain BB170 upon addition of 10% S. typhimurium cell-free culture fluids. The timing of lux induction and the shape of the response curve of V. harveyi to the S. typhimurium signal are indistinguishable from those of V. harveyi responding to its own AI-2. Furthermore, we have been successful at partially purifying both the V. harveyi AI-2 and the S. typhimurium signal molecule using identical purification procedures. These two results lead us to believe that the S. typhimurium signaling molecule is identical to or very closely related to AI-2 of V. harveyi.

Growth Conditions Regulate Signal Production and Degradation in S. typhimurium. In this example, we further characterize the regulation of the signaling activity in S. typhimurium LT2. Accumulation of signaling activity in S. typhimurium culture supernatants is maximal during mid-exponential phase when the cells are actively utilizing glucose in rich medium. Under these growth conditions, utilization of glucose is accompanied by a rapid drop in pH of the culture. The results demonstrate that either glucose metabolism or low pH is sufficient to induce S. typhimurium LT2 to produce the quorum sensing factor, indicating that both glucose and acidity generate independent signals for autoinducer production. In the presence of glucose, when the pH is not maintained, probably both the decreasing pH and the presence of an appropriate carbon source contribute to the regulation of quorum sensing in S. typhimurium. The results also show that production of the autoinducer ceases prior to stationary phase in the presence of glucose at neutral pH and in the absence of glucose at low pH. Therefore, a combination of acidic conditions and the absence of glucose is not required to cue S. typhimurium to terminate production of autoinducer.

In addition to glucose, growth on several other carbohydrates also induces production of the signaling activity. These include both PTS (fructose, mannose, glucitol, and glucosamine) and non-PTS (galactose and arabinose) sugars. These findings eliminate an exclusive role for the PTS in the regulation of autoinducer biosynthesis. When the S. typhimurium LT2 are grown on several other carbon sources (acetate, glycerol, citrate and serine) no significant accumulation of signaling activity is observed. We have demonstrated in Example 1 that the signal is not any of a number of substances known to be secreted by S. typhimurium including the major products of mixed acid fermentation. Clearly, production of the signaling molecule is precisely regulated by the cells and is favored under conditions of growth on preferred carbohydrates for reasons that we do not yet understand. Identification of the signaling molecule and cloning of the biosynthetic gene(s) will aid in a fuller understanding of the regulation process.

Results presented in this example show that, in contrast to other quorum sensing systems, the S. typhimurium signal does not accumulate in stationary phase. At least two competing processes contribute to this regulation; autoinducer production and autoinducer degradation. In this example we are defining autoinducer production as an increase in the signaling activity present in cell-free fluids. We recognize that an increase in activity could result from release of newly biosynthesized autoinducer, release of stored autoinducer, repression of degradation of autoinducer, or some combination of these activities. We define autoinducer degradation as the disappearance of signaling activity from the cell-free fluids. This disappearance could be due to destruction of the autoinducer, re-uptake of the autoinducer, or a combination of these activities. It is possible that under some of the conditions used in our studies, autoinducer production and autoinducer degradation are occurring simultaneously. If this is the case, the activity detected in cell-free culture fluids is a measure of which of these processes, production or degradation, predominates. These findings indicate that quorum sensing in S. typhimurium is regulated such that the signal and presumably the response to the signal do not persist into stationary phase. Because the utilization of a preferred carbohydrate is also required for signal production, quorum sensing in S. typhimurium may be used both for measuring the cell density and for measuring the potential of the environment for growth.

Osmolarity Influences Signal Production and Degradation in S. typhimurium. S. typhimurium cells that are actively producing signal can be further stimulated to produce signal by specific environmental treatments, indicating that several independent regulatory pathways channel information into autoinducer synthesis. One of these treatments is 0.4M NaCl osmotic shock. When autoinducer producing S. typhimurium cells are resuspended in 0.4M NaCl, the cells release significantly greater activity when they have the capability to synthesize protein than when protein synthesis is blocked. Furthermore, degradation of the signal also requires protein synthesis. These results have several implications. First, in the presence of Cm, S. typhimurium resuspended at both high and low osmolarity produce a similar amount of activity. This result indicates that, following growth in the presence of glucose, the S. typhimurium cells have a pre-defined capacity to produce signaling activity (and/or to release already synthesized activity from the cell). Second, when the cells are resuspended at high osmolarity, signal production increases well beyond this level. This increase in signal production requires protein synthesis, and we interpret this to mean that high osmolarity is one environmental cue that induces S. typhimurium to synthesize more of the biosynthetic apparatus necessary for signal production and/or release. Third, under conditions of low osmolarity, we observe an initial release of activity, followed by a rapid degradation of the activity. And, signal degradation requires protein synthesis because it is not observed in the presence of Cm. These results imply that the environment has changed from conditions favoring autoinducer production (LB+a preferred carbohydrate, or high osmolarity) to conditions where autoinducer production is not favored (low osmolarity, or absence of a preferred carbon source). This environmental change induces S. typhimurium to synthesize the protein(s) required for degradation of the signaling activity.

When the S. typhimurium cells were incubated in 0.4M NaCl no significant degradation of the activity occurred by 200 min. This result indicates that either the necessary degradative protein(s) are not synthesized under these conditions, or alternatively, the degradative apparatus is assembled, but its activity is inhibited by high osmolarity. The results show that high osmolarity does not inhibit signal degradation, because cells induced to degrade the activity can do so at high osmolarity. Therefore, the persistence of the activity in the high NaCl samples occurs because the degradation machinery is not synthesized, not because its activity is inhibited.

It is difficult to precisely determine when S. typhimurium cells are autoinducer producers and when they are autoinducer degraders because both processes could occur simultaneously. It appears, however, that no or very low degradation occurs in high osmolarity, and conversion of cells from overall signal producers to overall signal degraders occurs in low osmolarity and requires protein synthesis. Our preliminary characterization of the degradative process indicates that it is cell-associated because the autoinducer activity is stable in cell-free culture supernatants for long periods of time, and combining active with inactive cell-free culture fluids or active and inactive high and low osmolarity cell-free fluids does not promote degradation of the autoinducer. We have recently isolated a S. typhimurium mutant that does not produce the AI-2 activity. If this mutant retains the capability to degrade autoinducer, analysis of it will be informative for understanding the timing of degradation, and for identifying the cues that induce the degradative machinery. We are currently attempting to isolate S. typhimurium mutants capable of autoinducer production but incapable of autoinducer degradation.

The Role for Quorum Sensing in Salmonella Pathogenesis. The observations presented here on the regulation of signal production and degradation by S. typhimurium LT2 implicate a role for quorum sensing in pathogenesis of Salmonella. The conditions favoring signal production (nutrient rich, high osmolarity and low pH) are those likely to be encountered upon the first interaction of an enteric pathogen with its host. Conditions favoring degradation of the signal (nutrient poor, low osmolarity) are those most probably encountered as the pathogen exits the host. The initial colonization of the host may be a concerted effort between a population of cells coordinated through this cell-cell signaling system. Other cues, that we have not yet tested, could also regulate quorum sensing in *S. typhimurium*. These may represent independent or overlapping signaling pathways involved in pathogenesis. We are isolating *S. typhimurium* mutants to test these hypotheses. Finally, Salmonella pathogenesis is a dynamic process of interaction between the host and metabolically active bacteria. Consistent with a role for quorum sensing in pathogenesis, our evidence suggests that this quorum sensing system is not functioning during stationary phase. We have shown that the signaling molecule is not produced during stationary phase, and furthermore, existing signal is degraded. Perhaps quorum sensing is critical for *S. typhimurium* to undergo the transition between a host-associated and a free-living existence.

EXAMPLE 3
Quorum Sensing in *Escherichia coli, Salmonella typhimurium* and *Vibrio harveyi*: A New Family of Genes Responsible for Autoinducer Production In this example we report the analysis of a gene responsible for AI-2 production in *V. harveyi*, *E. coli* and *S. typhimurium*. The gene identified in all three species of bacteria is highly homologous, and we propose that these genes define a new family of proteins involved in autoinducer production. The genes, which we named $luxS_{V.h.}$, $luxS_{E.c.}$, and $luxS_{S.t.}$ have been identified in many species of bacteria by genome sequencing projects, but until now no function has been ascribed to this gene in any organism. The luxS genes do not bear homology to any other gene known to be involved in autoinducer production.

Materials and Methods

Bacterial strains, media and recombinant DNA techniques. *V. harveyi* BB120 is the wild type strain (Bassler et al., 1997, supra). *S. typhimurium* strain LT2 was obtained from Dr. K. Hughes (University of Washington), *S. typhimurium* 14028 is ATCC strain 14028 Organism: *Salmonella choleraesuis*. *E. coli* O157:H7 is a clinical isolate supplied by Dr. Paddy Gibb (University of Calgary). Luria broth (LB) contained 10 g Bacto Tryptone (Difco), 5 g Yeast Extract (Difco) and 10 g NaCl per liter. The recipe for Autoinducer Bioassay (AB) medium has been reported previously (Greenberg, E. P., Hastings, J. W., and Ulitzur, S. (1979) *Arch. Microbiol.* 120, 87–91). Where specified, glucose was added from a sterile 20% stock to a final concentration of 0.5%. Antibiotics were used at the following concentrations (mg/L): Ampicillin (Amp) 100, Chloramphenicol (Cm) 10, Gentamycin (Gn) 100, Kanamycin (Kn) 100, and Tetracycline (Tet) 10. DNA isolation, restriction analysis and transformation of *E. coli* was performed as described by Sambrook et al. Probes for Southern Blot analysis were labeled using the Multiprime DNA labeling system of Amersham. Sequencing was carried out using an Applied Biosystems sequencing apparatus. The *V. harveyi* BB120 genomic library was constructed in the cosmid pLAFR2 as described (Bassler et al., 1993, supra). The method for Tn5 mutagenesis of cloned *V. harveyi* genes, and the allelic replacement technique for inserting Tn5 mutated genes into the *V. harveyi* chromosome have been reported (Bassler et al., 1993, supra).

Bioluminescence Assay. The AI-2 bioassay using the *V. harveyi* reporter strain BB170 (Sensor 1$^-$, Sensor 2$^+$) has been discussed in the previous examples. Cell-free culture fluids from *V. harveyi*, *E. coli*, or *S. typhimurium* strains to be tested for AI-2 activity were prepared as described above, and assayed at 10% (v/v). AI-2 activity is reported as the fold-induction of the reporter strain over background, or as the percent of the activity obtained from *V. harveyi* BB120 (wild type) cell-free culture fluid.

"Mutagenesis and analysis of the AI-2 production gene in *S. typhimurium* LT2. MudJ insertion mutants of *S. typhimurium* LT2 were generated using a phage P22 delivery system as described (Maloy, S. R., Stewart, V. J., and Taylor, R. K. (1996) *Genetic analysis of pathogenic bacteria: a laboratory manual*. Cold Spring Harbor Laboratory Press, Cold Spring Harbor, N.Y.). Following growth to mid-exponential phase in LB containing 0.5% glucose, the *S. typhimurium* insertion mutants were tested for AI-2 production using the *V. harveyi* BB 170 bioassay. The site of the MudJ insertion that inactivated the AI-2 production function in *S. tyhimurium* was identified by PCR amplification and sequencing of the chromosomal DNA at the insertion junction. A two-step amplification procedure was used (Caetano-Annoles, G. (1993) *Meth. Appl.* 3, 85–92). In the first PCR reaction, the arbitrary primer 5'-GGCCACGCGTCGACTAGTACNN-NNNNNNNNACGCCC-3' (SEQ ID NO: 21), and the MudJ specific primer 5'-GCACTACAGGCTTGCAAGCCC-3' (SEQ ID NO: 22) were used. Next, 1l of this PCR reaction was used as the template in a second PCR amplification employing a second arbitrary primer (5'-GGCCACGCGTCGACTAGTCA-3')(SEQ ID NO: 23) and another MudJ specific primer (5'-TCTAATCCATCAGATCCCG-3') (SEQ ID NO: 24). The PCT product from the second reaction was purified and sequenced.

"Cloning and sequencing of the *E. coli* MG1655, *E. coli* O157:H7, and *E. coli* DH5 AI-2 production genes. The DNA sequence obtained from the *S. typhimurium* LT2 MudJ screen was used to search the *E. coli* MG1655 genome sequence to identify the corresponding *E. coli* region (Blattner et al., *Science* 277 1453–1462, 1997). The gene identified from the sequencing project had the designation ygaG. Primers that flanked the ygaG gene and incorporated restriction sites were designed and used to amplify the *E. coli* MG1655, *E. coli* O157:H7 and *E. coli* DH5 ygaG genes. The primers used are: 5'-GTGAAGCTTGTTTACTGACTAGATC-3' (SEQ ID NO: 25) and 5'-GTGTCTAGAAAAACACGCCTGACAG-3' (SEQ ID NO: 26). The PCR products were purified, digested and cloned into pUC19. In each case, the PCR products from three independent reactions were cloned and sequenced.

Results

Identification and cloning of the gene responsible for AI-2 production in *V. harveyi*. We have discussed in previous examples that, unlike many other *E. coli* strains, *E. coli* strain DH5 does not produce an AI-2 signal molecule that can be detected by *V. harveyi*. We reasoned therefore, that we could use *E. coli* DH5 as a mutant to clone the *V. harveyi* AI-2 production gene. A library of wild type *V. harveyi* BB120 genomic DNA was transformed into *E. coli* strain DH5, and the transformants were screened for AI-2 production in the *V. harveyi* BB170 AI-2 detection bioassay. The library consisted of 2,500 clones each containing roughly 25 kb of *V. harveyi* genomic DNA. Five DH5 clones were identified that resulted in upwards of 300-fold stimulation of the reporter strain in the bioassay.

Figure 9A:
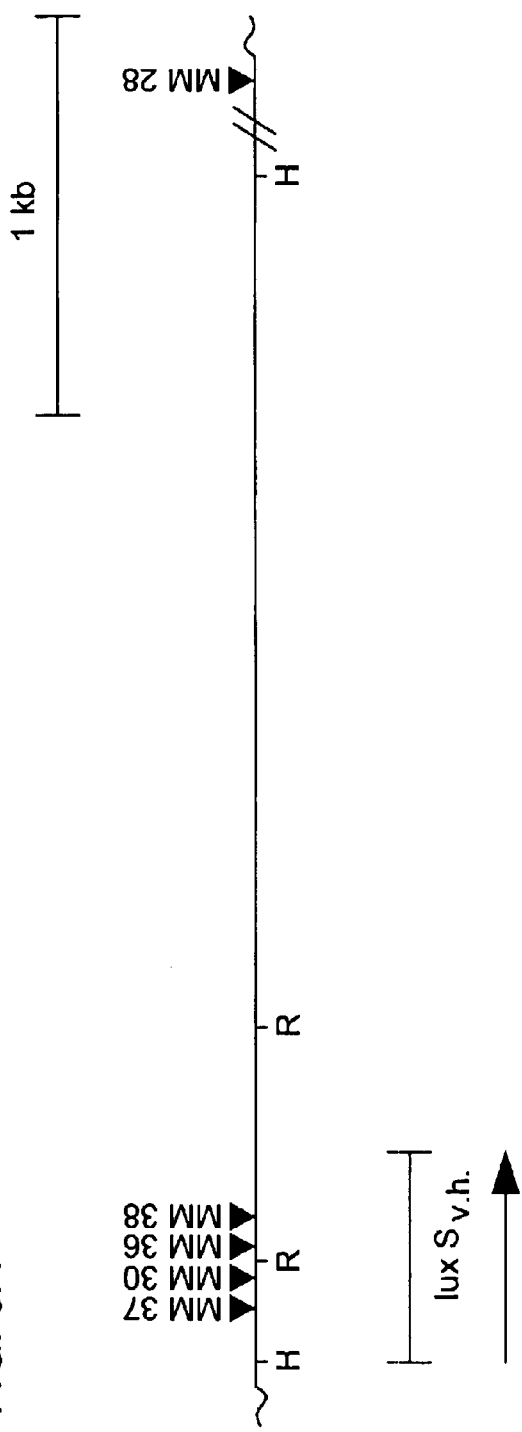
FIGS. 9A–B. The luxS and ygaG genes from *V. harveyi* and *E. coli* MG1655.

The recombinant cosmid DNA from the five AI-2 producing *E. coli* DH5 clones was analyzed by restriction analysis and Southern blotting. All five of the cosmids contained an overlapping subset of identical *V. harveyi* genomic restriction fragments, indicating that we had cloned the same locus several times. One cosmid, called pBB2929 was selected for further analysis. Random mutagenesis using transposon Tn5 was carried out on cosmid pBB2929, and pools of cosmids harboring Tn5 insertions were subsequently transformed into *E. coli* DH5. We tested 962 individual *E. coli* DH5/pBB2929::Tn5 strains for the loss of the ability to produce AI-2. Four *E. coli* DH5 strains harboring Tn5 insertions in pBB2929 were identified that failed to produce AI-2. We mapped the locations of these Tn5 insertions in pBB2929 and found that all four transposon insertions resided in the same 2.6 kb HindIII *V. harveyi* genomic DNA fragment (FIG. 9A).

Cosmid pBB2929 was digested with HindIII and the 8 resulting fragments were subcloned in both orientations into pALTER (Promega). The pALTER subclones were transformed into *E. coli* DH5, and subsequently tested for AI-2 production. The only strains capable of producing AI-2 contained the 2.6 kb HindIII fragment identified in the Tn5 mutagenesis. This fragment was sequenced, and only one open reading frame (ORF) could be identified, and its location corresponded to the map positions of the four Tn5 insertions that eliminated AI-2 production. We named the ORF luxS$_{V.h.}$ (FIG. 9A).

Mutagenesis of luxS$_{V.h.}$ in *V. harveyi*. We analyzed the effects of luxS$_{V.h.}$ null mutations on AI-2 production in *V. harveyi*. The four Tn5 insertions that mapped to the luxS$_{V.h.}$ gene and the control Tn5 insertion adjacent to the luxS$_{V.h.}$ locus were transferred to the corresponding locations in the *V. harveyi* BB120 chromosome to make strains MM37, MM30, MM36, MM38 and MM28 respectively (FIG. 9A). Southern blotting was used to confirm the correct placement of all five Tn5 insertions in the *V. harveyi* chromosome. The four *V. harveyi* luxS$_{V.h.}$::Tn5 insertion strains were tested for the ability to produce AI-2, and all four strains gave identical results.

Figures 10A, 10B:
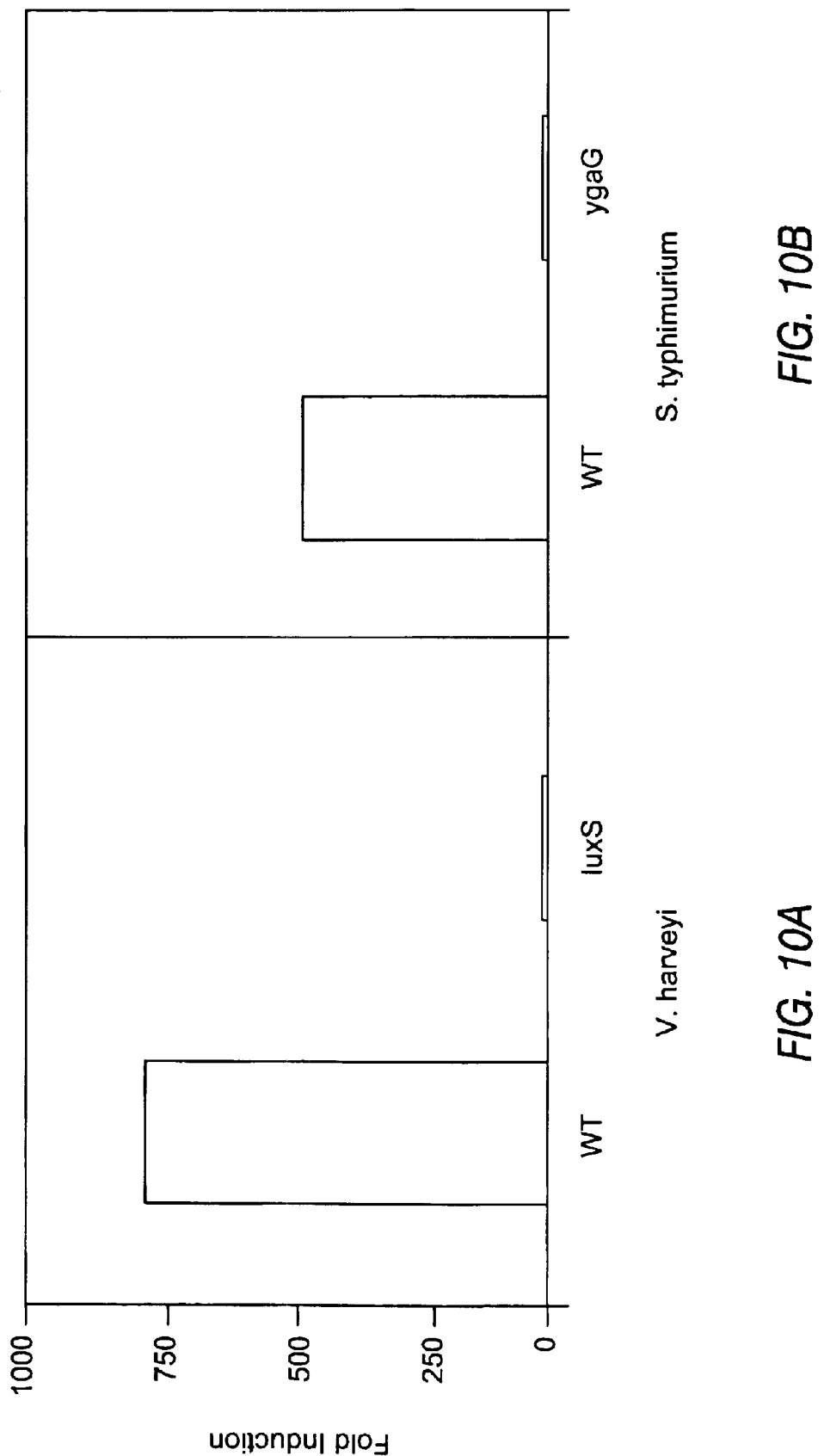
FIGS. 10A–B. Autoinducer production phenotypes of *V. harveyi* and *S. typhimurium* strains. Cell-free culture fluids from *V. harveyi* and *S. typhimurium* strains were prepared and tested for AI-2 activity in the *V. harveyi* BB170 bioassay.

In FIG. 10A, we show the AI-2 production phenotypes of the wild type control Tn5 insertion strain MM28 and one representative luxS$_{V.h.}$::Tn5 insertion strain, MM30. *V. harveyi* MM28 and MM30 were grown to high cell density, after which cell-free culture fluids were prepared. The culture fluids were assayed for AI-2 activity by the ability to induce luminescence in the AI-2 detector strain BB170. FIG. 10A shows that addition of culture fluids from the control Tn5 insertion strain MM28 induced luminescence in the reporter 780-fold, while culture fluid from the luxS$_{V.h.}$::Tn5 insertion strain MM30 did not induce the expression of luminescence in the reporter. Therefore, a null mutation in luxS$_{V.h.}$ in *V. harveyi* eliminates AI-2 production.

Identification and analysis of *S. typhimurium* autoinducer production mutants. In order to identify the gene responsible for AI-2 production in *S. typhimurium*, we randomly mutagenized *S. typhimurium* LT2 using the MudJ transposon (Maloy et al., 1996, supra). Ten-thousand *S. typhimurium* LT2 insertion mutants were assayed for AI-2 production in the *V. harveyi* BB170 bioassay. One *S. typhimurium* MudJ insertion mutant (strain CS132) was identified that lacked detectable AI-2 in culture fluids at mid-exponential phase.

FIG. 10B shows the AI-2 production phenotypes of *S. typhimurium* strain LT2 and the corresponding MudJ insertion strain CS132. The strains were grown to mid-exponential phase in LB containing glucose, and cell-free culture fluids were prepared and assayed for AI-2. *S. typhimurium* LT2 culture fluids induced the reporter strain 500-fold, while culture fluids from strain CS132 contained no AI-2 activity. Furthermore, strain CS132 did not produce AI-2 under any of the growth conditions that we have previously reported induce AI-2 production in *S. typhimurium* (not shown).

Figure 9B:
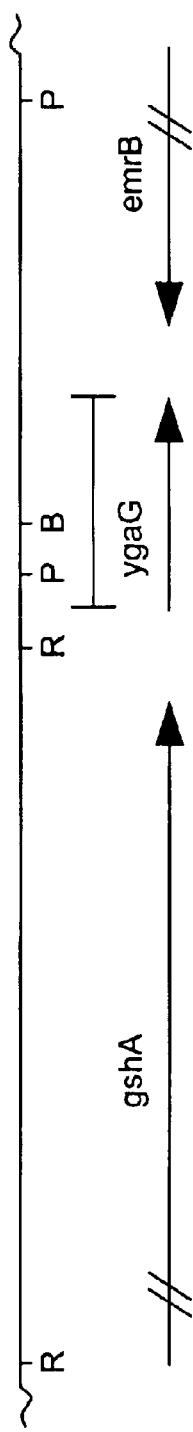

The site of the MudJ insertion in *S. typhimurium* CS132 was determined by PCR amplification followed by sequencing of the 110 bp of chromosomal DNA adjacent to the transposon. This sequence was used to search the database for DNA homologies. The sequence matched a site (89/105 bp identity) in the *E. coli* MG1655 genome that corresponded to an ORF of unknown function denoted ygaG (Blattner et al., 1997, supra). In the chromosome, the *E. coli* ygaG gene is flanked by the gshA and emrB genes (FIG. 9B). The ygaG gene is transcribed from its own promoter which is located immediately upstream of the gene, indicating that it is not in an operon with gsha. The emrB gene is transcribed in the opposite direction. We PCR amplified the ygaG region from the chromosomes of *E. coli* O157:H7 and *E. coli* MG1655, and the two *E. coli* ygaG genes were cloned into pUC19.

Figure 11A:
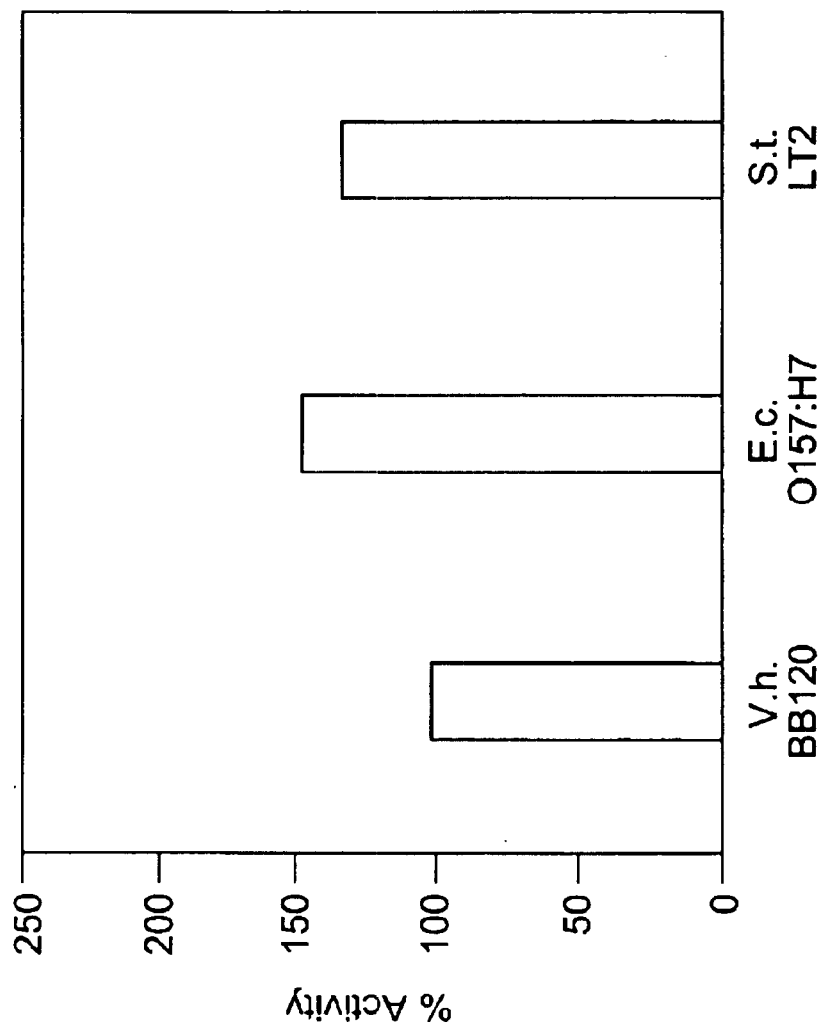
FIGS. 11A–C. Complementation of AI-2 production in *S. typhimurium* CS132 and *E. coli* DH5. Cell-free culture fluids from *E. coli* and *S. typhimurium* strains were tested for AI-2 activity in the bioassay. The activity present in these fluids was compared to that produced by wild type *V. harveyi* BB120. In the figure, the level of BB120 activity was normalized to 100%.

Complementation of *S. typhimurium* and *E. coli* AI-2-mutants. We tested whether the *E. coli* O157:H7 ygaG gene and the *V. harveyi* luxS$_{V.h.}$ gene could restore AI-2 production in the AI-2 strains *S. typhimurium* CS132 and *E. coli* DH5. In FIG. 11A, we show the AI-2 activity produced by wild type *V. harveyi* BB120, *E. coli* O157:H7 and *S. typhimurium* LT2. In this figure, the level of AI-2 activity present in *V. harveyi* BB120 cell-free culture fluids was normalized to 100%, and the activities in cell-free culture fluids from *E. coli* and *S. typhimurium* compared to that. In this experiment, *E. coli* O157:H7 produced 1.5 times and *S. typhimurium* LT2 produced 1.4 times more AI-2 activity than *V. harveyi* BB120 (i.e., 150% and 141% respectively).

Figures 11B, 11C:
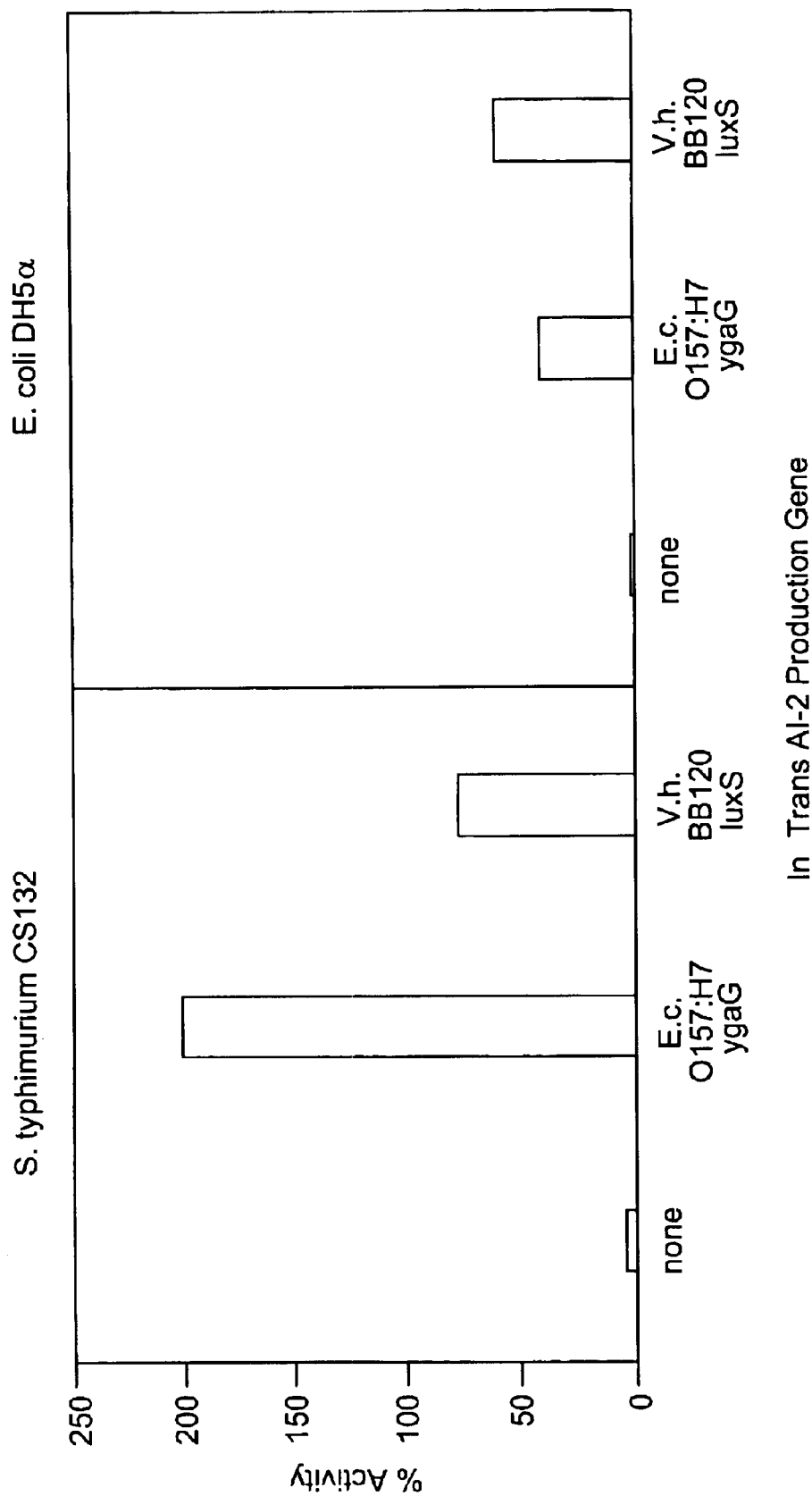

FIGS. 11B and 11C show the AI-2 complementation results for *S. typhimurium* CS132 and *E. coli* DH5. FIG. 11B demonstrates that introduction of the *E. coli* O157:H7 ygaG gene into *S. typhimurium* CS132 restored AI-2 production beyond the level of production of wild type *S. typhimurium* (i.e., 209% activity). Comparison of the data in FIGS. 11A and 11B shows that the *E. coli* ygaG gene in *S. typhimurium* resulted in AI-2 production exceeding that produced in vivo by *E. coli* O157:H7. Introduction of the *V. harveyi* luxS$_{V.h.}$ gene into *S. typhimurium* resulted in AI-2 production at slightly less than the level produced by wild type *V. harveyi* BB120 (i.e., 73% of the level of *V. harveyi* BB120). FIG. 11C shows that *E. coli* DH5 was also complemented to AI-2 production by both the cloned *E. coli* O157:H7 and the *V. harveyi* BB120 AI-2 production genes. However, introduction of *E. coli* O157:H7 ygaG and *V. harveyi* BB120 luxS$_{V.h.}$ into *E. coli* DH5 resulted in only 31% and 43% of the *V. harveyi* BB120 AI-2 activity respectively. FIGS. 11B and 11C show that the control vectors produced no activity in the complementation experiments.

Analysis of the AI-2 production genes from *V. harveyi*, *E. coli* and *S. typhimurium*. We sequenced the AI-2 production gene luxS$_{V.h.}$ from *V. harveyi* BB120 and the ygaG loci from *E. coli* O157:H7, *E. coli* MG1655 and *E. coli* DH5. The translated protein sequences encoded by the ygaG ORF's are shown in FIG. 12, and they are aligned with the translated LuxS protein sequence from *V. harveyi*. The non-bold, underlined amino acids indicate the residues in the *E. coli* proteins that differ from the *V. harveyi* LuxS protein. The ygaG loci from *E. coli* encode proteins that are highly homologous to one another and also to LuxS from *V. harveyi*. The *E. coli* MG1655 and the *E. coli* O157:H7 YgaG proteins are 77% and 76% identical to LuxS from *V. harveyi* BB120. The DNA sequence we determined for ygaG from *E. coli* O157:H7 differs at five sites from the reported (and our) sequence for the *E. coli* MG1655 ygaG gene. Four of the changes are silent, the fifth results in a conservative Ala to Val alteration at amino acid residue 103 in the *E. coli* O157:H7 protein.

Identification of the ygaG locus in *E. coli* MG1655 and *E. coli* O157:H7 allowed us to investigate the AI-2 production defect in *E. coli* DH5. *E. coli* DH5 possesses the ygaG gene because we could PCR amplify this region from the chromosome using the same primers we employed to amplify it from *E. coli* MG1655 and *E. coli* O157:H7. Examination of the *E. coli* DH5 ygaG promoter showed that it is identical to that of *E. coli* MG1655, indicating that the AI-2 defect in *E. coli* DH5 is not simply due to decreased transcription of ygaG. However, sequence analysis of the *E. coli* DH5 ygaG coding region showed that a one G-C base pair deletion and a T to A transversion exist at bp 222 and 224 respectively. The frameshift mutation resulting from the G/C deletion causes premature truncation of the *E. coli* DH5 protein. FIG. 12 shows that the truncated *E. coli* DH5 protein is 111 amino acids, while the *E. coli* MG1655 and *E. coli* O157:H7 proteins are 171 residues. Twenty altered amino acids are translated after the frame shift and prior to termination of the protein. Our complementation results (FIG. 11) demonstrate that the AI-2 production defect in *E. coli* DH5 is recessive to in trans expression of ygaG, which is consistent with the defect being due to a null mutation caused by the frame shift in the *E. coli* DH5 ygaG gene.

We searched the *S. typhimurium* database using the sequence we obtained adjacent to the MudJ that inactivated the AI-2 production function in *S. typhimurium* CS132. A perfect match (110/110 bp) was identified to fragment B_TR7095.85-T7 in the *S. typhimurium* LT2 genome sequencing database (Genome Sequencing Center, Washington University, St. Louis). However, the *S. typhimurium* LT2 database ygaG sequence is incomplete (FIG. 12). The translated sequence matches the *E. coli* and *V. harveyi* sequences beginning at amino acid residue 8. The translated sequence shows that the *S. typhimurium* protein is 75% identical to LuxS of *V. harveyi*. In order to align the *S. typhimurium* sequence with the *V. harveyi* LuxS protein, we corrected three apparent frame shift errors in the database sequence. Considering that only crude, unannotated sequence data is currently available for *S. typhimurium*, we predict that the *S. typhimurium* protein contains 7 more amino acids, and that the frame shift mutations are sequencing errors. We were unsuccessful at PCR amplifying either the *S. typhimurium* 14028 or the *S. typhimurium* LT2 ygaG gene using the primers designed for *E. coli*, so we do not yet have the complete sequence of the *S. typhimurium* gene.

The results set forth above indicate that the genes we have identified and analyzed encode a novel family of proteins responsible for autoinducer production. Members of this new family of genes, referred to herein as LuxS, are highly homologous to one another but not to any other identified genes. The encoded product of the LuxS genes catalyze an essential step in the synthesis of the signaling molecules of the present invention.

EXAMPLE 4

Construction of a Sensor 1⁻, AI⁻2⁻ *V. harveyi* Reporter Strain

*V. harveyi* null mutants in each of the lux genes luxL, luxM, luxN, luxS and luxQ have been constructed. These mutants fail to either make or respond to one specific autoinducer, but they still produce light because, in each case, one quorum sensing system remains operational. A double luxN, luxS *V. harveyi* mutant will not emit light without the addition of exogenous AI-2 because this mutant will not respond to AI-1 and it will not produce AI-2.

The *V. harveyi* luxS gene has been cloned into *E. coli* DH5α on a broad host range mobilizable cosmid called pLAFR2. This construction restores AI-2 production to *E. coli* DH5α. A marked null mutation was engineered into the luxS gene by introducing a chloramphenicol resistance (Cm$^r$) cassette into an internal restriction site. Placement of the Cm$^r$ cassette at this site in luxS subsequently eliminated AI-2 production in *E. coli* DH5α.

The luxS::Cm$^r$ null allele was transferred onto the chromosome of *V. harveyi* strain BB170. Strain BB170 contains a Tn5Kan$^r$ in luxN and does not respond to AI-1. To construct the double mutant, triparental conjugations were carried out by mixing stationary phase cultures of *E. coli* DH5α carrying the *V. harveyi* luxS::CM$^r$ construction in pLAFR2 (pLAFR2 carries tetracycline resistance), *E. coli* DH5a carrying the tra donor plasmid pRK2013 and the *V. harveyi* recipient strain BB170. Exchange of the luxS::Cm$^r$ mutant allele for the wild type luxS allele on the chromosome occurs by homologous recombination. The exogenote cosmid in *V. harveyi* was eliminated by the introduction of a second incompatible plasmid pPH1JI. This was accomplished by mating *E. coli* DH5α containing pPH1JI with the *V. harveyi* BB170 recipient containing the luxS::Cm$^r$ cosmid, and selecting for exconjugants on plates containing ampicillin (for counter selection of the *E. coli* donor) chloramphenicol (for inheritance of the mutant luxS::Cm$^r$ allele) and gentamicin (for maintenance of the plasmid pPH1JI). Southern blot analysis was used to verify that the exogenote pLAFR2 cosmid has been eliminated and that the luxS::Cm$^r$ construction had been transferred to the corresponding position in the genome of *V. harveyi*. The pPH1JI cosmid was subsequently eliminated by growth in the absence of gentamicin selection.

Verification that the luxN, luxS Double Mutant Responds to AI-2. The *V. harveyi* strain that is mutant in luxN and luxS was stimulated to produce light in response to the exogenous addition of AI-2 but not AI-1. This was verified in a luminescence assay for response to *V. harveyi* AI-1 and AI-2. *V. harveyi* strain MM30 (luxS::Tn5) which is phenotypically AI-1⁺, AI-2⁻, and *V. harveyi* strain BB152 (luxM::Tn5) which is phenotypically AI-1⁻, AI-2⁺ were used as the sources of AI-1 and AI-2 respectively. The AI-1 and AI-2 present in culture fluids of these strains was tested for stimulation of light production of the *V. harveyi* luxN, luxS double mutant reporter strain. In this assay, autoinducer preparations from MM30, BB152 or sterile medium controls were added to the wells of microtiter plates, followed by the addition of the *V. harveyi* reporter strain. The resulting light production was monitored using a liquid scintillation counter in the chemiluminescence mode. Maximal stimulation of light production in the *V. harveyi* luxN, luxS reporter strain was compared to that produced by the Sensor 1⁺, Sensor 2⁻ *V. harveyi* strain BB886 and the Sensor 1⁻, Sensor 2⁺ *V. harveyi* strain BB170. These two *V. harveyi* strains are routinely used in this assay as reporters of AI-1 and AI-2 activity respectively.

Determine optimum concentrations of AI-2 in microtiter assays. The aforementioned screen will be optimized for use in 96-well microtiter assays. The screen will be used in inhibitor assays for identifying inhibitors of AI-2. Purified or synthetic AI-2 will be added to the microtiter wells containing the newly constructed reporter strain and inhibition will be measured by a decrease in light emission from the wells containing an inhibitor. The assay will be optimized by determining the concentration of cells and AI-2 in the microtiter wells that will allow for maximal sensitivity. The optimal AI-2 concentration will be that which stimulates half-maximal light output for a given concentration of cells per unit time. Initial experiments will be conducted in this concentration range to determine the range of AI-2 concentration that produces the greatest change in light output. Similar experiments using AI-1 and a non self-stimulating sensor-1⁺, sensor-2⁻ mutant (BB886) showed that the assay was sensitive to concentrations as low as 100 nM AI-1 and that light emission was linear over 6 orders of magnitude (light emission from a self-stimulating strain was linear over 3 orders). Similar results for AI-2 using the new reporter strain which will not self-stimulate and therefore have zero background light emission are predicted. Light emission from the microtiter wells will be measured with a Wallac TriLux liquid scintillation counter model 1450-021 in the chemiluminescence mode. This machine will accommodate 16 plates and will therefore allow for 1536 separate concentration experiments per run.

EXAMPLE 5
In-vitro Method for Synthesizing AI-2

Purification and Identification of AI-2. The AI-2 class of molecule is refractory to purification by conventional techniques used for the isolation of acyl-homoserine lactone (HSL) autoinducers such as AI-1 from *V. harveyi*. Unlike other HSL autoinducers, under the conditions tested, the AI-2 activity does not extract quantitatively into organic solvents. Furthermore, it fails to bind to either a cation or anion exchange column. The present characterization of AI-2 indicates that it has a molecular weight of less than 1000 kDa, and is a polar but apparently uncharged organic compound. The AI-2 activity is acid stable and base labile and heat resistant to about 80 but not 100° C. These results indicate that the AI-2's are not acyl-homoserine lactones. The luxS genes identified in the present study bear no homology to other genes known to be involved in production of HSL autoinducers further indicating that the present AI-2 class of autoinducers is novel.

Thus, in addition to providing a cloned, overexpressed and purified *S. typhimurium* LuxS protein, the present invention also provides a method for producing AI-2 in vitro. The present invention provides a mechanism for generating large quantities of pure AI-2 useful for mass spectral and NMR analysis, and for screening compounds which modulate the activity of AI-2. Moreover, the present invention provides a method for determining the in vivo biosynthetic pathway for AI-2 synthesis.

Figure 15:
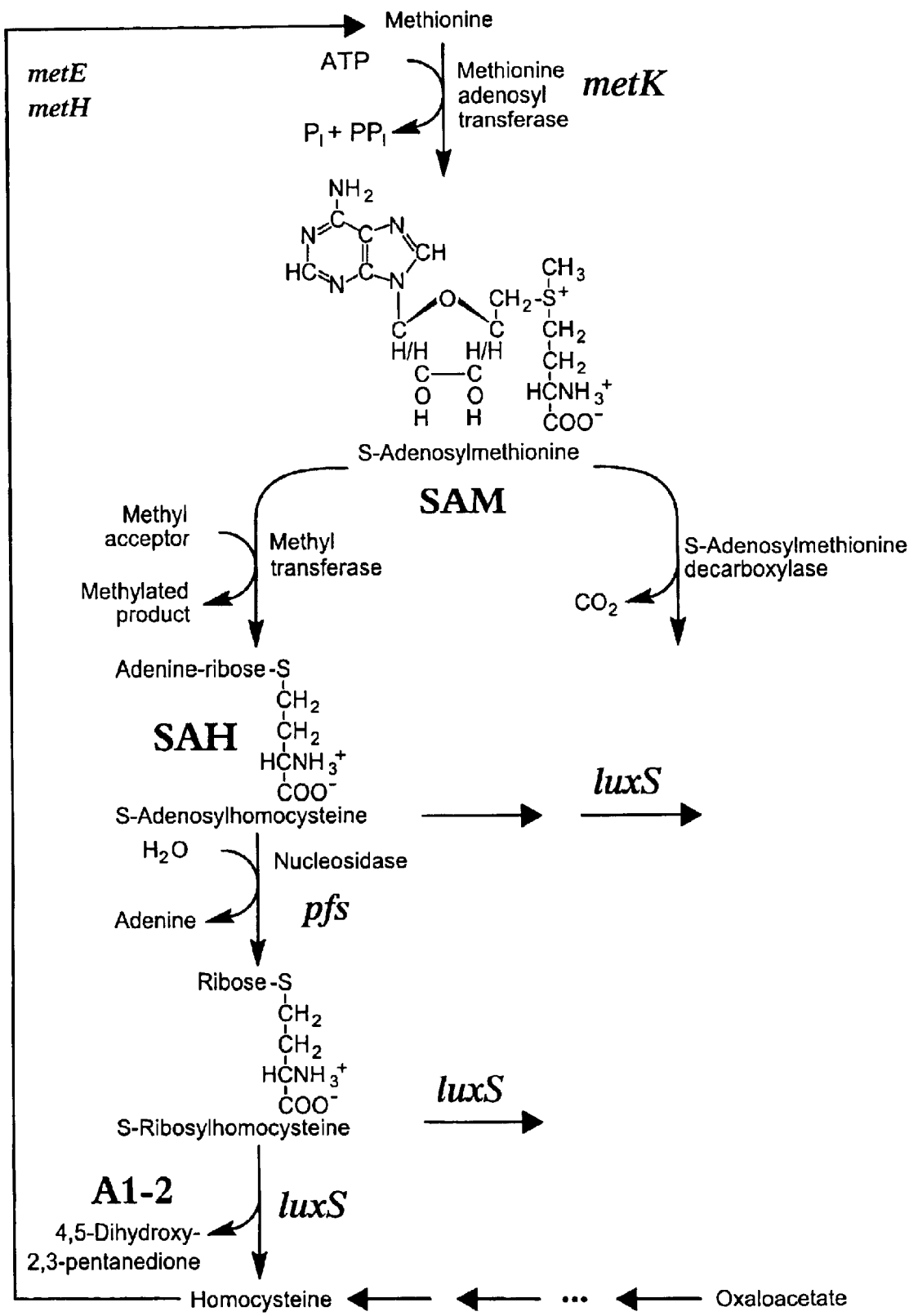
FIG. 15. A diagram of the biosynthetic pathway of autoinducer-2 (AI-2) is shown.

The analysis of the genomic locations of the various luxS genes identified in the present invention indicates that the luxS genes do not consistently reside in any one location in the chromosome, nor are they typically found in close proximity to any specific gene(s). However, in one case, the luxS gene is the third gene in a three-gene operon with two genes (metK and pfs). In *E. coli*, Salmonella and many other bacteria, MetK and Pfs are involved in the conversion of S-adenosyl methionine (SAM) to homocysteine and 4,5-dihydroxy-2,3 pentanedione (FIG. 15). The function of MetK is to convert methionine to SAM which is an important cofactor in one-carbon metabolism. SAM is used to methylate DNA, RNA and a variety of cell proteins, and several SAM dependent methyl transferases act at this step. S-adenosyl homocysteine (SAH) is produced when the methyl group is transferred from SAM to its substrates. SAH functions as a potent inhibitor of SAM dependent methyltransferases. Therefore, bacteria rapidly degrade SAH via the enzyme Pfs. The designation "pfs" refers to an open reading frame in the *E.coli* genome that has recently been determined to encode the enzyme 5'-methylthioadenosine/S-adenosylhomocysteine nucleosidase, also known as MTA/SAH nucleosidase. In the present system, the enzyme cleaves the glycosidic bond in S-adenosylhomocycteine (SAH). Thus, the function of Pfs is to convert SAH to adenine and S-ribosyl homocysteine. In a final step, S-ribosyl homocysteine is converted to homocysteine and 4,5-dihydroxy-2,3-pentanedione. Homocysteine can re-enter this pathway; it is methylated to generate methionine which can be converted to SAM by MetK.

The catabolism of SAH is considered a salvage pathway for recycling metabolic intermediates (adenine and homocysteine). However, some species of bacteria eliminate SAH by a different pathway. In this alternative pathway, adenosine is directly removed from SAH which generates homocysteine. Therefore, cells that use this second mechanism do not produce 4,5-dihydroxy-2,3-pentanedione. In the pathway shown in FIG. 15, the enzyme responsible for conversion of S-ribosyl homocysteine to 4,5-dihydroxy-2,3-pentanedione has never been identified, cloned or purified. Furthermore, no role for 4,5-dihydroxy-2,3-pentanedione is known.

LuxS is involved in the pathway shown in FIG. 15, and SAM and SAH are involved in AI-2 production. The structure of AI-2 could be 4,5-dihydroxy-2,3-pentanedione, in which case LuxS is the uncharacterized enzyme that acts on S-ribosyl homocysteine. Second, LuxS could act on one of the intermediates to make AI-2. LuxS would represent a branch point off the known pathway.

To confirm that LuxS is involved in the conversion of SAM to AI-2, the gene encoding the *S. typhimurium* LuxS protein was cloned, overexpressed and the *S. typhimurium* LuxS protein was purified. This protein was used in combination with dialyzed cell-free extracts prepared from a *S. typhimurium* luxS null mutant to show that addition of SAM and LuxS protein could restore AI-2 production to dialyzed LuxS-cell extracts. Reaction mixtures were prepared containing 10 mM Sodium Phosphate buffer pH 7.0, dialyzed *S. typhimurium* LuxS-cell extract and SAM. Purified LuxS protein was added to some of these mixtures. The reactions were incubated at room temperature for 60 min, followed by centrifugation in a 5000 MWCO centricon. The material with MW<5000 was added to the standard *V. harveyi* bioassay as previously described. Dialyzed LuxS-cell extracts to which SAM was added or extracts containing LuxS protein without the addition of SAM produced no AI-2 activity. However, identical extracts to which LuxS protein and SAM had been added produced AI-2 that resulted in over 500-fold stimulation in light production in the bioassay.

Further investigation showed that SAM is not the direct substrate for LuxS, and that LuxS must act at a step subsequent to the conversion of SAM to SAH (FIG. 15). It was determined that AI-2 was not produced if SAM was added directly to LuxS protein, however activity was produced by pre-incubation of SAM with the LuxS-extracts, filtration, and subsequent addition of LuxS protein to the filtrate. Importantly, these studies indicate that SAM can react with an element in the cell extract before it can be used by LuxS to make AI-2. Presumably, the SAM dependent methyl transferases present in the cell extract use SAM as a methyl donor and convert it to SAH in the process. To verify this, SAH was substituted for SAM in an in vitro assay. Addition of SAH to the in vitro assay resulted in much greater AI-2 production than when SAM was added. This result indicates that LuxS functions in the pathway subsequent to the conversion of SAM to SAH. Again, addition of SAH directly to LuxS protein is not sufficient for production of AI-2 activity, while pre-incubation of SAH with dialyzed LuxS-extracts followed by filtration and subsequent addition of LuxS protein to the filtrates does result in AI-2 production. Presumably SAH is converted to S-ribosyl homocysteine and then LuxS acts to produce AI-2.

The proposed pathway shown in FIG. 15 is not a salvage pathway for recycling secondary metabolites, but rather is the pathway for production of AI-2. The present invention has narrowed the possibilities for point of LuxS activity in the biosynthesis of AI-2. The remaining possibilities are shown in FIG. 15 (designated LuxS?).

According to the invention, AI-2 is a derativive of ribose. It is noteworthy that, in *V. harveyi*, LuxP, the primary sensor for AI-2, is a homologue of the *E. coli* and *S. typhimurium* ribose binding protein.

Characterization and Biosynthesis of AI-2. The invention further provides a method for an in vitro procedure for large scale production of pure AI-2. As indicated in FIG. 15, SAH is a precursor in the LuxS dependent biosynthesis of AI-2. Furthermore, LuxS does not act directly on SAH. Prior to the action of LuxS, SAH must first be acted on by some enzyme in dialyzed cell extracts. Presumably this step is the conversion of SAH to S-ribosyl homocysteine by Pfs. Therefore the substrate for LuxS is S-ribosyl homocysteine.

To confirm that LuxS acts on S-ribosyl homocysteine, the Pfs enzyme can be purified and used to convert SAH to S-ribosyl homocysteine. Toward this end, the pfs gene has been cloned from *S. typhimurium* 14028 placed into the overexpression vector pLM-1. The Pfs enzyme will be overexpressed and SAH will be added to purified Pfs to produce S-ribosyl homocysteine. The conversion of SAH to S-ribosyl homocysteine will be confirmed by reverse phase HPLC analysis (SAH is UV active while S-ribosyl homocysteine is not). Subsequently, the S-ribosyl homocysteine produced by Pfs will be added to purified LuxS. Following incubation, the mixture will be filtered over a 5000 MWCO centricon. The filtrate will be tested for AI-2 activity in the previously described *V. harveyi* bioassay. The identification of activity will confirm that 4,5-dihydroxy-2,3-pentanedione is AI-2.

In addition, AI-2 structure obtained from *E. coli* and *V. harveyi* AI-2 will be determined. The *E. coli* and *V. harveyi* luxS genes have been cloned in to overexpression vectors. The identity/biosynthesis of the *S. typhimurium* AI-2 provided by the present invention should greatly facilitate these analyses. In the event that the *S. typhimurium*, *E. coli* and *V. harveyi* AI-2's are identical these data will indicate that AI-2's are the same.

The present invention is not limited to the embodiments described and exemplified above, but is capable of variation and modification within the scope of the appended claims.

What is claimed is:

1. An isolated nucleic acid that comprises the sequence of SEQ ID NO:1, wherein the sequence encodes a polypeptide that catalyzes conversion of S-ribosylhomocysteine to homocysteine, wherein the sequence is operably linked to a heterologous regulatory sequence, and wherein the heterologous regulatory sequence directs expression of the polypeptide encoded by SEQ ID NO:1.

2. A vector comprising the nucleic acid of claim 1.

3. A host cell comprising the nucleic acid of claim 1.

4. An isolated nucleic acid that encodes a polypeptide that catalyses the conversion of S-ribosylhomocysteine to homocysteine, that is operably linked to a heterologous regulatory sequence that directs expression of the polypeptide, and that hybridizes to the sequence of SEQ ID NO: 1 under high stringency hybridization conditions, the high stringency hybridization conditions being 5×SSC, 5× Denhardt's reagent, 1.0% SDS, 100 g/ml denatured, fragmented salmon sperm DNA, 0.05% sodium pyrophosphate and up to 50% formamide at 37–42° C. for at least six hours, followed by washing for 5 minutes at room temperature in 2×SSC and 1% SDS, for 15 minutes at room temperature in 2×SSC and 0.1% SDS, for 30 minutes–1 hour at 37° C. in 1×SSC and 1% SDS, and for 2 hours at 42–65° C. in 1×SSC and 1% SDS.

5. A vector comprising the nucleic acid of claim 4.

6. A host cell comprising the nucleic acid of claim 4.

* * * * *